(12) United States Patent
Kawamura et al.

(10) Patent No.: US 6,686,373 B2
(45) Date of Patent: Feb. 3, 2004

(54) PYRAZOLOQUINOLINONE DERIVATIVES AS PROTEIN KINASE C INHIBITORS

(75) Inventors: Kiyoshi Kawamura, Aichi-ken (JP); Sachiko Mihara, Aichi-ken (JP); Seiji Nukui, Aichi-ken (JP); Chikara Uchida, Aichi-ken (JP)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/191,593

(22) Filed: Jul. 9, 2002

(65) Prior Publication Data

US 2003/0130277 A1 Jul. 10, 2003

Related U.S. Application Data

(60) Provisional application No. 60/304,311, filed on Jul. 9, 2001.

(51) Int. Cl.[7] .................. A61K 31/4745; C07D 471/04
(52) U.S. Cl. .................. 514/293; 546/82; 544/126; 514/232.8
(58) Field of Search .................. 514/293, 232.8; 546/82; 544/126

(56) References Cited

U.S. PATENT DOCUMENTS 6,107,305 A  8/2000  Misra et al. .................. 514/203

FOREIGN PATENT DOCUMENTS

| WO | 9740035 | 10/1997 |
| WO | 9930710 | 6/1999 |
| WO | 9936421 | 7/1999 |

OTHER PUBLICATIONS

RN 61689–24–5 and RN 101688–85–1.*
European Search Report, EP 1 310 498 A3.
Ning et al., "Intramolecular Nitrene Insertion into Nitrogen Containging Rings, Pyrolyses of 3–(1–Methyl–2–imidazolyl)–and 3–(1–Methyl–5–pyrazolyl)–2,1–benzisoxaxole (Anthranils)", J. Org. Chem., vol. 42, No. 10, 1977, pp. 1791–1794.
Adams and Hey, "Nitrosacylarylamines. Part V. The Nitrosation of 3–Acetamido–4–quinolones and quinaldones", J. Chem. Soc., 1951, pp. 1521–1527.
Ye et al., "Nitration of Pyrazolo[4,3–b]quinolinones", Chem. Heterocycl. compd., vol. 21, No. 8, 1985, pp. 905–910.

\* cited by examiner

*Primary Examiner*—C. S. Aulakh
(74) *Attorney, Agent, or Firm*—David R. Kurlandsky; Charles W. Asshbrook

(57) ABSTRACT

This invention provides a compound of the formula (I):

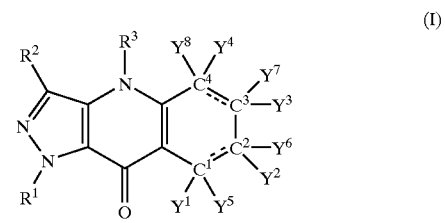

or the pharmaceutically acceptable salts thereof wherein the dashed lines represent optional double bonds; $C^1$, $C^2$, $C^3$ and $C^4$ are carbon atom; $R^1$ is $C_{1-4}$ alkyl; $R^2$ is H, amino, etc.; $R^3$ is H, halo-$CH_2$—, $C_{2-8}$ alkyl or $Q^1$-, wherein said $C_{2-8}$ alkyl is optionally substituted with up to 3 substituents selected from halo, $C_{1-3}$ alkyl, $R^4(R^5)N$, etc.; $R^4$ is H, $C_{1-7}$ alkyl, etc.; $R^5$ is H, $C_{1-7}$alkyl, etc.; $R^6$ and $R^7$ are independently selected from H and $C_{1-4}$ alkyl; $R^8$ is aryl or heteroaryl; $Q^1$ is a 4–12 membered monocyclic or bicyclic aromatic, partially saturated or fully saturated ring optionally containing up to 4 heteroatoms selected from O, N and S, and is optionally substituted with halo, $C_{1-4}$ alkyl, etc.; $Y^5$, $Y^6$, $Y^7$ and $Y^8$ are hydrogen; $Y^1$, $Y^2$, $Y^3$ and $Y^4$ are independently selected from hydrogen, halo, etc.; $Q^2$ is a 5–12 membered monocyclic or bicyclic aromatic, partially saturated or fully saturated ring optionally containing up to 3 heteroatoms selected from O, N and S, and is optionally substituted with halo, $C_{1-4}$alkyl-, etc.;

These compounds have protein kinase C inhibitory activity and thus are useful for the treatment of neuropathic pain, acute or chronic inflammatory pain, auditory deficiency (synaptic repair), or the like in mammalian, especially humans. This invention also provides a pharmaceutical composition comprising the above compound.

29 Claims, No Drawings

PYRAZOLOQUINOLINONE DERIVATIVES AS PROTEIN KINASE C INHIBITORS

This application claims the priority of United States provisional application 60/304,311, filed Jul. 9, 2001; the entire contents of which are hereby incorporated herein by reference.

FIELD OF THE INVENTION

This invention relates to novel pyrazoloquinolinone derivatives. These compounds are useful as inhibitors of protein kinase C (PKC), and are thus useful in the treatment of neuropathic pain, Inflammatory Pain, Diabetic Neuropathy or the like in mammalian, especially human. The present invention also relates to a pharmaceutical composition comprising the above compounds.

BACKGROUND OF THE INVENTION

Protein kinase C (PKC) was originally identified as a phospholipid-dependent, calcium- and diacylglycerol (DAG)-stimulated protein serine/threonine kinase. PKC is categorized into three groups, conventional PKC ($\alpha$, $\beta1$, $\beta2$, $\gamma$), novel PKC ($\delta$, $\epsilon$, $\eta$, $\theta$) and atypical PKC ($\iota$, $\zeta$) based on the structural difference that foster differences on calcium and lipid binding properties. Early studies demonstrated that PKC is activated in vivo by the receptor-induced second messenger DAG/tumor promoting phorbol esters and calcium. This quickly established PKC as a key regulator of cell growth and differentiation, cell survival, neurotransmission and carcinogenesis(See Bell, R. M. and Burns, D. J., J. Biol. Chem. 266: 4661–4664 (1991); Nishizuka, Y. Science 258: 607–614 (1992)).

Protein kinase C (PKC) inhibitors are found to be useful for the treatment of a variety of diseases such as neuropathic pain, acute or chronic inflammatory pain, diabetic neuropathy, sepsis, shock, ARDS, asthma, HIV infection, Alzheimer, gastric ulcer, drug resistance, diabetes and cerebral ischemia. (See *Science*, 1997, 278, 279–283; *European J. Pharmacology*, 1999, 372, 221–228; ibid, 2000, 403, 81–85; *Shock*, 1998, 9, 256–60; *J. Biol. Chem.*, 1997, 272, 12289–94; *Brain Research*, 1997, 769, 287–295; *Digestion*, 1998, 59, 40–46; *Biochemical Pharmacology*, 1999, 58, 1587–92; *Am. J. Physiology*, 1999, 276, 691–699; and *Brain Research*, 1998, 779, 254–58).

WO 97/40035 discloses N-substituted azaheterocyclic carboxylic acids and esters. WO99/36421 discloses Tricyclic N-acylated tricyclic azaheterorings compounds.

It would be desirable if there were provided protein kinase C (PKC) inhibitors which have more protein kinase C (PKC) inhibitory activities.

SUMMARY OF THE INVENTION

The present invention provides a compound of the following formula:

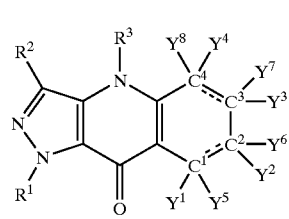

or the pharmaceutically acceptable salts thereof wherein
the dashed lines represent optional double bonds;
$R^1$ is $C_{1-4}$ alkyl;
$R^2$ is H, amino, mono- or di-($C_{1-4}$alkyl)amino or $C_{1-3}$ alkyl-(O=)CNH—;
$R^3$ is H, halo-$CH_2$—, $R^4(R^5)NCH_2$—, $R^6(R^7)NC(=O)CH_2$—, cyano-$CH_2$—, $Q^1CH_2$—, $Q^1$-(O=)CCH$_2$—, $C_{2-8}$ alkyl or $Q^1$-, wherein said $C_{2-8}$ alkyl is optionally substituted with up to 3 substituents selected from halo, $C_{1-3}$ alkyl, $R^4(R^5)N$, $C_{1-4}$ alkylsulfonylamino, $C_{1-4}$ alkylthio, $R^6(R^7)NC(=O)$—, cyano, $Q^1$-, $Q^1$-(O=)C— and $Q^1$-$C_{1-4}$ alkyl-O—;
$Y^1$, $Y^2$, $Y^3$ and $Y^4$ are independently selected from hydrogen, halo, $C_{1-4}$ alkyl, $C_{1-4}$ alkyl-O—, $C_{1-4}$ alkylthio, $Q^1$-, $R^6(R^8)N$—, $R^6N(R^7)C(=O)$—, $C_{1-4}$alkyl-O(O=)CCH=CH—, $Q^1$-(O=)CNH— and $R^6OC(=O)$—, wherein said $C_{1-4}$alkyl is optionally substituted with up to 2 substituents selected from $Q^1$, $Q^2$-, $R^6(R^7)N$—, cyano, hydroxy and $R^6(R^7)NC(=O)$—;
$Y^5$, $Y^6$, $Y^7$ and $Y^8$ are hydrogen or are absent;
$C^1$, $C^2$, $C^3$ and $C^4$ are carbon atom;
$R^4$ is H, $C_{1-7}$ alkyl, HO—$C_{1-4}$ alkyl, $Q^1$-, $Q^1$-$C_{1-4}$alkyl-, cyano- $C_{1-4}$ alkyl- or $R^6(R^7)N$ $C_{1-4}$ alkyl-;
$R^5$ is H, $C_{1-7}$alkyl, HO—$C_{1-4}$ alkyl or $Q^1$-;
$R^6$ and $R^7$ are independently selected from H and $C_{1-4}$ alkyl
$R^8$ is aryl or heteroaryl;
$Q^1$ is a 4–12 membered monocyclic or bicyclic aromatic, partially saturated or fully saturated ring optionally containing up to 4 heteroatoms selected from O, N and S, and is optionally substituted with halo, $C_{1-4}$ alkyl, amino, hydroxy, $R^6(R^7)NC_{1-4}$alkyl- or $R^6(R^7)NC_{1-4}$alkyl-O—; and
$Q^2$ is a 5–12 membered monocyclic or bicyclic aromatic, partially saturated or fully saturated ring optionally containing up to 3 heteroatoms selected from O, N and S, and is optionally substituted with halo, $C_{1-4}$alkyl-, hydroxy, $C_{1-4}$ alkoxy, nitro, amino, cyano, $R^6(R^7)N$—$C_{1-4}$alkyl-, $R^6(R^7)N$—$C_{1-4}$alkyl-O—, $R^6(R^7)N(O=)C$— or $R^6O(O=)C$—;
with the proviso that when $R^1$ is methyl and $R^2$ and $R^3$ are H, $Y^1$, $Y^2$, $Y^3$ and $Y^4$ are not H simultaneously; and when $R^1$ is methyl and $R^2$ and $R^3$ are H, $Y^2$ is not chloro.

The pyrazoloquinolinone compounds of this invention have protein kinase C (PKC) inhibitory activities and are thus useful for the treatment of disease conditions mediated by PKC activities.

Thus, the present invention provides a pharmaceutical composition for the treatment of disease conditions mediated by protein kinase C, in a mammalian subject, which comprises administering to said subject a therapeutically effective amount of a compound of formula (I).

Further, the present invention also provides a pharmaceutical composition for the treatment of neuropathic pain, acute or chronic inflammatory pain, auditory deficiency (synaptic repair), hypertension, forcal celebral ischemia, pulmonary fibrosis, diabetes, immune disease, colonic repair, drug resistance (MDR regulation), Alzheimer, sepsis, shock, ARDS, inflammation, ischemia, gastric acid regulation, diabetic neuropathy, asthma, HIV infection, gastric ulcer or cerebral ischemia or the like, which comprises a therapeutically effective amount of the imidazopyridine compound of formula (I) or its pharmaceutically acceptable salt together with a pharmaceutically acceptable carrier.

Also, the present invention provides a method for the treatment of disease conditions mediated by protein kinase C activities, in a mammalian subject, which comprises administering to said subject a therapeutically effective amount of a compound of formula (I). Further, the present invention provides a method for the treatment of the disease conditions as mentioned above.

DETAILED DESCRIPTION OF THE INVENTION

As used herein, the term "halo" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "aryl" means a monocyclic or bicyclic aromatic carbocyclic ring of 6 to 11 carbon atoms including, but not limited to, phenyl, naphthyl, indanyl, (1,2,3,4)-tetrahydronaphthyl, indenyl and isoindenyl, preferably phenyl and naphthyl.

As used herein, the term "heteroaryl" means a 5- to 10-membered monocyclic or bicyclic ring which consists of carbon atoms and from 1 to 4 heteroatoms independently selected from the group consisting of N, O and S. Examples of the heteroaryl include, but are not limited to, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl quinoxalinyl and the like.

As used herein, the term "4–12 membered monocyclic or bicyclic aromatic, partially saturated or fully saturated ring optionally containing up to 4 heteroatoms selected from O, N and S" may be, for example, but not limited to, phenyl, naphthyl, indanyl, (1,2,3,4)-tetrahydronaphthyl, indenyl, isoindenyl, azetidinyl, furyl, thienyl, pyrrolyl, pyrrolidinyl, oxazolyl, isooxazolyl, thiazolyl, isothiazolyl, imidazolyl, pyrazolyl, triazolyl, furazanyl, tetrazolyl, pyranyl, thienyl, pyridyl, piperidyl (or piperidinyl), piperidino, oxazinyl, morpholinyl, morpholino, thiamorpholino, thiazinyl, pyridazinyl, pyrimidinyl, pyrazinyl, piperazinyl, piperazino, triazinyl, benzofuranyl, isobenzofuranyl, benzothiophenyl, indolyl, isoindolyl, benzoxazolyl, benzothiazolyl, indazolyl, benzimidazolyl, chromanyl, isochromanyl, quinolyl, isoquinolyl, cinnolinyl, phthalazinyl, quinazolinyl and quinoxalinyl.

As used herein, the term "5–12 membered monocyclic or bicyclic aromatic, partially saturated or fully saturated ring optionally containing up to 3 heteroatoms selected from O, N and S" may be, for example, but not limited to, phenyl, naphthyl, indanyl, (1,2,3,4)-tetrahydronaphthyl, indenyl, furyl, thienyl, pyrrolyl, pyrrolidinyl, oxazolyl, isooxazolyl, thiazolyl, isothiazolyl, imidazolyl, pyrazolyl, triazolyl, furazanyl, pyranyl, thienyl, pyridyl, piperidyl (or piperidinyl), piperidino, oxazinyl, morpholinyl, morphorino, thiamorpholino, thiazinyl, pyridazinyl, pyrimidinyl, pyrazinyl, piperazinyl, piperazino, homopiperazinyl, homopiperazino,triazinyl, benzofuranyl, isobenzofuranyl, benzothiophenyl, indolyl, isoindolyl, benzoxazolyl, benzothiazolyl, indazolyl, benzimidazolyl, chromanyl, isochromanyl, quinolyl, isoquinolyl, cinnolinyl, phthalazinyl, quinazolinyl and quinoxalinyl.

In the compounds of formula (I),
$R^1$ is preferably $C_{1-2}$ alkyl, and most preferably $R^1$ is methyl.

In the compounds of formula (I),
$R^2$ is preferably $R^2$ is H or amino, and most preferably $R^2$ is H.

In the compounds of formula (I),
$R^3$ is preferably H, halo-$CH_2$—, $R^4(R^5)NCH_2$—, $R^6(R^7)NC(=O)CH_2$—, cyano-$CH_2$—, $Q^1CH_2$—, $Q^1$-(O=)$CCH_2$—, $C_{2-6}$ alkyl or $Q^1$-, wherein said $C_{2-6}$ alkyl is optionally substituted with up to 3 substituents selected from halo, methyl, $R^4(R^5)N$, $C_{1-2}$ alkylsulfonylamino, $C_{1-2}$ alkylthio, $R^6(R^7)NC(=O)$—, cyano, $Q^1$- and $Q^1$-(O=)C—, wherein $R^4$ is H, $C_{1-6}$ alkyl, HO—$C_{1-2}$ alkyl, $Q^1$-, $Q^1$-$C_{1-3}$alkyl-, cyano-$C_{1-2}$alkyl- or $R^6(R^7)N$ $C_{1-2}$alkyl-; $R^5$ is H, $C_{1-2}$alkyl, HO—$C_{1-2}$ alkyl or $Q^1$-; $R^6$ and $R^7$ are independently selected from H and $C_{1-2}$ alkyl; and $Q^1$ is a 4–10 membered monocyclic or bicyclic aromatic, partially saturated or fully saturated ring optionally containing up to 2 heteroatoms selected from O and N, and is optionally substituted with halo, $C_{1-2}$ alkyl, hydroxy, amino, $R^6(R^7)N$ $C_{1-2}$alkyl- or $R^6(R^7)NC_{1-2}$alkyl-O—, more preferably hydrogen, ethyl, butyl, hexyl, iodopentyl, carbamoylmethyl, methylthioethyl, (N,N-dimethylamino)ethyl, morpholinoethyl, (N,N-dimethylamino)butyl, (N,N-dimethylamino)hexyl, methansulfonylaminopropyl, (N-ethyl-N-methylamino)propyl, chloroethyl, aminoethyl, [(N,N-dimethylamino)methyl]phenyl, (N,N-dimethylamino)(methyl)propyl, (1-methyl-2-piperidinyl)ethyl, pyridylmethyl, cyanobutyl, 2-benzimidazolylmethyl, (N-methylamino)propyl, (1-methyl-2-pyrrolidinyl)ethyl, (1-azetidinyl)propyl, {N-methyl-N-[(pyridinyl)ethyl]amino}propyl, (N,N-diethylamino)propyl, [N-isopropyl-N-(methyl)amino]propyl, [N-(2-hydroxyethyl)-N-(isopropyl)amino]propyl, [N,N-bis(2-hydroxyethyl)amino]propyl, [N-(hydroxyethyl)-N-(methyl)aminopropyl, [N-ethyl-N-(propyl)amino]propyl, (4-methyl-1,4-diazepan-1-yl)propyl, [N-hexyl-N-(methyl)amino]propyl, [N-(cyanomethyl)-N-(propyl)amino]propyl, [N-[(diethylamino)ethyl]-N-(methyl)amino]propyl, [N-(cyanomethyl)-N-(methyl)amino]propyl, [N-methyl-N-(phenylethyl)amino]propyl, [N-ethyl-N-(hydroxyethyl)amino]propyl, (3,4-dihydro-2(1H)-isoquinolinyl)propyl, N-methyl-piperidyl, (N,N-dimethylamino)propyl, piperidyl, aminopropyl or cyanomethyl, more preferably, H, ethyl, n-butyl, n-hexyl, 5-iodopentyl, carbamoylmethyl, 2-methylthioethyl, 2-(N,N-dimethylamino)ethyl, 2-morpholinoethyl, 4-(N,N-dimethylamino)butyl, 6-(N,N-dimethylamino)hexyl, 3-methansulfonylaminopropyl, 3-(N-ethyl-N- methylamino)propyl, 2-chloroethyl, 2-aminoethyl, 4-[(N,N-dimethylamino)methyl]phenyl, 3-(N,N-dimethylamino)-2-methylpropyl, 2-(1-methyl-2-piperidinyl)ethyl, 3-pyridylmethyl, 4-cyanobutyl, 4-(1H-benzimidazol-2-ylmethyl), 3-(N-methylamino) propyl, 2-(1-methyl-2-pyrrolidinyl)ethyl, 3-(1-azetidinyl)propyl, 3-{N-methyl-N-[2-(2-pyridinyl)ethyl]amino}propyl, 3-(N,N-diethylamino)propyl, 3-[N-isopropyl-N-(methyl)amino]propyl, 3-[N-(2-hydroxyethyl)-N-(isopropyl)amino]propyl, 3-[N,N-bis(2-hydroxyethyl)amino]propyl, 3-[N-(2-hydroxyethyl)-N-(methyl)amino]propyl, 3-[N-ethyl-N-(propyl)amino]propyl, 3-(4-methyl-1,4-diazepan-1-yl)propyl, 3-[N-hexyl-N-(methyl)amino]propyl, 3-(N-cyanomethyl-N-propyl)aminopropyl, 3-[N-[2-(N',N'-diethylamino)ethyl]-N-(methyl)amino]propyl, 3-[(N-cyanomethyl-N-methyl)amino]propyl, 3-[N-methyl-N-(2-phenylethyl)amino]propyl, 3-[N-ethyl-N-(2-hydroxyethyl)amino]propyl, 3-(3,4-dihydro-2(1H)-isoquinolinyl)propyl, N-methyl-4-piperidyl, 3-(N,N-dimethylamino)propyl, 4-piperidyl, 3-aminopropyl, cyanomethyl or 2-benzimidazolylmethyl, more preferably H, N-methyl-4-piperidyl, 3-N,N-dimethylpropyl, 4-piperidyl, 3-aminopropyl, cyanomethyl or 2-benzimidazolylmethyl, and most preferably H.

In the compounds of formula (I), $Y^1$, $Y^2$, $Y^3$ and $Y^4$ are preferably independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$-, $Q^2$-, $R^6(R^7)N$—, cyano, hydroxy and $R^6(R^7)NC(=O)$—, wherein $R^6$ and $R^7$ are independently selected from H and $C_{1-3}$alkyl; $R^8$ is aryl; $Q^1$ is a 4–10 membered monocyclic or bicyclic aromatic, partially saturated or fully saturated ring optionally containing up to 2 heteroatoms selected from O and N, and is optionally substituted with halo, $C_{1-2}$ alkyl, hydroxy, amino, $R^6(R^7)N$ $C_{1-2}$alkyl- or $R^6(R^7)NC_{1-2}$alkyl-O—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$—$C_{1-2}$alkyl- or $R^6(R^7)N$—$C_{1-2}$alkyl-O—, $R^6(R^7)N(O=)C$— or $R^6O(O=)C$—, more preferably independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$, $Q^2$-, $R^6(R^7)N$—, cyano, hydroxy and $R^6(R^7)NC(=O)$—, wherein $R^6$ and $R^7$ are independently selected from H, methyl and ethyl; $R^8$ is phenyl; $Q^1$ is phenyl, piperidyl, morpholino, pyridyl, benzimidazolyl, pyrrolidinyl, azetidinyl, diazepanyl or tetrahydroisoquinolyl being optionally substituted with halo, $C_{1-2}$ alkyl, hydroxy, amino, $R^6(R^7)N$ $C_{1-2}$alkyl- or $R^6(R^7)N$ $C_{1-2}$alkyl-O—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$— $C_{1-2}$alkyl-, $R^6(R^7)N$—$C_{1-2}$ alkyl-O—, $R^6(R^7)N(O=)C$— or $R^6O(O=)C$—, and most preferably independently selected from H, fluoro, chloro, bromo, methyl, ethyl, iso-propyl, aminopropyl, methoxy, benzyl, aminobenzyl, hydroxybenzyl, chlorobenzyl, cyanobenzyl, methoxybenzyl, (N,N-dimethylaminoethoxy)benzyl, nitrobenzyl, aminomethylbenzyl, aminoethylbenzyl, carbamoylbenzyl, carboxybenzyl, anilino, benzoylamino, hydroxy(phenyl)methyl, phenyl, aminophenyl, hydroxyphenyl, cyanoethyl, pyridylmethyl and ethoxycarbonylethenyl.

$Y^1$ is more preferably H, methyl, ethyl, propyl, aminophenyl, hydroxyphenyl, methoxy, fluoro or chloro, more preferably H, ethyl, 4-aminophenyl, iso-propyl, 4-hydroxyphenyl, methoxy or fluoro, and most preferably H, ethyl or 4-aminophenyl.

$Y^2$ is more preferably hydrogen, methyl, ethyl, propyl, benzyl, chlorobenzyl, benzoylamino, hydroxybenzyl, methoxybenzyl, (N,N-dimethylaminoethoxy)benzyl, aminopropyl, anilino, nitrobenzyl, aminomethylbenzyl, (aminoethyl)benzyl, aminobenzyl, cyanobenzyl, hydroxy(phenyl)methyl, hydroxyphenyl, cyanoethyl, pyridylmethyl, carbamoylbenzyl, carboxybenzyl, ethoxycarbonylethenyl or fluoro, more preferably hydrogen, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl, 2-chlorobenzyl, methyl, 2-aminomethylbenzyl, 2-(2-aminoethyl)benzyl, 2-aminobenzyl, 2-methoxybenzyl, 3-aminobenzyl, 3-aminomethylbenzyl, 4-cyanobenzyl, hydroxy(phenyl)methyl, 2-hydroxyphenyl (3-hydroxyphenyl), 2-cyanoethyl, ethyl, 3-pyridylmethyl, 3-carbamoylbenzyl, 3-carboxybenzyl, ethoxycarbonylethenyl, 2-carbamoylbenzyl or fluoro, and most preferably H, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl or 2-chlorobenzyl.

$Y^3$ is more preferably hydrogen, ethyl, methyl, methoxy or fluoro, more preferably hydrogen, methoxy or fluoro, and most preferably H.

$Y^4$ is more preferably hydrogen, chloro, fluoro, bromo, methyl, ethyl, methoxy or phenyl, more preferably hydrogen, chloro, fluoro, bromo or ethyl, and most preferably H.

Preferred compounds of this invention are those of the formula (I) wherein $R^1$ is $C_{1-2}$ alkyl;

$R^2$ is H or amino;

$R^3$ is H, halo-$CH_2$—, $R^4(R^5)NCH_2$—, $R^6(R^7)NC(=O)CH_2$—, cyano-$CH_2$—, $Q^1CH_2$—, $(O=)CCH_2$—, $C_{2-6}$ alkyl or $Q^1$-, wherein said $C_{2-6}$ alkyl is optionally substituted with up to 3 substituents selected from halo, methyl, $R^4(R^5)N$, $C_{1-2}$ alkylsulfonylamino, $C_{1-2}$ alkylthio, $R^6(R^7)NC(=O)$—, cyano and $Q^1$- or $Q^1$-(O=)C—;

$R^4$ is H, $C_{1-6}$ alkyl, HO—$C_{1-2}$ alkyl, $Q^1$-, $Q^1$-$C_{1-3}$alkyl-, cyano-$C_{1-2}$alkyl- or $R^6(R^7)N$ $C_{1-2}$alkyl-;

$R^5$ is H, $C_{1-2}$alkyl, HO—$C_{1-2}$ alkyl or $Q^1$-;

$R^6$ and $R^7$ are independently selected from H and $C_{1-3}$ alkyl;

$R^8$ is aryl;

$Q^1$ is a 4–10 membered monocyclic or bicyclic aromatic, partially saturated or fully saturated ring optionally containing up to 2 heteroatoms selected from O and N, and is optionally substituted with halo, $C_{1-2}$ alkyl, hydroxy, amino, $R^6(R^7)N$ $C_{1-2}$alkyl- or $R^6(R^7)NC_{1-2}$alkyl-O—;

$Y^5$, $Y^6$, $Y^7$ and $Y^8$ are hydrogen;

$Y^1$, $Y^2$, $Y^3$ and $Y^4$ are independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$-, $Q^2$-, $R^6(R^7)N$—, cyano, hydroxy and $R^6(R^7)NC(=O)$—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$—$C_{1-2}$alkyl- or $R^6(R^7)N$—$C_{1-2}$alkyl-O—, $R^6(R^7)N(O=)C$— or $R^6O(O=)C$—.

Much preferred compounds of this invention are those of the formula (I) wherein $R^1$ is $C_{1-2}$ alkyl;

$R^2$ is H or amino;

$R^3$ is H, halo-$CH_2$—, $R^4(R^5)NCH_2$—, $R^6(R^7)NC(=O)CH_2$—, cyano-$CH_2$—, $Q^1CH_2$—, $Q^1$-(O=)$CCH_2$—, $C_{2-6}$ alkyl or $Q^1$-, wherein said $C_{2-6}$ alkyl is optionally substituted with up to 3 substituents selected from halo, methyl, $R^4(R^5)N$, $C_{1-2}$ alkylsulfonylamino, $C_{1-2}$ alkylthio, $R^6(R^7)NC(=O)$—, cyano, $Q^1$- and $Q^1$-(O=)C—;

$R^4$ is H, $C_{1-6}$ alkyl, HO—$C_{1-2}$ alkyl, phenyl-$C_{1-3}$alkyl-, pyridyl-$C_{1-3}$alkyl-, cyano-$C_{1-2}$alkyl- or $R^6(R^7)N$ $C_{1-2}$alkyl-;

$R^5$ is H, $C_{1-2}$alkyl, HO—$C_{1-2}$ alkyl or $Q^1$-;

$R^6$ and $R^7$ are independently selected from H, methyl or ethyl $R^8$ is phenyl;

$Q^1$ is phenyl, piperidyl, morpholino, pyridyl, benzimidazolyl, pyrrolidinyl, azetidinyl, diazepanyl or tetrahydroisoquinolyl being optionally substituted with halo, $C_{1-2}$ alkyl, hydroxy, amino, $R^6(R^7)N$ $C_{1-2}$alkyl- or $R^6(R^7)N$ $C_{1-2}$alkyl-O—;

$Y^5$, $Y^6$, $Y^7$ and $Y^8$ are hydrogen;

$Y^1$, $Y^2$, $Y^3$ and $Y^4$ are independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$, $Q^2$-, $R^6(R^7)N$—, cyano, hydroxy and $R^6(R^7)NC(=O)$—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$—$C_{1-2}$alkyl-, $R^6(R^7)N$—$C_{1-2}$alkyl-O—, $R^6(R^7)N(O=)C$— or $R^6O(O=)C$—.

Also, preferred compounds of this invention are those of the formula (I) wherein $R^1$ is methyl $R^2$ is H or amino;

$R^3$ is hydrogen, ethyl, butyl, hexyl, iodopentyl, carbamoylmethyl, methylthioethyl, (N,N-dimethylamino)ethyl, morpholinoethyl, (N,N-dimethylamino)butyl, (N,N-dimethylamino)hexyl, methansulfonylaminopropyl, (N-ethyl-N-methylamino)propyl, chloroethyl, aminoethyl, [(N,N-dimethylamino)methyl]phenyl, (N,N-dimethylamino)(methyl)propyl, (1-methyl-2-piperidinyl)ethyl, pyridylmethyl, cyanobutyl, 2-benzimidazolylmethyl, (N-methylamino)propyl, (1-methyl-2-pyrrolidinyl)ethyl, (1-azetidinyl)propyl, {N-methyl-N-[(pyridinyl)ethyl]amino}propyl, (N,N-diethylamino)propyl, [N-isopropyl-N-(methyl)aminopropyl, [N-(2-hydroxyethyl)-N-(isopropyl)amino]propyl, [N,N-bis (2-hydroxyethyl)amino]propyl, [N-(hydroxyethyl)-N-(methyl)amino]propyl, [N-ethyl-N-(propyl)aminopropyl, (4-methyl-1,4-diazepan-1-yl)propyl, [N-hexyl-N-(methyl)amino]propyl, [N-(cyanomethyl)-N-(propyl)amino]propyl, [N-[(diethylamino)ethyl]-N-(methyl)amino]propyl, [N-(cyanomethyl)-N-(methyl)amino]propyl, [N-methyl-N-(phenylethyl)amino] propyl, [N-ethyl-N-(hydroxyethyl)amino]propyl, (3,4-dihydro-2(1H)-isoquinolinyl)propyl, N-methyl-piperidyl, (N,N-dimethylamino)propyl, piperidyl, aminopropyl or cyanomethyl; and $Y^1$, $Y^2$, $Y^3$ and $Y^4$ are independently selected from H, fluoro, chloro, bromo, methyl, ethyl, iso-propyl, aminopropyl, methoxy, benzyl, aminobenzyl, hydroxybenzyl, chlorobenzyl, cyanobenzyl, methoxybenzyl, (N,N-dimethylaminoethoxy)benzyl, nitrobenzyl, aminomethylbenzyl, aminoethylbenzyl, carbamoylbenzyl, carboxybenzyl, anilino, benzoylamino, hydroxy(phenyl)methyl, phenyl, aminophenyl, hydroxyphenyl, cyanoethyl, pyridylmethyl and ethoxycarbonylethenyl.

Also, preferred compounds of this invention are those of the formula (I) wherein $R^1$ is methyl;

$R^2$ is H or amino;

$R^3$ is H, ethyl, n-butyl, n-hexyl, 5-iodopentyl, carbamoylmethyl, 2-methylthioethyl, 2-(N,N-dimethylamino)ethyl, 2-morpholinoethyl, 4-(N,N-dimethylamino)butyl, 6-(N,N-dimethylamino)hexyl, 3-methansulfonylaminopropyl, 3-(N-ethyl-N-methylamino)propyl, 2-chloroethyl, 2-aminoethyl, 4-[(N,N-dimethylamino)methyl]phenyl, 3-(N,N-dimethylamino)-2-methylpropyl, 2-(1-methyl-2-piperidinyl)ethyl, 3-pyridylmethyl, 4-cyanobutyl, 4-(1H-benzimidazol-2-ylmethyl), 3-(N-methylamino) propyl, 2-(1-methyl-2-pyrrolidinyl)ethyl, 3-(1-azetidinyl)propyl, 3-{N-methyl-N-[2-(2-pyridinyl)ethyl]amino}propyl, 3-(N,N-diethylamino)propyl, 3-[N-isopropyl-N-(methyl)amino]propyl, 3-[N-(2-hydroxyethyl)-N-(isopropyl)amino]propyl, 3-[N,N-bis(2-hydroxyethyl)amino]propyl, 3-[N-(2-hydroxyethyl)-N-(methyl)amino]propyl, 3-[N-ethyl-N-(propyl)amino]propyl, 3-(4-methyl-1,4-diazepan-1-yl) propyl, 3-[N-hexyl-N-(methyl)amino]propyl, 3-(N-cyanomethyl-N-propyl)aminopropyl, 3-[N-[2-(N',N'-diethylamino)ethyl]-N-(methyl)amino]propyl, 3-[(N-cyanomethyl-N-methyl)amino]propyl, 3-[N-methyl-N-(2-phenylethyl)amino]propyl, 3-[N-ethyl-N-(2-hydroxyethyl)amino]propyl, 3-(3,4-dihydro-2(1H)-isoquinolinyl)propyl, N-methyl-4-piperidyl, 3-(N,N-dimethylamino)propyl, 4-piperidyl, 3-aminopropyl, cyanomethyl or 2-benzimidazolylmethyl;

$Y^1$ is H, methyl, ethyl, propyl, aminophenyl, hydroxyphenyl, methoxy, fluoro or chloro;

$Y^2$ is hydrogen, methyl, ethyl, propyl, benzyl, chlorobenzyl, benzoylamino, hydroxybenzyl, methoxybenzyl, (N,N-dimethylaminoethoxy)benzyl, aminopropyl, anilino, nitrobenzyl, aminomethylbenzyl, (aminoethyl)benzyl, aminobenzyl, cyanobenzyl, hydroxy(phenyl)methyl, hydroxyphenyl, cyanoethyl, pyridylmethyl, carbamoylbenzyl, carboxybenzyl, ethoxycarbonylethenyl or fluoro;

$Y^3$ is hydrogen, ethyl, methyl, methoxy or fluoro; and $Y^4$ is hydrogen, chloro, fluoro, bromo, methyl, ethyl, methoxy or phenyl.

Also, preferred compounds of this invention are those of the formula (I) wherein $R^1$ is methyl;

$R^2$ is H;

$R^3$ is H, N-methyl-4-piperidyl, 3-N,N-dimethylpropyl, 4-piperidyl, 3-aminopropyl, cyanomethyl or 2-benzimidazolylmethyl;

$Y^1$ is H, ethyl, 4-aminophenyl, iso-propyl, 4-hydroxyphenyl, methoxy or fluoro;

$Y^2$ is hydrogen, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl, 2-chlorobenzyl, methyl, 2-aminomethylbenzyl, 2-(2-aminoethyl)benzyl, 2-aminobenzyl, 2-methoxybenzyl, 3-aminobenzyl, 3-aminomethylbenzyl, 4-cyanobenzyl, hydroxy(phenyl)methyl, 2-hydroxyphenyl (3-hydroxyphenyl, 2-cyanoethyl, ethyl, 3-pyridylmethyl, 3-carbamoylbenzyl, 3-carboxybenzyl, ethoxycarbonylethenyl, 2-carbamoylbenzyl or fluoro;

$Y^3$ is hydrogen, methoxy or fluoro; and $Y^4$ is hydrogen, chloro, fluoro, bromo or ethyl.

Also, preferred compounds of this invention are those of the formula (I) wherein the dashed lines represent double bonds $R^1$ is methyl;

$R^2$ is H;

$R^3$ is H;

$Y^1$ is H, ethyl or 4-aminophenyl;

$Y^2$ is H, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl or 2-chlorobenzyl;

$Y^3$ is H;

$Y^4$ is H; and $Y^5$, $Y^6$, $Y^7$ and $Y^8$ are absence.

Preferred individual compounds of this invention are:
7-(4-chlorobenzyl)-1-methyl-1,4-dihydro-9H-pyrazolo[4,3-b]quinolin-9-one;

N-(1-methyl-9-oxo-4,9-dihydro-1H-pyrazolo[4,3-b]quinolin-7-yl)benzamide;

7-(3-chlorobenzyl)-1-methyl-1,4-dihydro-9H-pyrazolo[4,3-b]quinolin-9-one;

sodium 2-[[1-methyl-1,4-dihydro-9H-pyrazolo[4,3-b]quinolin-9-one]-7-yl-methyl]phenoxide;

7-(3-hydroxybenzyl)-1-methyl-1,4-dihydro-9H-pyrazolo[4,3-b]quinolin-9-one;

7-(4-methoxybenzyl)-1-methyl-1,4-dihydro-9H-pyrazolo[4,3-b]quinolin-9-one;

8-ethyl-1-methyl-1,4-dihydro-9H-pyrazolo[4,3-b]quinolin-9-one;

7-benzyl-1-methyl-1,4-dihydro-9H-pyrazolo[4,3-b]quinolin-9-one;

8-(4-aminophenyl)-1-methyl-1,4-dihydro-9H-pyrazolo[4,3-b]quinolin-9-one hydrochloride;

7-(3-aminopropyl)-1-methyl-1,4-dihydro-9H-pyrazolo[4,3-b]-quinolin-9-one hydrochloride;

7-anilino-1-methyl-1,4-dihydro-9H-pyrazolo[4,3-b]-quinolin-9-one;

1-methyl-7-(3-nitrobenzyl)-1,4-dihydro-9H-pyrazolo[4,3-b]quinolin-9-one;

7-(3-methoxybenzyl)-1-methyl-1,4-dihydro-9H-pyrazolo[4,3-b]quinolin-9-one;

7-(2-chlorobenzyl)-1-methyl-1,4-dihydro-9H-pyrazolo[4,3-b]quinolin-9-one;

7-[2-(aminomethyl)benzyl]-1-methyl-1,4-dihydro-9h-pyrazolo[4,3-b]quinolin-9-one hydrochloride; and 7-[2-(2-aminoethyl)benzyl]-1-methyl-1,4-dihydro-9h-pyrazolo[4,3-b]quinolin-9-one hydrochloride;

and salts thereof.

Most preferred individual compounds of this invention are: 7-(4-chlorobenzyl)-1-methyl-1,4-dihydro-9H-pyrazolo[4,3-b]quinolin-9-one;

N-(1-methyl-9-oxo-4,9-dihydro-1H-pyrazolo[4,3-b]quinolin-7-yl)benzamide;

7-(3-chlorobenzyl)-1-methyl-1,4-dihydro-9H-pyrazolo[4,3-b]quinolin-9-one;

sodium 2-[[1-methyl-1,4-dihydro-9H-pyrazolo[4,3-b]quinolin-9-one]-7-yl-methyl]phenoxide;

7-(3-hydroxybenzyl)-1-methyl-1,4-dihydro-9H-pyrazolo[4,3-b]quinolin-9-one;

7-(4-methoxybenzyl)-1-methyl-1,4-dihydro-9H-pyrazolo[4,3-b]quinolin-9-one;

8-ethyl-1-methyl-1,4-dihydro-9H-pyrazolo[4,3-b]quinolin-9-one; and 7-benzyl-1-methyl-1,4-dihydro-9H-pyrazolo[4,3-b]quinolin-9-one;

and salts thereof.

General Synthesis

The following reaction Schemes illustrate the preparation of the compounds of the present invention. Unless otherwise indicated, $C^1$ to $C^4$, $Y^1$ to $Y^8$, $R^1$ to $R^8$, $Q^1$ and $Q^2$ in the reaction Schemes and discussion that follow are defined herein before.

The pyrazoloquinolinone compounds of Formula (I) of this invention may be prepared by a variety of synthetic methods known to those skilled in the art.

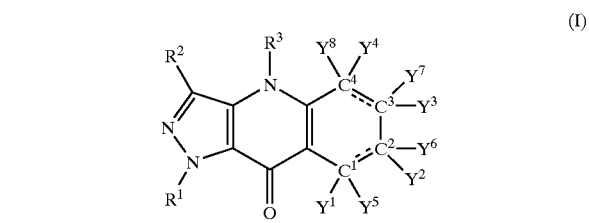

(I)

In a desired reaction step of the processes described hereafter, hydroxy or amino groups protection and removal of the hydroxy or amino protecting groups with reactants and reagents used may be carried out according to known procedures such as those described in Protective Groups in Organic Synthesis edited by T. W. Greene et al. (John Wiley & Sons, 1991). Typical hydroxy or amino protecting groups include benzyl, $C_2H_5OC(=O)$—, benzyloxycarbonyl represented as Z and t-But-O—C(=O)— represented as t-Boc or Boc.

Reaction Scheme 1 illustrates a method for the preparation of the compound of formula (I) wherein $R^3$ is H, $Y^5$ to $Y^8$ are absent and the dashed lines represent double bond. (hereinafter represented by Formula (Ia)).

Scheme 1

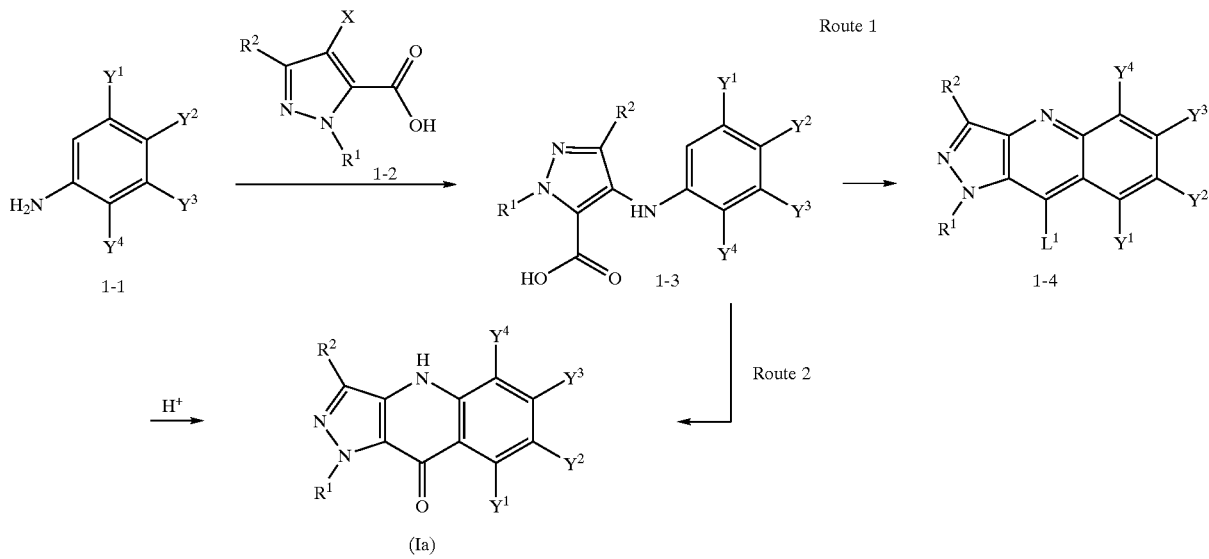

Compound (Ia) may be prepared through a process(Route 1) comprising:
(a) a coupling reaction of a compound of formula 1-1 with a pyrazolecarboxlic acid derivative 1-2 wherein X is a leaving group such as halo, mesylate(OMs) or tosylate (OTs) to give a compound of formula 1-3;
(b) cyclization of the resulting anilinopyrazole compound of formula 1-3 in the presence of a cyclizing reagent to give a tricyclic compound of formula 1-4 wherein $L^1$ is halogen; and
(c) hydrolysis of the compound of formula 1-4 under the acidic condition to give a pyrazoloquinolinone compound of formula (Ia).

Each reaction step is described more specifically as follows:
(a) Coupling: The coupling reaction (a) may be carried out in the absence of, or presence of a base in a reaction inert solvent or without solvent. Preferred bases include, for example, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride; and an amine such as triethylamine, tributylamine, diisopropylethylamine, 2,6-lutidine, pyridine or dimethylaminopyridine. Preferred reaction inert solvents include, but are not limited to, water, benzene, toluene, xylene, o-dichlorobenzene, nitrobenzene, pyridine, tetrahydrofuran, dimethylformamide (DMF), 1,4-dioxane, dimethylsulfoxide (DMSO) and mixtures thereof. Preferably, the reaction is conducted in the presence of a metal catalyst. Preferred metal catalysts include, for example, copper and nickel. Reaction temperatures are generally in the range of −100 to 250° C., preferably in the range of 50 to 150° C., but if necessary, lower or higher temperature can be employed. Reaction times are, in general, from 1 minute to a day, preferably from 20 minutes to 5 hours, however shorter or longer reaction times, if necessary, can be employed.
(b) Cyclization: The compound of formula 1-3 may be cyclized to form a tricyclic compound by any synthetic procedure applicable to structure-related compounds known to those skilled in the art (for example, see Author *Chem. Heterocycl. Compd(Engl. Transl.)*, 1984; pp918 and ibid., 1985, pp905). When $L^1$ is Cl, a suitable cyclizing reagent is, for example, phosphoryl chloride, thionyl chloride or oxalyl chloride. The reaction may be carried out at a temperature in the range from of 0° C. to 250° C., preferably in the range of 50° C. to 100° C., but if necessary, lower or higher temperature can be employed. Reaction times are, in general, from 1 minute to a few days, preferably from 30 minutes to 48 hours, however shorter or longer reaction times, if necessary, can be employed. The reaction may be carried out in a reaction inert solvent, such as dichloroethane.
(c) Hydrolysis: The hydrolysis of the compound of formula 1-4 may be carried out by conventional procedures. The hydrolysis may be carried out by treatment with acid in the presence or absence of a reaction inert solvent. Preferred acids include, for example, acetic acid, hydrochloric acid, trifluoroacetic acid or sulfuric acid. Preferred reaction inert solvents include, for example, water, aqueous tetrahydrofuran(THF), aqueous DMF or the mixture of them. Reaction temperatures are generally in the range of 0° C. to 200° C., preferably in the range of 50° C. to the 150° C., but if necessary, lower or higher temperature can be employed. Reaction times are, in general, from 1 minute to a day, preferably from 20 minutes to 5 hours, however shorter or longer reaction times, if necessary, can be employed.

Alternatively, the compound of formula (Ia) may be prepared from the compound of formula (1-3) directly (Route 2 in Scheme 1). The compound of formula 1-3 may be treated with a condensing agent to give a pyrazoloquinolinone compound of Formula (Ia). Condensing agents include, for example, polyphosphoric acid, Lewis acids and proton acids. Suitable condensing agents include, for example, polyphosphoric acid, aluminum chloride or sulfuric acid. The condensation may be carried out in the presence or absence of a reaction inert solvent. In the absence of a reaction inert solvent, reaction temperatures are generally in the range of 0° C. to 200° C., preferably in the range of 50° C. to the 150° C., but if necessary, lower or higher temperature can be employed. In the presence of a reaction inert solvent, preferred reaction inert solvents include, dichloromethane, dichloroethane or nitrobenzene. Reaction temperatures are generally in the range of 0° C. to reflux temperature, preferably in the range of 0° C. to the 100° C., but if necessary, lower or higher temperature can be employed. Reaction times are, in general, from 1 minute to a day, preferably from 20 minutes to 5 hours, however shorter or longer reaction times, if necessary, can be employed.

The compound of formula Ia may also be prepared by a method as shown in Scheme 2.

of a reaction inert solvent. Preferred reaction inert solvents include, for example, THF, dialkylether and mixtures thereof. Reaction temperatures are generally in the range of −120° C. to 150° C., preferably in the range of −100° C. to 50° C., but if necessary, lower or higher temperature can be employed. Reaction times are, in general, from 1 minute to a day, preferably from 20 minutes to 5 hours, however shorter or longer reaction times, if necessary, can be employed.

Then, the resulting carbanion may be treated with an acylhalide compound of formula 2—2 to provide a compound of formula 2-3.

(b) Reduction: Then the resulting compound of formula 2-3 may be subjected to reduction to give the com-

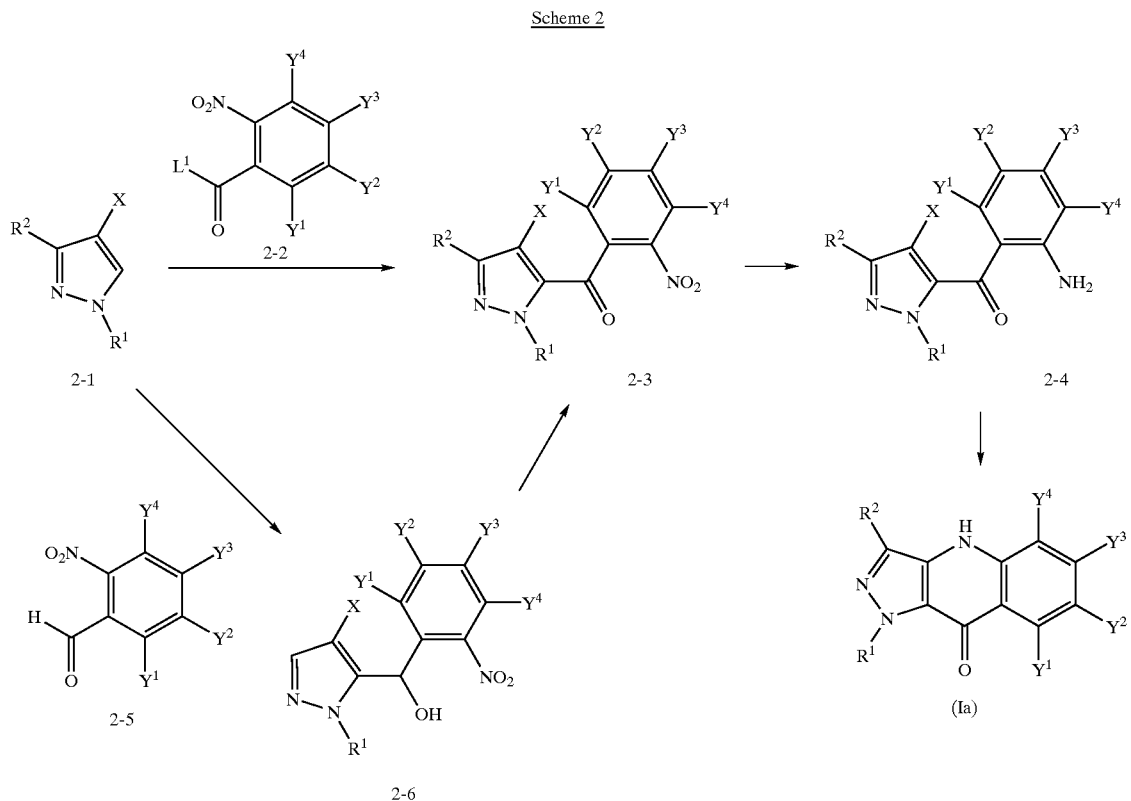

Scheme 2

Compound (Ia) may be prepared through a process comprising:
(a) acylation of a compound of formula 2-1 with a benzoyl halide derivative 2—2 wherein X is halo, such as chloro or bromo to give a compound of formula 2-3;
(b) reduction of the nitro group in the compound of formula 2-3 to give a anilino compound of formula 2-4; and
(c) cyclization of the resulting benzoylpyrazole compound of formula 2-4 in the presence of a metal catalyst to give a tricyclic compound of formula (Ia).

Each reaction step is described more specifically as follows:
(a) Acylation: Firstly, the compound of the formula 2-1 may be treated with a base to obtain a carbanion. Preferred bases include, for example, alkyllithium, aryllithium and lithium diisopropylamide(LDA). More preferred bases may be lithium diisopropylamide. The treatment with a base may be carried out in the presence pound of formula 2-4. The reduction may be carried out in the presence of a suitable reducing agent in a reaction inert solvent or without solvent. Preferred reducing agents include, for example, Fe, Sn or Zn. When a reducing reagent is Fe, Sn or Zn, if desired, the reaction is carried out under acidic conditions in the presence of water. Preferred reaction inert solvents include, for example, methanol, ethanol, diglyme, benzene, toluene, xylene, o-dichlorobenzene, dichloromethane, 1,2-dichloroethane, tetrahydrofuran, 1,4-dioxane, and mixtures thereof. Reaction temperatures are generally in the range of −100 to 250° C., preferably in the range of 0° C. to reflux temperature, but if necessary, lower or higher temperature can be employed. Reaction times are, in general, from 1 minute to a day, preferably from 20 minutes to 5 hours, however shorter or longer reaction times, if necessary, can be employed. The reduction may also be carried out under known hydrogenation conditions in the presence of a metal catalyst under hydrogen atmosphere or in the presence of hydrogen sources such as hydrazine or formic acid. If desired, the reaction is carried out under acidic conditions, for example, in the presence of hydrochloric acid or acetic acid. Preferred metal catalysts include, for example, nickel catalysts such as Raney nickel, palladium catalysts such as Pd—C, platinum catalysts such as $PtO_2$, or ruthenium catalysts such as $RuCl_2(Ph_3P)_3$. Preferred reaction inert solvents include, for example, methanol, ethanol, ethyl acetate, THF or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to a day, preferably from 20 minutes to 5 hours, however shorter or longer reaction times, if necessary, can be employed.

(c) Cyclization: The compound of formula 2-4 may be cyclized to form pyrazoloquinolinone by treating the compound of formula 2-4 with a base in the presence of metal catalyst. Preferred bases include, for example, an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, 2,6-lutidine, pyridine or dimethylaminopyridine. Preferred metal catalysts include, for example, copper and nickel. The reaction may be carried out in a reaction inert solvent. Suitable reaction inert solvents include, for example, benzene, toluene, xylene, o-dichlorobenzene, nitrobenzene, dichloromethane, 1,2-dichloroethane, tetrahydrofuran (THF), dimethylformamide (DMF), 1,4-dioxane, dimethylsulfoxide (DMSO) or mixtures thereof. The reaction may be carried out at a temperature in the range of from 0 to 250° C., preferably in the range of 50 to 200° C., but if necessary, lower or higher temperature can be employed. Reaction times are, in general, from 1 minute to a few days, preferably from 30 minutes to 48 hours, however shorter or longer reaction times, if necessary, can be employed.

As depicted in Scheme 2—2, the intermediate compound of formula 2-3 may be prepared by an alternative route.

Scheme 2-2

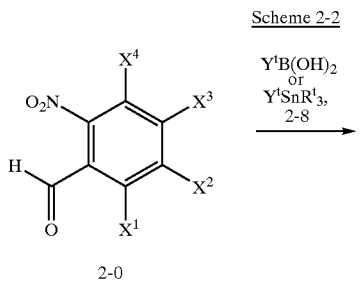

2-0

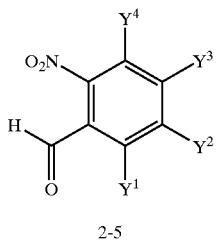

2-5

After treating a pyrazole compound of formula 2—2 with a base, the anion obtained may be reacted with a benzaldehyde compound of formula 2-5 instead of the acylhalide compound of formula 2—2 to give a alcohol compound of formula 2-6. This compound may be subjected to oxidation to give the compound of formula 2-3. The oxidation may be carried out in the presence of or absence of a suitable oxidizing agent in a reaction inert solvent or without solvent. Preferred oxidizing agents include, for example, manganese oxide, chromium oxide and 2,3-dichloro-5,6-dicyano-1,4-benzoquinone (DDQ). Preferred reaction inert solvents include, for example, acetone, dimethylsulfoxide(DMSO), acetic anhydride, tetrahydrofuran, 1,4-dioxane or mixtures thereof. Reaction temperatures are generally in the range of 0° C. to reflux temperature, preferably in the range of 20° C. to reflux temperature, but if necessary, lower or higher temperature can be employed. Reaction times are, in general, from 1 minute to 3 days, preferably from 20 minutes to 2 days, however shorter or longer reaction times, if necessary, can be employed.

The intermediate benzaldehyde compound of formula 2-5 may be prepared from a compound of formula 2-0, wherein $X^1$, $X^2$, $X^3$ and $X^4$ are independently selected from H, Br or O-trifluoromethanesulfonate(OTf), by a coupling reaction using an appropriate coupling reagent of formula 2-8, wherein $R^t$ is $C_{1-5}$ alkyl and $Y^t$ is independently selected from $Y^1, Y^2, Y^3$ and $Y^4$, in the presence of catalysts. Suitable coupling reagents include aryl or heteroaryltrialkylstannane, aryl or heteroarylboronic acid, or arylalkyl or heteroarylalkyltrialkylstannane. Suitable catalysts include, for example, tetrakis(triphenylphosphine)palladium or dichlorobis(triphenylphosphine)palladium. The reaction may be carried out in a reaction inert solvent or without solvent. Suitable reaction inert solvents include, for example, hexamethylphosphoramide(HMPA) or dimethoxyethane (DME). Reaction temperatures are generally in the range of 0° C. to 250° C., preferably in the range of 20° C. to 150° C., but if necessary, lower or higher temperature can be employed. Reaction times are, in general, from 1 minute to 2 days, preferably from 20 minutes to a day, however shorter or longer reaction times, if necessary, can be employed.

The compound of formula (Ia) also may be prepared from the compound of formula 3-1 through the compound of formula 1-4 as shown in Scheme 3.

Scheme 3

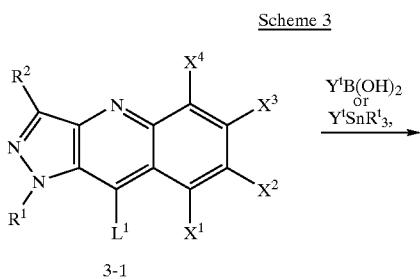

3-1

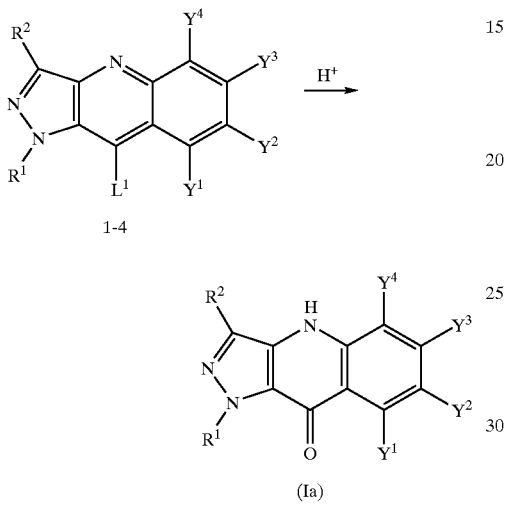

The compound of formula 3-1 may be reacted with aryl or heteroaryltrialkylstannane, aryl or heteroarylboronic acid, or arylalkyl or heteroarylalkyltrialkylstannane in the presence of catalysts to give the compound of formula 1-4. Suitable coupling reagents include aryl or heteroaryltrialkylstannane, aryl or heteroarylboronic acid, or arylalkyl or heteroarylalkyltrialkylstannane. Suitable catalysts include, for example, tetrakis(triphenylphosphine)palladium or dichlorobis(triphenylphosphine)palladium. If desired, the reaction may be carried out in the presence of a base, such as sodium bicarbonate, sodium carbonate, potassium carbonate and the like. The reaction may be carried out in a reaction inert solvent or without solvent. Suitable reaction inert solvents include, for example, hexamethylphosphoramide(HMPA) or dimethoxyethane(DME). Reaction temperatures are generally in the range of 0° C. to 250° C., preferably in the range of 20° C. to 150° C., but if necessary, lower or higher temperature can be employed. Reaction times are, in general, from 1 minute to 2 days, preferably from 20 minutes to a day, however shorter or longer reaction times, if necessary, can be employed. The obtained chlorinated compound of formula 1-4 may be hydrolyzed under the acidic conditions to give the compound of formula Ia. Suitable acids include, for example, acetic acid, hydrochloric acid, trifluoroacetic acid or sulfuric acid. Preferred reaction inert solvents include, for example, water, aqueous tetrahydrofuran(THF), aqueous DMF or the mixture of them. Reaction temperatures are generally in the range of 0° C. to 200° C., preferably in the range of 50° C. to the 150° C., but if necessary, lower or higher temperature can be employed. Reaction times are, in general, from 1 minute to a day, preferably from 20 minutes to 5 hours, however shorter or longer reaction times, if necessary, can be employed.

Reaction Scheme 4 illustrates a method for the preparation of the compound of formula (Ia) wherein at least one of $Y^1$, $Y^2$, $Y^3$ and $Y^4$ is —$(CH_2)_n$PhOH and n is 0 to 4 (hereinafter represented by Formula (Ia$^2$)). The compound of formula (Ia) wherein at least one of $Y^1$, $Y^2$, $Y^3$ and $Y^4$ is —$(CH_2)_n$PhOC$_{1-4}$alkyl(hereinafter represented by Formula (Ia$^1$)) may be prepared according to the same procedure as mentioned before.

Scheme 4

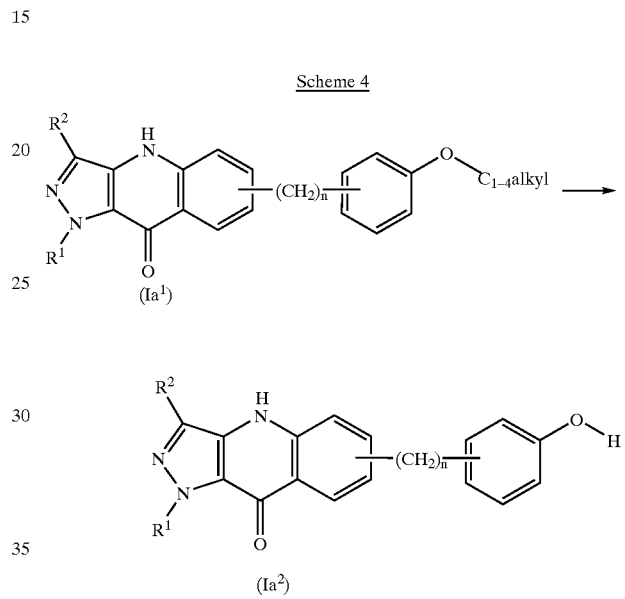

The compound of formula Ia$^1$ may be dealkylated under the standard conditions to give the compound of formula Ia$^2$. Dealkylation of the compound of formula Ia$^1$ may be carried out according to a number of standard procedures known to those skilled in the art (e.g., "Protection for Phenols", in *Protective Groups in Organic Synthesis,* 3rd Edition, T. W. Greene and P. G. M. Wuts, Ed., John Wiley and Sons, Inc. 1991, pp. 246–275). For example, the compound of formula Ia$^1$ may be treated with a proton and/or Lewis acid such as hydrogen bromide or aluminum chloride in a suitable solvent such as water, acetic acid or dichloromethane. Reaction temperatures are generally in the range of −100° C. to 250° C., preferably in the range of 0° C. to 200° C., but if necessary, lower or higher temperature can be employed. Reaction times are, in general, from 1 minute to a day, preferably from 20 minutes to 5 hours, however shorter or longer reaction times, if necessary, can be employed.

Reaction Scheme 5 illustrates a method for the preparation of the compound of formula (Ia) wherein at least one of $Y^1$, $Y^2$, $Y^3$ and $Y^4$ is —$(CH_2)_n$Ph$(CH_2)_n$NH$_2$(hereinafter represented by Formula (Ia$^4$)). The compound of formula (Ia) wherein at least one of $Y^1$, $Y^2$, $Y^3$ and $Y^4$ is —$(CH_2)_n$Ph$(CH_2)_n$—N-phthalimidolyl (hereinafter represented by Formula (Ia$^3$)) may be prepared according to the same procedure as mentioned before.

Scheme 5

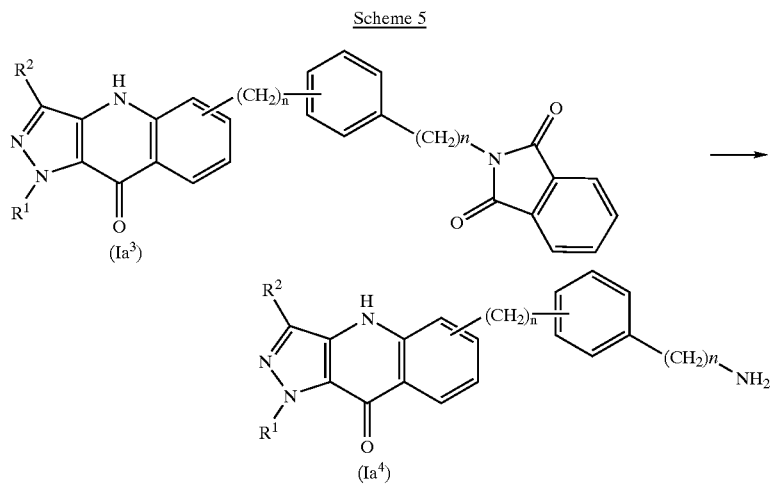

Cleavage of N-phthalimide in the compound of formula Ia³ may be carried out according to a number of standard procedures known to those skilled in the art (e.g., "Protection for the amino group", in *Protective Groups in Organic Synthesis,* 3rd Edition, T. W. Greene and P. G. M. Wuts, Ed., John Wiley and Sons, Inc. 1991, pp. 564–566). For example, the compound of formula Ia³ may be treated with a hydrazine derivative, such as hydrazine, methylhydrazine, and phenylhydrazine in a suitable solvent such as water or ethanol. Reaction temperatures are generally in the range of −50° C. to 200° C., preferably in the range of 0° C. to 150° C., but if necessary, lower or higher temperature can be employed. Reaction times are, in general, from 1 minute to 2 days, preferably from 20 minutes to 1 day, however shorter or longer reaction times, if necessary, can be employed.

Reaction Scheme 6 illustrates a method for the preparation of the compound of formula (Ia) wherein at least one of $Y^1$, $Y^2$, $Y^3$ and $Y^4$ is —$(CH_2)_n Q'NH_2$ ($Q'$ is aryl or heteroaryl, hereinafter represented by Formula (Ia⁶)). The compound of formula (Ia) wherein at least one of $Y^1$, $Y^2$, $Y^3$ and $Y^4$ is —$(CH_2)_n Q'NO_2$ (hereinafter represented by Formula (Ia⁴)) may be prepared according to the same procedure as mentioned before.

Scheme 6

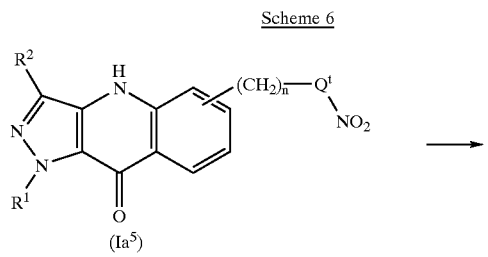

-continued

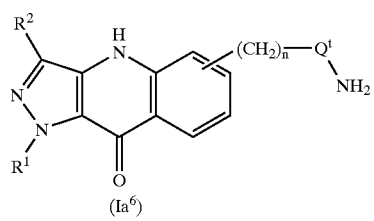

The reduction may be carried out in the presence of a suitable reducing agent in a reaction inert solvent or without solvent. A preferred reducing agent is selected from, for example, $LiAlH_4$, $LiBH_4$, Fe, Sn or Zn. When a reducing reagent is Fe, Sn or Zn, if desired, the reaction is carried out in the presence of ammonium chloride. Preferred reaction inert solvents include, for example, water, methanol, ethanol, diglyme, benzene, toluene, xylene, o-dichlorobenzene, dichloromethane, 1,2-dichloroethane, tetrahydrofuran, 1,4-dioxane, or mixtures thereof. Reaction temperatures are generally in the range of −100 to 250° C., preferably in the range of 0 to 150° C., but if necessary, lower or higher temperature can be employed. Reaction times are, in general, from 1 minute to a day, preferably from 20 minutes to 12 hours, however shorter or longer reaction times, if necessary, can be employed.

Reaction Scheme 7 illustrates a method for the preparation of the compound of formula (Ia) wherein at least one of $Y^1$, $Y^2$, $Y^3$ and $Y^4$ is —$(CH_2)_n Ph(CH_2)_m CONH_2$ and m is 0 to 3 (hereinafter represented by Formula (Ia⁸)), —$(CH_2)_n Ph(CH_2)_m CO_2 H$ (hereinafter represented by Formula (Ia⁹)) or —$(CH_2)_n Ph(CH_2)_m CH_2 NH_2$ (hereinafter represented by Formula (Ia¹⁰)). The compound of formula (Ia) wherein at least one of $Y^1$, $Y^2$, $Y^3$ and $Y^4$ is —CN (hereinafter represented by Formula (Ia⁷)) may be prepared according to the same procedure as mentioned before.

Scheme 7

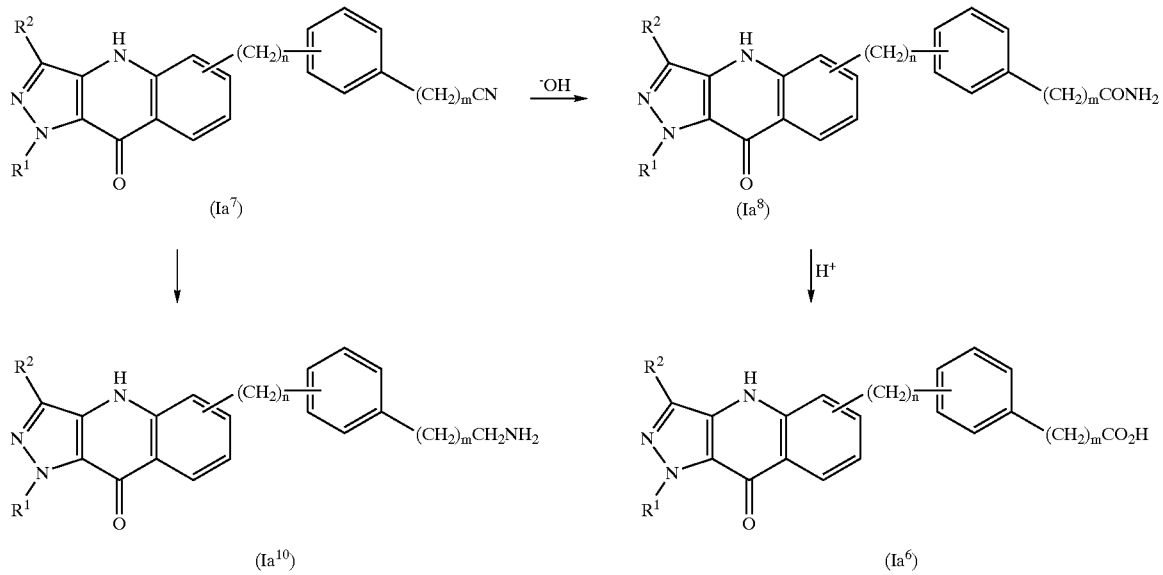

The hydrolysis of the compound of formula $Ia^7$ may be carried out by conventional procedures. The hydrolysis may be carried out by treatment with a base. Preferred bases include, for example, an alkali or alkaline earth metal hydroxide, alkoxide, carbonate, or halide, such as sodium hydroxide, potassium hydroxide, sodium methoxide, sodium ethoxide, potassium tert-butoxide, sodium carbonate, potassium carbonate or lithium iodide, in the presence or absence of a reaction inert solvent. Preferred reaction inert solvents include, for example, water, methanol, ethanol, isopropanol, tert-butylalcohol, tetrahydrofuran (THF), DMSO, benzene, toluene, xylene, o-dichlorobenzene, nitrobenzene, pyridine, dichloromethane, 1,2-dichloroethane, or mixtures thereof. Reaction temperatures are generally in the range of $-100°$ C. to $250°$ C., preferably in the range of $0°$ C. to $100°$ C., but if necessary, lower or higher temperature can be employed. Reaction times are, in general, from 1 minute to a day, preferably from 20 minutes to 12 hours, however shorter or longer reaction times, if necessary, can be employed.

The hydrolysis of the compound of formula $Ia^8$ may be carried out by conventional procedures. The hydrolysis may be carried out by treatment with an acid or an alkaline. Preferred acids include, for example, hydrochloric acid, acetic acid or sulfuric acid in the presence or absence of a reaction inert solvent. Preferred reaction inert solvents include, for example, water, methanol, ethanol, isopropanol, tert-butylalcohol, tetrahydrofuran (THF), DMSO, benzene, toluene, xylene, o-dichlorobenzene, nitrobenzene, pyridine, dichloromethane, 1,2-dichloroethane, or mixtures thereof. Reaction temperatures are generally in the range of $-100°$ C. to $250°$ C., preferably in the range of $0°$ C. to $150°$ C., but if necessary, lower or higher temperature can be employed. Reaction times are, in general, from 1 minute to 2 days, preferably from 20 minutes to 24 hours, however shorter or longer reaction times, if necessary, can be employed.

The reduction of the compound of formula $Ia^7$ may be carried out under known hydrogenation conditions in the presence of a metal catalyst under hydrogen atmosphere or in the presence of hydrogen sources such as hydrazine or formic acid. If desired, the reaction is carried out under basic conditions, for example, in the presence of ammonia. Preferred metal catalysts include, for example, nickel catalysts such as Raney nickel, palladium catalysts such as Pd—C, platinum catalysts such as $PtO_2$, or ruthenium catalysts such as $RuCl_2 (Ph_3P)_3$. Preferred reaction inert solvents include, for example, methanol, ethanol, ethyl acetate, THF, 1,4-dioxane or mixtures thereof. The reaction may be carried out at a temperature in the range from of $-100$ to $150°$ C., preferably in the range of $0°$ C. to $100°$ C., but if necessary, lower or higher temperature can be employed. Reaction times are, in general, from 1 minute to a day, preferably from 20 minutes to 12 hours, however shorter or longer reaction times, if necessary, can be employed.

Reaction Scheme 8 illustrates a method for the preparation of the compound of formula (Ia) wherein at least one of $Y^1$, $Y^2$, $Y^3$ and $Y^4$ is —$NHR^8$(hereinafter represented by Formula ($Ia^{11}$)). The compound of formula 8-1 may be prepared according to the same procedure as described in Scheme 1, 4 or 6.

Scheme 8

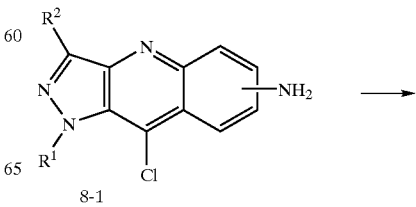

8-1

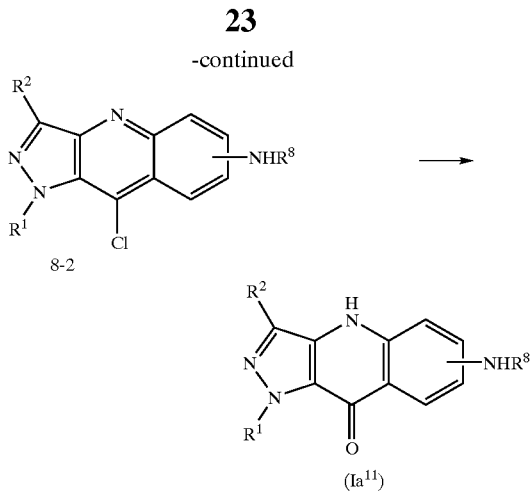

The obtained compound of formula 8-1 may be reacted with boronic acid derivative in the presence of catalysts to provide N-substituted compound of formula 8-2. Preferred catalysts include, for example, copper acetate or copper oxide. This reaction may be carried out in the absence or presence of a reaction inert solvent. Preferred reaction inert solvents include, for example, benzene, toluene, xylene, o-dichlorobenzene, nitrobenzene, pyridine, dichloromethane, 1,2-dichloroethane, tetrahydrofuran, 1,4-dioxane, N,N-dimethylformamide or mixtures thereof. If desired, the reaction may be carried out in the presence of base, such as triethyl amine, diisopropylethylamine, or N-methylmorpholine. Reaction temperatures are generally in the range of −100° C. to 250° C., preferably in the range of 0° C. to the reflux temperature, but if necessary, lower or higher temperature can be employed. Reaction times are, in general, from 1 minute to 2 days, preferably from 20 minutes to 24 hours, however shorter or longer reaction times, if necessary, can be employed. The hydrolysis of obtained compound of formula 8-2 may be carried out according to the conditions illustrated in Scheme 1 to give the compound of formula $Ia^{11}$.

Reaction Scheme 9 illustrates a method for the preparation of the compound of formula (Ia) wherein at least one of $Y^1$, $Y^2$, $Y^3$ and $Y^4$ is —NHCOQ$^1$(hereinafter represented by Formula ($Ia^{12}$)). The compound of formula 9-1(8-1) may be prepared according to the same procedure as described in Scheme 1, 4 or 6.

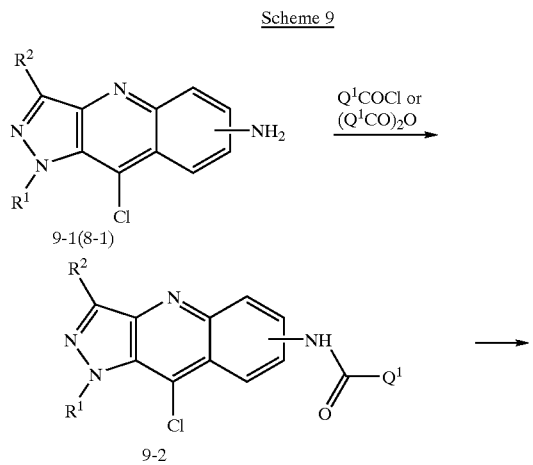

The obtained compound of formula 9-1(8-1) may be reacted with acylating agents, such as acid chloride or acid anhydride in the absence or presence of a reaction inert solvent. Preferred reaction inert solvents include, for example, pyridine, dichloromethane, 1,2-dichloroethane, or mixtures thereof. Reaction temperatures are generally in the range of −100° C. to 250° C., preferably in the range of 0° C. to the reflux temperature, but if necessary, lower or higher temperature can be employed. Reaction times are, in general, from 1 minute to 2 days, preferably from 20 minutes to 24 hours, however shorter or longer reaction times, if necessary, can be employed. The hydrolysis of obtained compound of formula 9-2 may be carried out according to the conditions illustrated in Scheme 1 to give the compound of formula $Ia^{12}$.

Reaction Scheme 10 illustrates a method for the preparation of the compound of formula (Ia) wherein at least one of $Y^1$, $Y^2$, $Y^3$ and $Y^4$ is —(CH$_2$)$_2$R$^{10}$(hereinafter represented by Formula ($Ia^{13}$)). The compound of formula 10-1, wherein X is halo or OTf, may be prepared according to the same procedure as described in Scheme 1, 4 or 6.

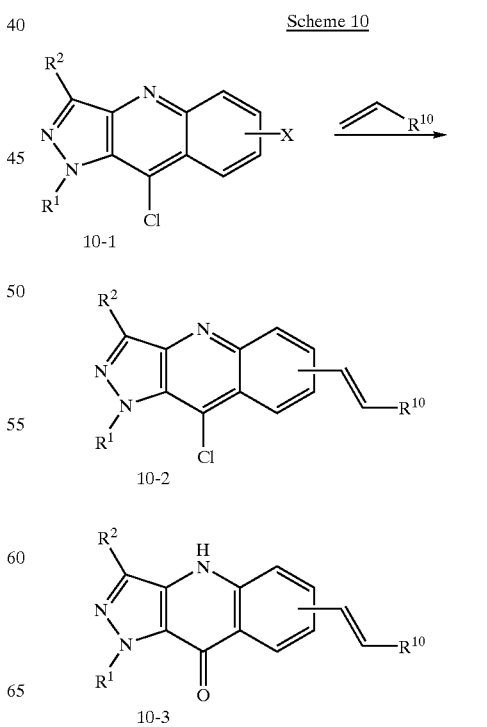

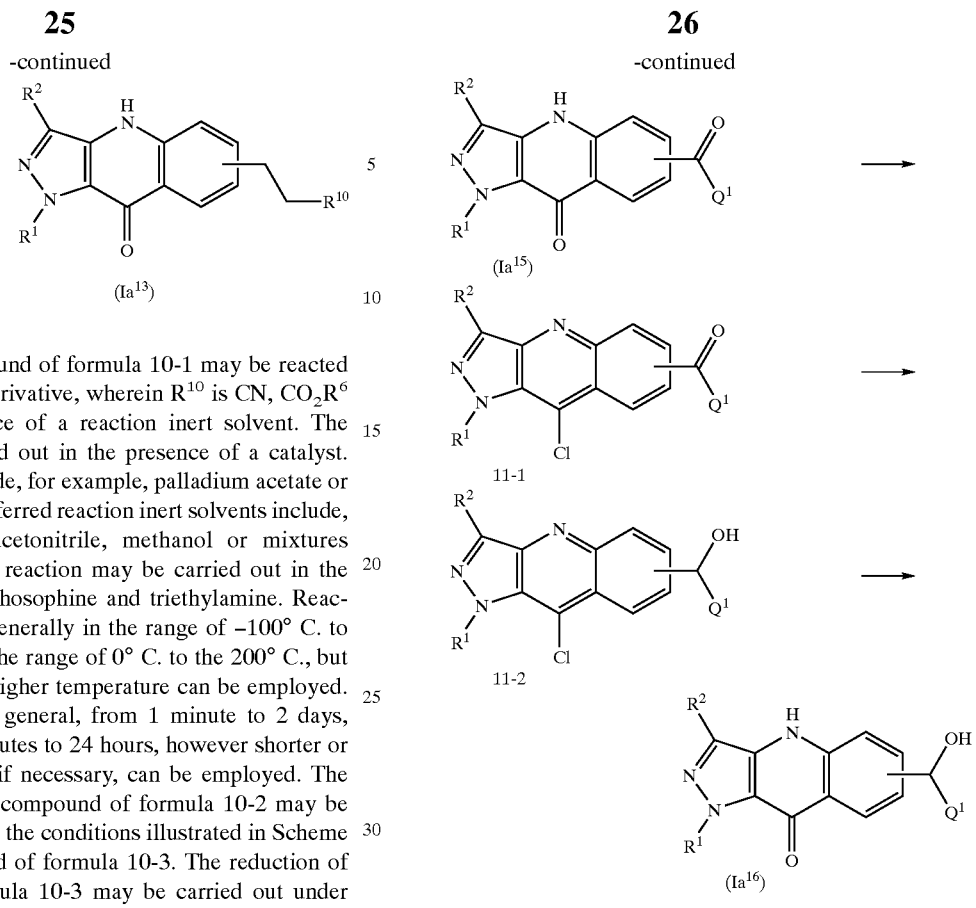

The obtained compound of formula 10-1 may be reacted with terminal alkene derivative, wherein $R^{10}$ is CN, $CO_2R^6$ or aryl, in the presence of a reaction inert solvent. The reaction may be carried out in the presence of a catalyst. Suitable catalysts include, for example, palladium acetate or palladium chloride. Preferred reaction inert solvents include, for example, DMF, acetonitrile, methanol or mixtures thereof. If desired, the reaction may be carried out in the presence of tri-o-tolylphosophine and triethylamine. Reaction temperatures are generally in the range of −100° C. to 250° C., preferably in the range of 0° C. to the 200° C., but if necessary, lower or higher temperature can be employed. Reaction times are, in general, from 1 minute to 2 days, preferably from 20 minutes to 24 hours, however shorter or longer reaction times, if necessary, can be employed. The hydrolysis of obtained compound of formula 10-2 may be carried out according to the conditions illustrated in Scheme 1 to give the compound of formula 10-3. The reduction of the compound of formula 10-3 may be carried out under known hydrogenation conditions in the presence of a metal catalyst under hydrogen atmosphere. A preferred metal catalyst is selected from, for example, palladium catalysts such as Pd—C, platinum catalysts such as $PtO_2$, or ruthenium catalysts such as $RuCl_2 (Ph_3P)_3$. Preferred reaction inert solvents include, for example, methanol, ethanol, ethyl acetate, THF or mixtures thereof. The reaction may be carried out at a temperature in the range from of −100 to 150° C., preferably in the range of 0° C. to 100° C., but if necessary, lower or higher temperature can be employed. Reaction times are, in general, from 1 minute to 2 days, preferably from 20 minutes to 24 hours, however shorter or longer reaction times, if necessary, can be employed.

Reaction Scheme 11 illustrates a method for the preparation of the compound of formula (Ia) wherein at least one of $Y^1$, $Y^2$, $Y^3$ and $Y^4$ is —CH(OH)$Q^1$(hereinafter represented by Formula (Ia$^{16}$)). The compound of formula (Ia) wherein at least one of $Y^1$, $Y^2$, $Y^3$ and $Y^4$ is —CH$_2Q^1$ (hereinafter represented by Formula (Ia$^{14}$)) may be prepared according to the same procedure as described in Scheme 1 or 2.

Scheme 11

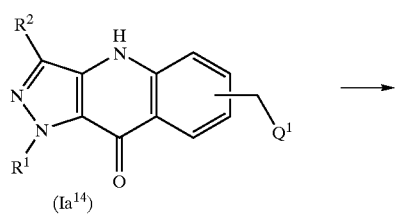

This compound may be subjected to oxidation to give the compound of formula (Ia) wherein at least one of $Y^1$, $Y^2$, $Y^3$ and $Y^4$ is —(C=O)$Q^1$ (hereinafter represented by Formula (Ia$^{15}$)). The oxidation may be carried out in the presence of or absence of a suitable oxidizing agent in a reaction inert solvent or without solvent. Preferred oxidizing agents include, for example, manganese oxide, chromium oxide, selenium dioxide and ceric ammonium nitrate (CAN). Preferred reaction inert solvents include, for example, water, ethanol, acetone, dimethylsulfoxide(DMSO), acetic anhydride, acetonitrile or mixtures thereof. Reaction temperatures are generally in the range of to −50° C. to reflux temperature, preferably in the range of −20° C. to reflux temperature, but if necessary, lower or higher temperature can be employed. Reaction times are, in general, from 1 minute to 3 days, preferably from 20 minutes to 2 days, however shorter or longer reaction times, if necessary, can be employed. The obtained compound of formula Ia$^{15}$ may be reacted with halogenating reagent to give the compound of formula 11-1. In case of $L^1$ is Cl, a suitable halogenating reagent is, for example, phosphoryl chloride, thionyl chloride or oxalyl chloride. The reaction may be carried out at a temperature in the range from of 0° C. to 250° C., preferably in the range of 50° C. to 150° C., but if necessary, lower or higher temperature can be employed. Reaction times are, in general, from 1 minute to a few days, preferably from 30 minutes to 12 hours, however shorter or longer reaction times, if necessary, can be employed. The reaction may be carried out in a reaction inert solvent or without solvent. Suitable reaction inert solvents include, for example, acetonitrile, dichloromethane or toluene. Then the resulting compound of formula 11-1 may be subjected to reduction to give the compound of formula 11-2. The reduction may be carried out in the presence of a suitable reducing agent in a reaction inert solvent or without solvent. Preferred reducing agents include, for example, NaBH$_4$, LiAlH$_4$ or LiBH$_4$. Preferred reaction inert solvents include, methanol, ethanol, diglyme, benzene, toluene, xylene, o-dichlorobenzene, dichloromethane, 1,2-dichloroethane, tetrahydrofuran, 1,4-dioxane, or mixtures thereof. Reaction temperatures are generally in the range of −100 to 150° C., preferably in the range of −20 to 100° C., but if necessary, lower or higher temperature can be employed. Reaction times are, in general, from 1 minute to 2 days, preferably from 20 minutes to 24 hours, however shorter or longer reaction times, if necessary, can be employed. The hydrolysis of the obtained compound of formula 11-2 may be carried out by conventional procedures. The hydrolysis may be carried out by treatment with acid in the presence or absence of a reaction inert solvent. Preferred acids include, for example, acetic acid, hydrochloric acid, trifluoroacetic acid or sulfuric acid. Preferred reaction inert solvents include, for example, water, aqueous tetrahydrofuran(THF), aqueous DMF or the mixture of them. Reaction temperatures are generally in the range of 0° C. to 200° C., preferably in the range of 50° C. to the 150° C., but if necessary, lower or higher temperature can be employed. Reaction times are, in general, from 1 minute to 2 days, preferably from 20 minutes to 24 hours, however shorter or longer reaction times, if necessary, can be employed.

Reaction Scheme 12 illustrates a method for the preparation of the compound of formula (Ia). The compound of formula 12-1 wherein at least one of X$^1$, X$^2$, X$^3$ and X$^4$ is halo or OTf may be prepared according to the same procedure as described in Scheme 1 or 2.

Scheme 12

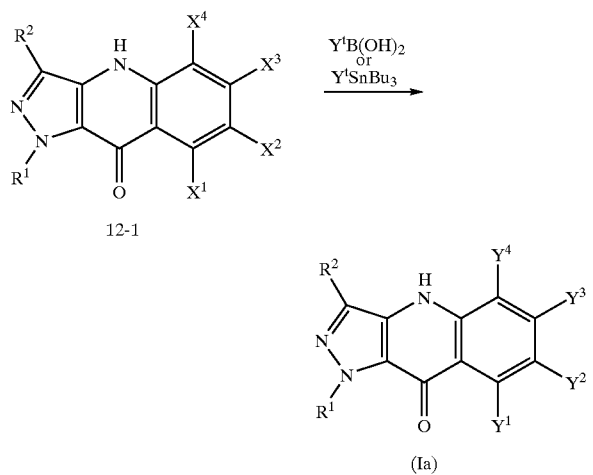

This compound may be subjected to coupling reaction using appropriate coupling reagents of formula 12-2, wherein Y$^r$ is independently selected from Y$^1$, Y$^2$, Y$^3$ and Y$^4$(with the proviso Y$^r$ is not H) in the presence of catalysts. Suitable coupling reagents include aryl or heteroaryltrialkylstannane, aryl or heteroarylboronic acid, arylalkyl or heteroarylalkyltrialkylstannane, or arylalkyl or heteroarylalkyltrialkylboronic acid. Suitable catalysts include, for example, tetrakis(triphenylphosphine)palladium or dichlorobis(triphenylphosphine)palladium. If desired, the reaction may be carried out in the presence of halogenomethal, such as lithium chloride. The reaction may be carried out in a reaction inert solvent or without solvent. Suitable reaction inert solvents include, for example, hexamethylphosphoramide(HMPA), 1,4-dioxane, dimethoxyethane(DME) or N,N-dimethylformamide. Reaction temperatures are generally in the range of to 0° C. to 250° C., preferably in the range of 20° C. to 150° C., but if necessary, lower or higher temperature can be employed. Reaction times are, in general, from 1 minute to 2 days, preferably from 20 minutes to a day, however shorter or longer reaction times, if necessary, can be employed.

Reaction Scheme 13 illustrates a method for the preparation of the compound of formula (Ia) wherein at least one of Y$^1$, Y$^2$, Y$^3$ and Y$^4$ is —(CH$_2$)$_n$PhOC$_{1-4}$alkyl (hereinafter represented by Formula (Ia$^{17}$)). The compound of formula (Ia$^2$) may be prepared according to the same procedure as described in Scheme 2.

Scheme 13

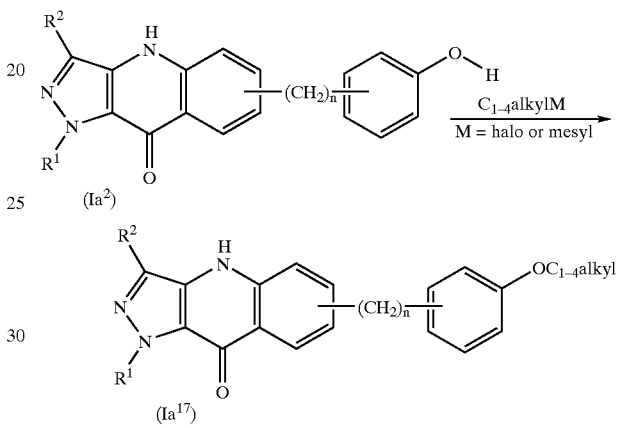

This compound may be treated with appropriate optionally substituted alkyl halides or alkyl mesylate in the presence of a base. Suitable bases include, for example, potassium carbonate, sodium carbonate, lithium carbonate, sodium hydride (NaH) or potassium t-butoxide. This reaction may be carried out in a reaction inert solvent or without solvent. Suitable reaction inert solvents include, for example, acetone, DME, THF or DMF. Reaction temperatures are generally in the range of −50° C. to 200° C., preferably in the range of −20° C. to 100° C., but if necessary, lower or higher temperature can be employed. Reaction times are, in general, from 1 minute to 2 days, preferably from 20 minutes to 12 hours, however shorter or longer reaction times, if necessary, can be employed.

Reaction Scheme 14 illustrates a method for the preparation of the compound of formula (Ia$^0$). The compound of formula (Ia) may be prepared according to the same procedure as described in Scheme 1 or 2.

Scheme 14

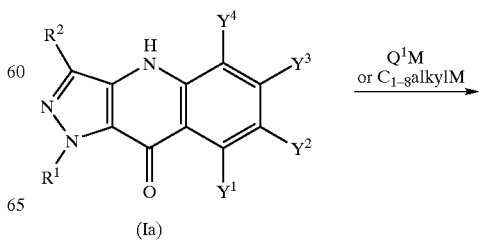

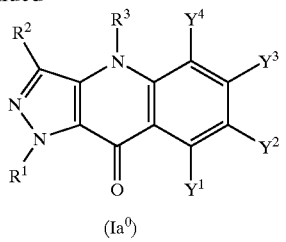

(Ia⁰)

This compound may be subjected to N-alkylation to give the compound of formula (Ia⁰). This compound may be treated with appropriate optionally substituted $C_{1-8}$alkylM or $Q^1M$(M is halogen or leaving group such as —O-mesyl (OMs), —O-tosyl(OTs) or OTf) in the presence of a base. Suitable bases include, for example, potassium carbonate, sodium carbonate, lithium carbonate, sodium hydride (NaH) or potassium t-butoxide. This reaction may be carried out in a reaction inert solvent or without solvent. Suitable reaction inert solvents include, for example, acetone, DME, THF, DMSO or DMF. Reaction temperatures are generally in the range of −50° C. to 200° C., preferably in the range of −20° C. to 150° C., but if necessary, lower or higher temperature can be employed. Reaction times are, in general, from 1 minute to 3 days, preferably from 20 minutes to 2 days, however shorter or longer reaction times, if necessary, can be employed.

Reaction Scheme 15 illustrates a method for the preparation of the compound of formula (Ia) wherein $R^3$ is —$C_{1-8}$alkyl-$N(R^5)R^4$ (hereinafter represented by Formula (Ia¹⁹)). The compound of formula (Ia) wherein $R^3$ is —$C_{1-8}$alkyl-X(X is halo or leaving group)(hereinafter represented by Formula (Ia¹⁸)) may be prepared according to the same procedure as described in Scheme 1 or 2.

Scheme 15

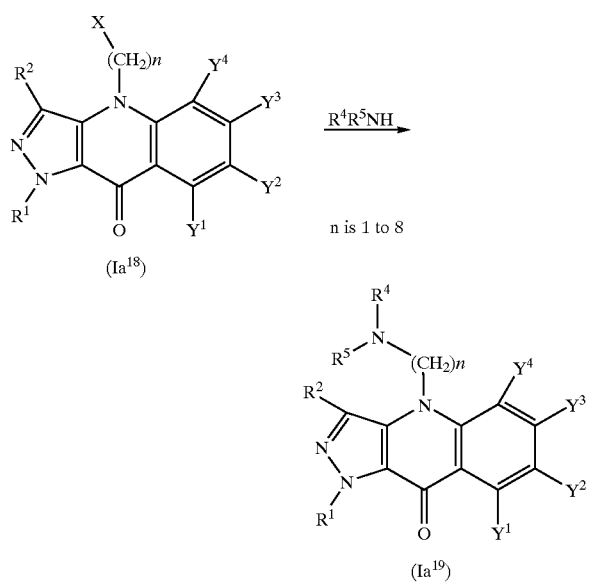

This compound may be treated with $HN(R^5)R^4$ in a reaction inert solvent or without solvent. Suitable reaction inert solvents include, for example, methanol, ethanol, THF, DMSO or DMF. Reaction temperatures are generally in the range of 0° C. to 200° C., preferably in the range of 20° C. to 150° C., but if necessary, lower or higher temperature can be employed. Reaction times are, in general, from 1 minute to a day, preferably from 20 minutes to 12 hours, however shorter or longer reaction times, if necessary, can be employed.

Reaction Scheme 16 illustrates a method for the preparation of the compound of formula (Ia) wherein $R^3$ is —$C_{1-8}$alkyl-$NH_2$ (hereinafter represented by Formula (Ia²¹)) through the azide compound of formula (Ia) wherein $R^3$ is —$C_{1-8}$alkyl-$N_3$ (hereinafter represented by Formula (Ia²⁰)).

Scheme 16

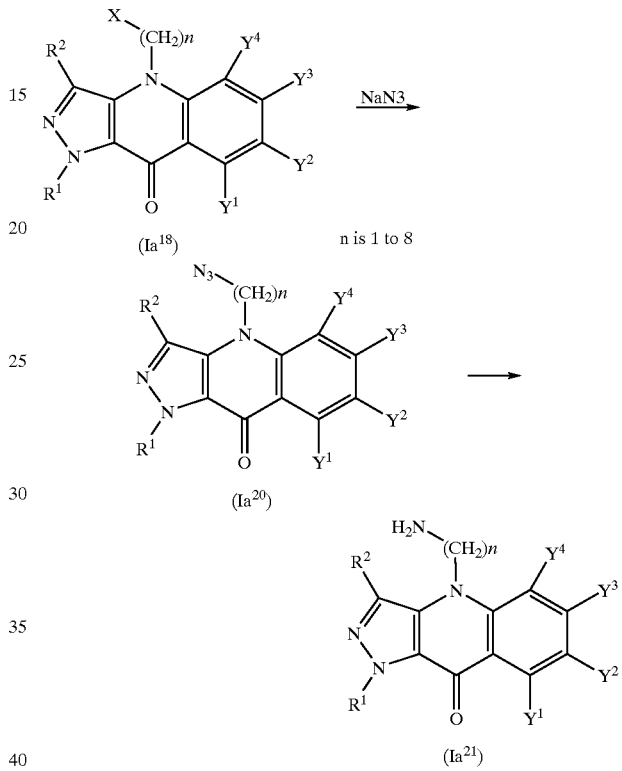

The nucleophilic displacement of leaving group of the compound of formula (Ia¹⁸) with azide may be carried out by conventional procedures in the absence or presence of a reaction inert solvent. Preferred reaction inert solvents include, for example, benzene, toluene, xylene, o-dichlorobenzene, nitrobenzene, dichloromethane, 1,2-dichloroethane, dimethylformamide (DMF), dimethoxyethane (DME), hexamethylphosphoramide (HMPA) or mixtures thereof. Preferred azide agents are selected from, for example, sodium azide or lithium azide. Reaction temperatures are generally in the range of −100 to 250° C., preferably in the range of 0° C. to 150° C., but if necessary, lower or higher temperature can be employed. Reaction times are, in general, from several minutes to 2 days, preferably from 20 minutes to 24 hours, however shorter or longer reaction times, if necessary, can be employed. The compound of formula Ia²⁰ may also be prepared by the Mitsunobu reaction. The compound of formula Ia¹⁸ may be treated with diphenylphosphoryl azide (DPPA) or $HN_3$ in the presence of dialkyl azodicarboxylate such as diethyl azodicarboxylate (DEAD) and phosphine reagent such as triphenylphosphine. Preferably, this reaction may be carried out in a reaction-inert solvent. Preferred reaction inert solvents include, but are not limited to, tetrahydrofuran (THF), diethyl ether, dimethylformamide (DMF), benzene, toluene, xylene, o-dichlorobenzene, nitrobenzene, dichloromethane, 1,2- dichloroethane, dimethoxyethane (DME), or mixtures thereof. The reduction of azide group may be carried out in the presence of a suitable reducing agent such as lithium aluminum hydride, sodium borohydride, triethyl phosphite, triphenylphosphine, zinc, dibutyl tinhydride or diboran in a reaction inert solvent selected form, but not limited to, THF, diethyl ether, methanol, ethanol and toluene. If desired, the reaction may be carried out under acidic conditions in the presence of hydrochloric acid or acetic acid. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The reduction may also be carried out under known hydrogenation conditions in the presence of a metal catalyst such as Lindler catalysts, Raney nickel catalysts, palladium catalysts or platinum catalysts (preferably Lindler catalysts, palladium catalysts or platinum catalysts). This reaction may be carried out under hydrogen atmosphere in a reaction inert solvent such as methanol, ethanol, ethyl acetate, THF or mixtures thereof. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 6 hours, however shorter or longer reaction times, if necessary, can be employed. If necessary, this reduction may be carried out under the adequate pressure in the range from about 0.5 to 10 kg/cm$^2$, preferably in the range from 1 to 6 kg/cm$^2$.

Reaction Scheme 17 illustrates a method for the preparation of the compound of formula (Ia) wherein $R^3$ is —$C_{1-8}$alkyl-NHSO$_2$C$_{1-4}$ alkyl (hereinafter represented by Formula (Ia$^{22}$)).

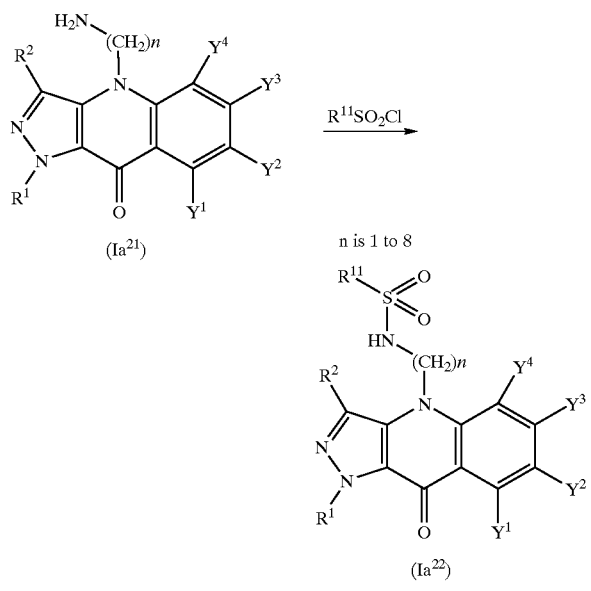

Scheme 17

117–118, 379–384). More specifically, the compound of formula Ia$^{21}$ may be treated with C$_{1-4}$ alkylsulfonyl halide in a reaction inert solvent. Suitable reaction inert solvents include, for example, dichloromethane, dichloroethane, pyridine or mixtures thereof. Reaction temperatures are generally in the range of −100 to 250° C., preferably in the range of 0° C. to the reflux temperature, but if necessary, lower or higher temperature can be employed. Reaction times are, in general, from 1 minute to 3 days, preferably from 1 hour to 65 hours, however shorter or longer reaction times, if necessary, can be employed.

Reaction Scheme 18 illustrates a method for the preparation of the compound of formula (Ia) wherein $R^3$ is 4-piperidinyl (hereinafter represented by Formula (Ia$^{24}$)) and the compound of formula (Ia) wherein $R^3$ is 1-methyl-4-piperidinyl (hereinafter represented by Formula (Ia$^{25}$)). The compound of formula (Ia$^{23}$) wherein PG is suitable protecting group for amino group may be prepared according to the same procedure as described in Scheme 14.

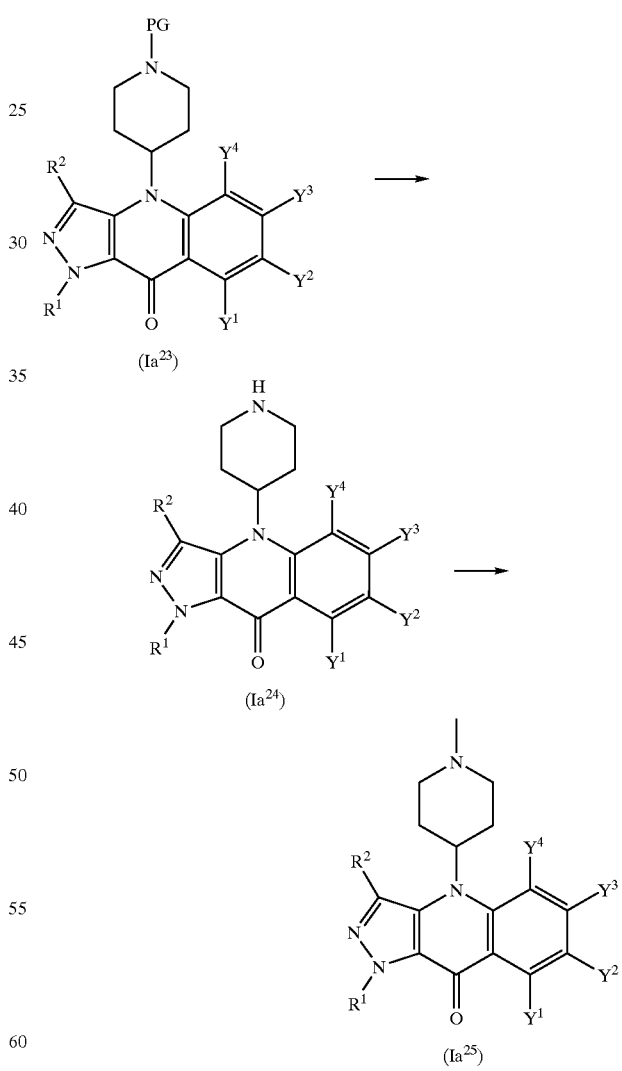

Scheme 18

Sulfonylation of the amino group of the compound Ia$^{21}$ may be carried out by a number of standard procedures known to those skilled in the art (e.g., "Protection for the Hydroxy Group and the Amino Group", in *Protective Groups in Organic Synthesis*, 2nd Edition, T. W. Greene and P. G. M. Wuts, Ed., John Wiley and Sons, Inc. 1991, pp.

Cleavage of the protecting group may be carried out by a number of standard procedures known to those skilled in the art (e.g., "Protection for the Amino Group", in *Protective Groups in Organic Synthesis*, 3rd Edition, T. W. Greene and P. G. M. Wuts, Ed., John Wiley and Sons, Inc. 1991, pp.

494–614). N-methylation of the compound of formula (Ia$^{24}$) may be carried out under the standard conditions known to those skilled in the art to afford the compound of formula (Ia$^{25}$). For example, the compound of formula (Ia$^{24}$) may be treated with formalin in the presence of reducing agent in a reaction inert solvent. Suitable reducing agents include, for example, NaBH$_4$, LiAlH$_4$, NaBH$_3$CN or LiBH$_4$. Formula Ia$^{21}$ may be treated with C$_{1-4}$ alkylsulfonyl halide in a reaction inert solvent. Suitable reaction inert solvents include, for example, dichloromethane, DME, THF, benzene or mixtures thereof. The reaction may be carried out in the presence of an acid. Suitable acids include, for example, acetic acid, hydrochloric acid or sulfuric acid. Reaction temperatures are generally in the range of −50 to 100° C., preferably in the range of −10 to 50° C., but if necessary, lower or higher temperature can be employed. Reaction times are, in general, from 1 minute to a day, preferably from 1 hour to 12 hours, however shorter or longer reaction times, if necessary, can be employed.

Reaction Scheme 19 illustrates a method for the preparation of the compound of formula (Ia) wherein R$^3$ is Q$^1$ (Q$^1$ is aryl or heteroaryl; hereinafter represented by Formula (Ia$^{26}$)).

Scheme 19

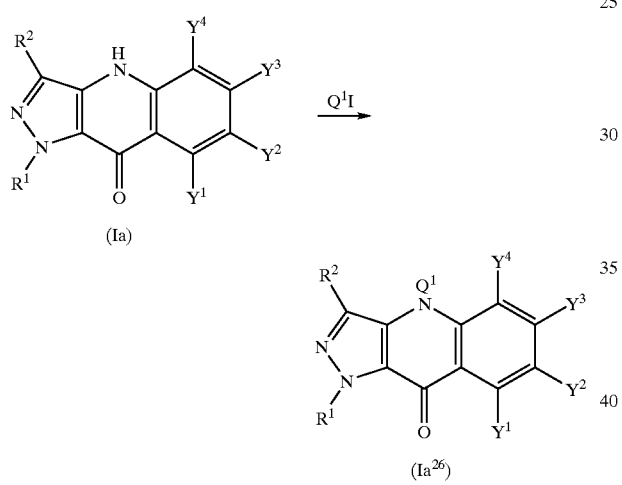

The reaction may be carried out under the Ullman reaction condition in the presence of copper or copper oxide. The compound of formula Ia may be treated with a compound of Q$^1$I in the absence or presence of a reaction inert solvent. Preferred reaction inert solvents include, for example, benzene, toluene, xylene, o-dichlorobenzene, nitrobenzene, pyridine, dimethylformamide (DMF), dimethoxyethane (DME) or mixtures thereof. Preferably, the reaction may be conducted in the presence of base. Preferred base include, for example, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine. Reaction temperatures are generally in the range of −100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

Reaction Scheme 20 illustrates a method for the preparation of the compound of formula (Ia) wherein R$^3$ is —(CH$_2$)$_2$X (X is halo; hereinafter represented by Formula (Ia$^{29}$)). The compound of formula (Ia) wherein R$^3$ is —(CH$_2$)$_2$OPG$^2$ (PG$^2$ is protecting group for hydroxy group; hereinafter represented by Formula (Ia$^{27}$)) may be prepared according to the same procedure as described in Scheme 14.

Scheme 20

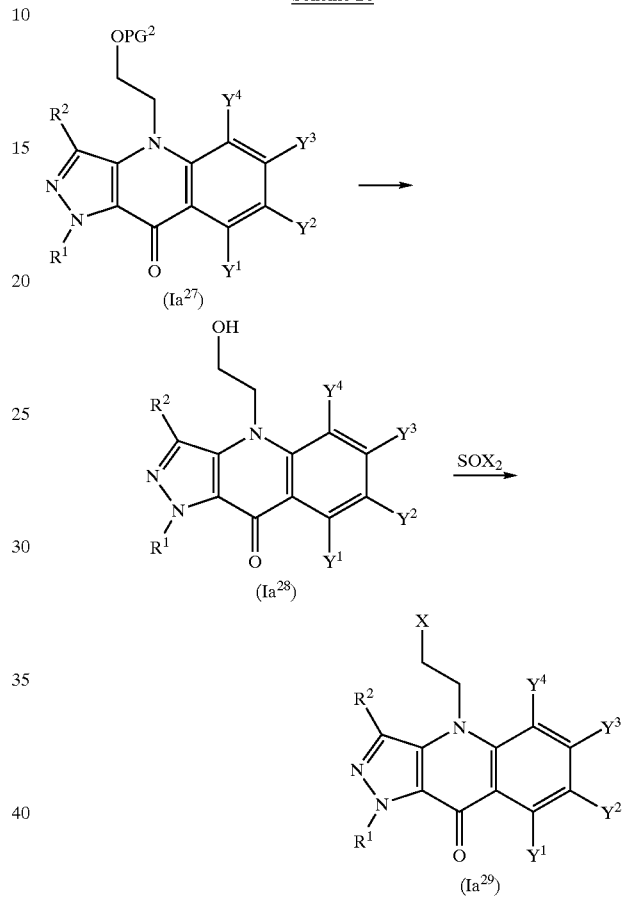

Cleavage of the protecting group may be carried out by a number of standard procedures known to those skilled in the art (e.g., "Protection for the Hydroxy Group", in Protective Groups in Organic Synthesis, 3rd Edition, T. W. Greene and P. G. M. Wuts, Ed., John Wiley and Sons, Inc. 1991, pp. 17–245). The obtained compound of formula Ia wherein R$^3$ is —(CH$_2$)$_2$OH (hereinafter represented by Formula (Ia$^{28}$)) may be reacted with halogenating reagent to give the compound of formula Ia$^{29}$. When X is Cl, a suitable halogenating reagent is, for example, phosphoryl chloride or thionyl chloride. The reaction may be carried out in a reaction inert solvent. Suitable reaction inert solvents include, for example, benzene, toluene, dichloromethane, DMF, THF or mixtures thereof. Reaction temperatures are generally in the range of −50 to 100° C., preferably in the range of 0 to 50° C., but if necessary, lower or higher temperature can be employed. Reaction times are, in general, from 1 minute to a day, preferably from 1 hour to 5 hours, however shorter or longer reaction times, if necessary, can be employed.

Reaction Scheme 21 illustrates a method for the preparation of the compound of formula (I) wherein Y$^1$ and Y$^3$ to Y$^8$ are hydrogen(hereinafter represented by Formula (Ib)).

Scheme 21

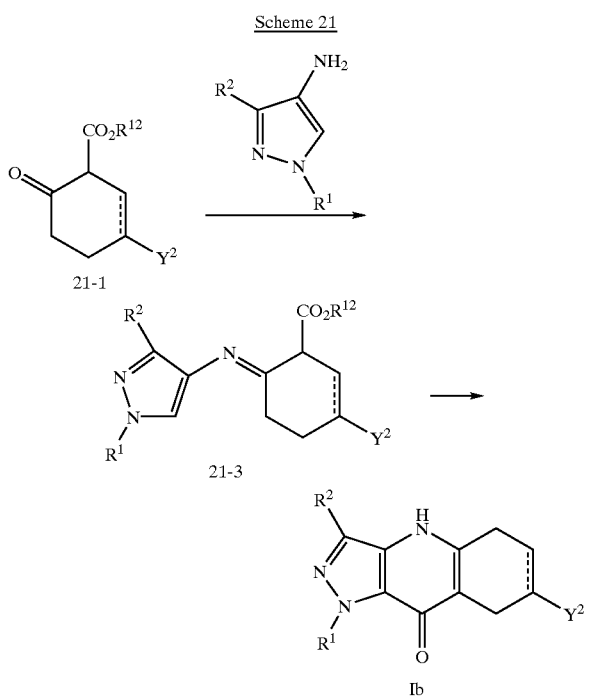

The compound of formula 21-1 wherein $R^{12}$ is $C_{1-4}$alkyl may be prepared according to standard procedures known to those skilled in the art (e.g., G. A. Russell and L. O. Ochrymowycz, *J. Org. Chem.*, 1969, 34, 3624). The compound of formula 21-2 may be prepared according to standard procedures known to those skilled in the art (e.g., J. Catalan et al., *J. Heterocycl. Chem.*, 1985, 22, 997). These compounds may be reacted in the presence of an acid catalyst in a reaction inert solvent. Suitable acid catalysts include, for example, p-toluenesulfonic acid(p-TsOH) or camphersulfonic acid(CSA). Suitable reaction inert solvents include, for example, benzene, toluene, DMF, THF or mixtures thereof. Reaction temperatures are generally in the range of 0 to 200° C., preferably in the range of 50 to 150° C., but if necessary, lower or higher temperature can be employed. Reaction times are, in general, from 1 minute to a day, preferably from 1 hour to 6 hours, however shorter or longer reaction times, if necessary, can be employed. The obtained imino compound of formula 21-3 may be cyclized under the heating conditions in a reaction inert solvent or without solvent. Suitable reaction inert solvents include, for example, xylene, diphenylether or mixtures thereof. Reaction temperatures are generally in the range of 0 to 300° C., preferably in the range of 150 to 250° C., but if necessary, lower or higher temperature can be employed. Reaction times are, in general, from 1 minute to a day, preferably from 0.5 hour to 3 hours, however shorter or longer reaction times, if necessary, can be employed.

The starting materials 1-1, 1-2, 2-1, 2-0, 2-2, 3-1 and the other reactants are known or commercially available compounds, or may be prepared according to known procedures for a person skilled in the art.

The present invention includes salt forms of the compounds (I) as obtained above. Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine(i.e., N-benzyl-2-phenylethylamine), benzathine(i.e., N,N-dibenzylethylenediamine), choline, diolamine(i.e., diethanolamine), ethylenediamine, glucosamine, glycine, guanidine, guanine, meglumine(i.e., N-methylglucamine), nicotinamide, olamine(i.e., ethanolamine), ornithine, procaine, proline, pyridoxine, serine, tyrosine, valine and tromethamine(i.e., tris or tris (hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, (i.e., 1,2-ethanedisulfonate), estolate(i.e., laurylsulfate), gluceptate(i.e., gluscoheptonate), gluconate, 3-hydroxy-2-naphthoate, xionofoate(i.e., 1-hydrroxy-2-naphthoate), isethionate,(i.e., 2-hydroxyethanesulfonate), mucate(i.e., galactarate), 2-naphsylate(i.e., naphthalenesulphonate), stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1,1'-methylene-bis-(2-hydroxy-3-naphthoate). The acid addition salts can be prepared by conventional procedures.

The compounds of formula (I) of this invention may contain one or more asymmetric centers. Thus, the compounds can exist in separated (+)- and (−)-optically active forms, as well as in the racemic form thereof. The present invention includes all such forms within its scope. Individual isomers can be obtained by known methods, such as optically selective reaction or chromatographic separation in the preparation of the final product or its intermediate.

In addition, when the compounds of this invention form hydrates or solvates they are also within the scope of this invention.

The pyrazoloquinolinone compounds of this invention have protein kinase C (PKC) inhibitory activities, and thus are useful for the treatment of neuropathic pain, acute or chronic inflammatory pain, auditory deficiency (synaptic repair), hypertension, forcal celebral ischemia, pulmonary fibrosis, diabetes, immune disease, colonic repair, drug resistance (MDR regulation), Alzheimer, sepsis, shock, ARDS, inflammation, ischemia, gastric acid regulation, diabetic neuropathy, asthma, HIV infection, gastric ulcer or cerebral ischemia or the like in mammalian, especially human.

The compounds of the invention may prevent expression of the morphine tolerance.

Method for Assessing Biological Activities:

The PKC inhibitory activity of the compounds of this invention are determined by the following procedures.

In vitro Assays

Protein Kinase C (PKC) Assay

The assay components are in a total of 100 μl, including 45 mM Tris-HCl buffer pH 7.5 (Life Technologies), 0.75 mM calcium acetate (Wako), 3.6 mM magnesium chloride (Wako), 1.875 mM DL-dithiothreitol (Sigma), 18.75 μg/ml L-(α-phosphatidyl-L-serine (Sigma), 1.5 μg/ml phorbol 12-myristate 13-acetate (Sigma), 2.5 μM biotinylated peptide (neurogranin 28–43, Asahi Techno Glass), 10 μl of 1.0% aqueous DMSO or DMSO/inhibitor and 0.3 μM (gamma 33P) ATP (NEN). The reaction was initiated by the addition of human recombinant PKCα (Calbiochem), PKCβ2 (Calbiochem) or PKCγ (Calbiochem or in-house preparation), incubated at room temperature for 15 minutes and stopped by adding 100 μl of 5 mg/ml streptavidin SPA beads (Amersham Pharmacia Biotech) including 50 μM ATP (Sigma), 5 mM EDTA (Dojindo) and 0.1% Triton X-100 (Wako) in phosphate-buffered saline (Nissui). The reaction mixture was further incubated for 15 minutes, centrifuged at 1000 rpm for 1 minute and the radioactivity was quantified by TopCount (Packard).

cAMP-Dependent Protein Kinase (PKA) Assay

The PKA assay was performed essentially as described above except for the followings. Concentration of DL-dithiothreitol was set at 187.5 μM. L-α-Phosphatidyl-L-serine and phorbol 12-myristate 13-acetate were not used. Human recombinant PKA and biotinylated peptide (Kemptide, Peninsula laboratories) was prepared internally and the substrate was used at 1 μM.

The most preferred compounds prepared in the working examples as described below were tested by this method, and showed an $IC_{50}$ value of 0.1 μM to 1 μM with respect to inhibitory activity.

In vivo Assays

Neuropathic Pain Model

Chronic constriction injury (CCI) model (Bennett et al., Pain 33 87 1988) was used to investigate the effect of compounds on rat neuropathic pain model. SD rats (male, 8 weeks, Nippon SLC) were used in this assay. CCI of sciatic nerve was made by tying loose ligature with 4-0 chromic gut around aciatic nerve four times with 1 mm spacing. In sham-operated mice, the nerve was exposed without ligation.

Detection of Mechanical Allodynia

Efficacy of drugs on rat neurophatic pain model was examined by using von Frey Hair test (Semmes-Weinstein Monofilaments; North Coast Medical, Inc.). (Mechanical allodynia was examined by using von Frey Hair (Semmes-Weinstein Monofilaments; North Coast Medical, Inc.). Rats were placed on a mesh floor, so that the plantar surface of the hindpaw can be stimulated from below. Each hair was applied to the midplantar of hindpaw 10 times in order of increasing stiffness. The first hair in the series that evoked at least 1 response was designated the threshold.) This test was performed 14 days after the surgery.

The pyrazoloquinolinone compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254}$, precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230–400 mesh ASTM) or Fuji Silysia Chromatorex® DU3050 (Amino Type, 30–50 μm). Low-resolution mass spectral data (EI) were obtained on a Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.).

Chemical symbols have their usual meanings; b.p. (boiling point), m.p. (melting point), l (liter(s)), ml (milliliter(s)), g (gram(s)), mg(milligram(s)), mol (moles), mmol (millimoles), eq. (equivalent(s)).

Example 1
7-FLUORO-1-METHYL-1,4-DIHYDRO-9H-PYRAZOLO[4,3-b]QUINOLIN-9-ONE.

Step 1. 4-[(4-Fluorophenyl)amino]-1-methyl-1H-pyrazole-5-carboxylic acid

A mixture of 4-iodo-1-methyl-1H-pyrazole-5-carboxylic acid ((Manaev, Yu. A. et al., *J. Gen. Chem. USSR* (*Engl. Transl.*), 1982, 52 (11), 2291), 500 mg, 1.98 mmol), 4-fluoroaniline (0.94 ml, 9.90 mmol), copper powder (200 mg) and 5% aqueous sodium carbonate (10 ml) was stirred for 16 h at 100° C. After cooling to room temperature, 2N aqueous sodium hydroxide (100 ml) and diethyl ether (50 ml) were added to the mixture. The mixture was filtered through a pad of Celite. The water layer was separated, washed with diethyl ether (50 ml) and acidified with concentrated hydrochloric acid. The formed precipitate was collected by filtration and dried to give 282 mg (61%) of the title compound as a white solid.

Rf value: 0.50 (methanol/dichloromethane/acetic acid=1/10/2 drops).
$^1$H-NMR (DMSO-$d_6$) δ: 7.60 (1 H, s), 7.09–7.05 (4 H, m), 4.01 (3 H, s). Two signals due to NH and $CO_2H$ were not observed.

Step 2. 7-Fluoro-1-methyl-1,4-dihydro-9H-pyrazolo[4,3-b]quinolin-9-one

A suspension of 4-[(4-fluorophenyl)amino]-1-methyl-1H-pyrazole-5-carboxylic acid (EXAMPLE 1, step 1, 280 mg, 1.19 mmol) in phosphorus oxychloride (6 ml) was refluxed for 3 h. After cooling to room temperature, the mixture was concentrated and dried in vacuo. The residue was dissolved in 50% aqueous acetic acid (6 ml) and refluxed for 8 h. After cooling to room temperature, the mixture was diluted with ethyl acetate (200 ml), washed with saturated aqueous sodium bicarbonate (100 ml) and dried over magnesium sulfate. Removal of solvent and recrystallization from ethyl acetate gave 98 mg (38%) of the title compound as a solid.

MS (EI) m/z: 216 ($M^+$).
m.p.: 301° C. (recrystallized from ethyl acetate).
IR (KBr) ν: 3182, 3125, 3067, 2997, 2937, 1601, 1541, 1489, 1433, 1402, 1121, 544 $cm^{-1}$.
$^1$H-NMR (DMSO-$d_6$) δ: 7.91–7.85 (1 H, m), 7.85 (1 H, s), 7.63–7.60 (2 H, m), 4.31 (3 H, s). One signal due to NH was not observed.
Anal. Calcd. for $C_{11}H_8FN_3O.0.2H_2O$: C, 59.84; H, 3.83; N, 19.03. Found: C, 59.64; H, 3.76; N, 19.02.

Example 2
5-FLUORO-1-METHYL-1,4-DIHYDRO-9H-PYRAZOLO[4,3-b]QUINOLIN-9-ONE

Step 1. 4-[(2-Fluorophenyl)amino]-1-methyl-1H-pyrazole-5-carboxylic acid

The title compound was prepared according to the procedure of step 1 in EXAMPLE 1 (CJ-022998) using 2-fluoroaniline, instead of 4-fluoroaniline.
Rf value: 0.50 (methanol/dichloromethane/acetic acid=1/10/2 drops).
$^1$H-NMR (DMSO-$d_6$) δ: 7.78 (1 H, s), 7.64–7.37 (1 H, m), 7.24–7.10 (2 H, m), 6.85–6.81 (1 H, m), 4.03 (3 H, s). Two signals due to NH and $CO_2H$ were not observed.

Step 2. 5-Fluoro-1-methyl-1,4-dihydro-9H-pyrazolo[4,3-b]quinolin-9-one

The title compound was prepared according to the procedure of step 2 in EXAMPLE 1 (CJ-022998) using 4-[(2-fluorophenyl)amino]-1-methyl-1H-pyrazole-5-carboxylic acid (EXAMPLE 2, step 1), instead of 4-[(4-fluorophenyl)amino]-1-methyl-1H-pyrazole-5-carboxylic acid.
MS (EI) m/z: 216 ($M^+$).
m.p.: >300° C. (recrystallized from ethyl acetate).
IR (KBr) ν: 3142, 1641, 1603, 1545, 1396, 1242, 853 $cm^{-1}$.
$^1$H-NMR (DMSO-$d_6$) δ: 11.89 (1 H, br s), 8.07 (1 H, d, J=8.4 Hz), 7.79 (1 H, s), 7.62 (1 H, ddd, J=1.3, 7.7 and 11.7 Hz), 7.20 (1 H, dt, J=5.0 and 7.9 Hz), 4.31 (3 H, s).
Anal. Calcd. for $C_{11}H_8FN_3O.0.3H_2O$: C, 54.91; H, 4.44; N, 17.46. Found: C, 54.99; H, 3.81; N, 17.12.

Example 3
6-FLUORO-1-METHYL-1,4-DIHYDRO-9H-PYRAZOLO[4,3-b]QUINOLIN-9-ONE

Step 1. 4-[(3-Fluorophenyl)amino]-1-methyl-1H-pyrazole-5-carboxylic acid

The title compound was prepared according to the procedure of step 1 in EXAMPLE 1 using 3-fluoroaniline, instead of 4-fluoroaniline.
Rf value: 0.50 (methanol/dichloromethane/acetic acid=1/10/2 drops).
$^1$H-NMR (DMSO-$d_6$) δ: 7.70 (1 H, s), 7.21 (1 H, q, J=6.9 Hz), 6.88–6.80 (2 H, m), 6.56 (1H, dt, J=2.5 and 8.9 Hz), 4.03 (3 H, s). Two signals due to NH and $CO_2H$ were not observed.

Step 2. 9-Chloro-6-fluoro-1-methyl-1H-pyrazolo[4,3-b]quinoline and 9-chloro-8-fluoro-1-methyl-1H-pyrazolo[4,3-b]quinoline A mixture of 4-[(3-fluorophenyl)amino]-1-methyl-1H-pyrazole-5-carboxylic acid (EXAMPLE 3, step 1, 470 mg, 2.00 mmol) in phosphorus oxychloride (10 ml) was refluxed for 3 h. After cooling to room temperature, the mixture was concentrated in vacuo. The residue was dissolved in ethyl acetate (100 ml), washed with water (30 ml) and saturated aqueous sodium bicarbonate (30 ml×2) and dried over magnesium sulfate. Removal of solvent gave a dark red residue, which was chromatographed on a column of silica gel eluting with ethyl acetate/hexane (1:5) to afford 189 mg (40%) of the 9-chloro-6-fluoro-1-methyl-1H-pyrazolo[4,3-b]quinoline as a pale yellow solid and 111 mg (24%) of the 9-chloro-8-fluoro-1-methyl-1H-pyrazolo[4,3-b]quinoline as a yellow solid.

9-chloro-6-fluoro-1-methyl-1H-pyrazolo[4,3-b]quinoline
Rf value: 0.3 (ethyl acetate/hexane=1/5).
$^{1}$H-NMR (CDCl$_3$) δ: 8.39 (1 H, dd, J=5.9 and 11.5 Hz), 8.38 (1 H, s), 7.80 (1 H, dd, J=2.6 and 10.1 Hz), 7.47 (1H, ddd, J=2.6, 7.7 and 9.7 Hz), 4.51 (3 H, s).
9-chloro-8-fluoro-1-methyl-1H-pyrazolo[4,3-b]quinoline
Rf value: 0.25 (ethyl acetate/hexane=1/5).
$^{1}$H-NMR (CDCl$_3$) δ: 8.40 (1 H, s), 8.01 (1 H, d, J=8.9 Hz), 7.63–7.55 (1 H, m), 7.30–7.22 (1 H, m), 4.55 (3 H, s).
Step 3. 6-Fluoro-1-methyl-1,4-dihydro-9H-pyrazolo[4,3-b]quinolin-9-one A mixture of 9-chloro-6-fluoro-1-methyl-1H-pyrazolo[4,3-b]quinoline (EXAMPLE 3, step 2, 180 mg, 0.764 mmol) in 50% aqueous acetic acid (8 ml) was refluxed for 2 h. After cooling to room temperature, the mixture was concentrated in vacuo to give a pale orange solid, which was recrystallized from ethyl acetate to afford 166 mg (100%) of the title compound as a solid.
MS (EI) m/z: 216 (M$^+$).
m.p.: 269° C. (recrystallized from ethyl acetate).
IR (KBr) ν: 3260, 3190, 3144, 1626, 1601, 1543, 1448, 1396, 1259, 1178 cm$^{-1}$.
$^{1}$H-NMR (DMSO-d$_6$) δ: 11.89 (1 H, br s), 8.29 (1 H, dd, J=6.3 and 9.1 Hz), 7.82 (1 H, s), 7.25 (1 H, dd, J=2.1 and 10.5 Hz), 7.08 (1 H, dt, J=2.5 and 9.1 Hz), 4.30 (3 H, s).
Anal. Calcd. for C$_{11}$H$_8$FN$_3$O: C, 60.83; H, 3.71; N, 19.35. Found: C, 60.87; H, 3.76; N, 19.34.

Example 4

8-FLUORO-1-METHYL-1,4-DIHYDRO-9H-PYRAZOLO[4,3-b]QUINOLIN-9-ONE

8-Fluoro-1-methyl-1,4-dihydro-9H-pyrazolo[4,3-b]quinolin-9-one

The title compound was prepared according to the procedure of step 3 in EXAMPLE 3 (CJ-023024) using 9-chloro-8-fluoro-1-methyl-1H-pyrazolo[4,3-b]quinoline (EXAMPLE 3, step 2), instead of 9-chloro-6-fluoro-1-methyl-1H-pyrazolo[4,3-b]quinoline.
MS (EI) m/z: 216 (M$^+$).
m.p.: >300° C. (recrystallized from ethyl acetate).
IR (KBr) ν: 3086, 2957, 1641, 1607, 1541, 1470, 1051, 800, 775, 615 cm$^{-1}$.
$^{1}$H-NMR (DMSO-d$_6$) δ: 7.78 (1 H, s), 7.59 (1 H, dt, J=5.4 and 8.6 Hz), 7.30 (1 H, d, J=3.2 Hz), 6.87 (1 H, dd, J=7.7 and 12.5 Hz), 4.27 (3 H, s). One signal due to NH was not observed.
Anal. Calcd. for C$_{11}$H$_8$FN$_3$O.0.4H$_2$O: C, 58.88; H, 3.95; N, 18.72. Found: C, 58.69; H, 3.63; N, 18.58.

Example 5

5-BROMO-1-METHYL-1,4-DIHYDRO-9H-PYRAZOLO[4,3-b]QUINOLIN-9-ONE

Step 1. 5-Bromo-1-methyl-1,4-dihydro-9H-pyrazolo[4,3-b]quinolin-9-one

The title compound was prepared according to the procedure of step 1 and step 2 in EXAMPLE 1 using 2-bromoaniline, instead of 4-fluoroaniline.
m.p.: 287° C. (recrystallized from ethyl acetate).
IR (KBr) ν: 3207, 1616, 1587, 1555, 1531, 1387, 1337, 932, 758, 746 cm$^{-1}$.
$^{1}$H-NMR (DMSO-d$_6$) δ: 11.25 (1 H, br s), 8.30 (1 H, dd, J=1.5 and 8.1 Hz), 8.04 (1 H, dd, J=1.5 and 7.6 Hz), 7.89 (1 H, s), 7.18 (1 H, t, J=8.1 Hz), 4.30 (3 H, s).
Anal. Calcd. for C$_{11}$H$_8$BrN$_3$O: C, 47.51; H, 2.90; N, 15.11. Found: C, 47.39; H, 2.98; N, 15.15.

Example 6

7-ETHYL-1-METHYL-1,4-DIHYDRO-9H-PYRAZOLO[4,3-b]QUINOLIN-9-ONE

Step 1. 4-[(4-Ethylphenyl)amino]-1-methyl-1H-pyrazole-5-carboxylic acid

The title compound was prepared according to the procedure of step 1 in EXAMPLE 1 using 4-ethylaniline, instead of 4-fluoroaniline.
Rf value: 0.50 (methanol/dichloromethane/acetic acid=1/10/2 drops).
$^{1}$H-NMR (DMSO-d$_6$) δ: 7.61 (1 H, s), 7.07 (2 H, d, J=8.2 Hz), 6.99 (2 H, d, J=8.4 Hz), 3.99 (3 H, s), 2.53–2.48 (2 H, m), 1.13 (3 H, t, J=7.6 Hz).
Step 2. 7-Ethyl-1-methyl-1,4-dihydro-9H-pyrazolo[4,3-b]quinolin-9-one The title compound was prepared according to the procedure of step 2 in EXAMPLE 1 using 4-[(4-ethylphenyl)amino]-1-methyl-1H-pyrazole-5-carboxylic acid (EXAMPLE 6, step 1), instead of 4-[(4-fluorophenyl)amino]-1-methyl-1H-pyrazole-5-carboxylic acid.
MS (EI) m/z: 226 (M$^+$).
m.p.: 266° C. (recrystallized from ethyl acetate).
IR (KBr) ν: 3261, 3201, 3148, 2959, 1636, 1614, 1593, 1541, 1489, 1400, 1317, 826 cm$^{-1}$.
$^{1}$H-NMR (DMSO-d$_6$) δ: 11.73 (1 H, br s), 8.05 (1 H, s), 7.79 (1 H, s), 7.56 (1 H, d, J=8.9 Hz), 7.47 (1 H, d, J=8.6 Hz), 4.31 (3 H, s), 2.72 (2 H, q, J=7.6 Hz), 1.24 (3 H, t, J=7.7 Hz).
Anal. Calcd. for C$_{13}$H$_{13}$N$_3$O.0.2H$_2$O: C, 67.63; H, 5.85; N, 18.20. Found: C, 67.70; H, 5.83; N, 17.96.

Example 7

5-ETHYL-1-METHYL-1,4-DIHYDRO-9H-PYRAZOLO[4,3-b]QUINOLIN-9-ONE

Step 1. 4-[(2-Ethylphenyl)amino]-1-methyl-1H-pyrazole-5-carboxylic acid

The title compound was prepared according to the procedure of step 1 in EXAMPLE 1 using 2-ethylaniline, instead of 4-fluoroaniline.
Rf value: 0.50 (methanol/dichloromethane/acetic acid=1/10/2 drops).
$^{1}$H-NMR (DMSO-d$_6$) δ: 7.57 (1 H, s), 7.50 (1 H, br s), 7.18–7.08 (3 H, m), 6.77 (1 H, t, J=7.4 Hz), 3.94 (3 H, s), 2.50 (2 H, q, J=7.6 Hz), 1.11 (3 H, t, J=7.6 Hz).
Step 2. 5-Ethyl-1-methyl-1,4-dihydro-9H-pyrazolo[4,3-b]quinolin-9-one The title compound was prepared according to the procedure of step 2 in EXAMPLE 1 using 4-[(2-ethylphenyl)amino]-1-methyl-1H-pyrazole-5-carboxylic acid (EXAMPLE 7, step 1), instead of 4-[(4-fluorophenyl)amino]-1-methyl-1H-pyrazole-5-carboxylic acid.
MS (EI) m/z: 226 (M$^+$).
m.p.: 254° C. (recrystallized from ethyl acetate).
IR (KBr) ν: 3296, 1614, 1583, 1549, 1435, 1396, 1369, 1346, 1308, 1175, 943, 764 cm$^{-1}$.
$^{1}$H-NMR (DMSO-d$_6$) δ: 10.95 (1 H, br s), 8.04 (1 H, dd, J=1.6 and 8.2 Hz), 7.70 (1 H, s), 7.42 (1 H, dd, J=1.5 and 7.1 Hz), 7.06 (1 H, dd, J=7.1 and 8.1 Hz), 4.19 (3 H, s), 2.81 (2 H, q, J=7.4 Hz), 1.18 (3 H, t, J=7.4 Hz).
Anal. Calcd. for C$_{13}$H$_{13}$N$_3$O.0.2H$_2$O: C, 67.63; H, 5.85; N, 18.20. Found: C, 67.72; H, 5.77; N, 18.17.

Example 8
8-ETHYL-1-METHYL-1,4-DIHYDRO-9H-PYRAZOLO[4,3-b]QUINOLIN-9-ONE and EXAMPLE 9: 6-ETHYL-1-METHYL-1,4-DIHYDRO-9H-PYRAZOLO[4,3-b]QUINOLIN-9-ONE Step 1. 4-[(3-Ethylphenyl)amino]-1-methyl-1H-pyrazole-5-carboxylic acid The title compound was prepared according to the procedure of step 1 in EXAMPLE 1 using 3-ethylaniline, instead of 4-fluoroaniline.

Rf value: 0.50 (methanol/dichloromethane/acetic acid=1/10/2 drops).

$^1$H-NMR (DMSO-$d_6$) δ: 7.66 (1 H, s), 7.14 (1 H, t, J=7.4 Hz), 6.90–6.88 (2 H, m), 6.68 (1 H, d, J=7.7 Hz), 4.01 (3 H, s), 2.55 (2 H, q, J=7.6 Hz), 1.16 (3 H, t, J=7.6 Hz). Two signals due to NH and $CO_2H$ were not observed.

Step 2. 8-Ethyl-1-methyl-1,4-dihydro-9H-pyrazolo[4,3-b]quinolin-9-one and 6-ethyl]-methyl-1,4-dihydro-9H-pyrazolo[4,3-b]quinolin-9-one.

4-[(3-Ethylphenyl)amino]-1-methyl-1H-pyrazole-5-carboxylic acid (EXAMPLE 8 and 9, step 1) was treated according to the procedure of step 2 in EXAMPLE 3 instead of 4-[(3-fluorophenyl)amino]-1-methyl-1H-pyrazole-5-carboxylic acid. The obtained inseparable mixture of 9-chloro-8-ethyl-1-methyl-1H-pyrazolo[4,3-b]quinoline and 9-chloro-6-ethyl-1-methyl-1H-pyrazolo[4,3-b]quinoline (200 mg, 0.81 mmol) in 50% aqueous acetic acid (8 ml) was refluxed for 8 h. After cooling to room temperature, the mixture was concentrated and chromatographed on a column of silica gel with ethyl acetate/hexane (1:2) to afford 75 mg (41%) of 8-ethyl-1-methyl-1,4-dihydro-9H-pyrazolo[4,3-b]quinolin-9-one as a solid and 103 mg (56%) of 6-ethyl-1-methyl-1,4-dihydro-9H-pyrazolo[4,3-b]quinolin-9-one as a solid.

8-ethyl-1-methyl-1,4-dihydro-9H-pyrazolo[4,3-b]quinolin-9-one

MS (EI) m/z: 227 ($M^+$).

m.p.: 250° C. (recrystallized from ethyl acetate).

IR (KBr) ν: 3287, 3215, 1616, 1595, 1547, 1464, 1431, 902, 781 $cm^{-1}$.

$^1$H-NMR (DMSO-$d_6$) δ: 7.74 (1 H, s), 7.49 (1 H, t, J=8.4 Hz), 7.35 (1 H, d, J=8.1 Hz), 6.93 (1 H, d, J=7.7 Hz), 4.29 (3 H, s), 3.40–3.32 (2 H, m), 1.22 (3 H, t, J=7.3 Hz). One signal due to NH was not obtained.

Anal. Calcd. for $C_{13}H_{13}N_3O\cdot0.1H_2O$: C, 68.16; H, 5.81; N, 18.34. Found: C, 68.08; H, 5.79; N, 17.99.

6-ethyl-1-methyl-1,4-dihydro-9H-pyrazolo[4,3-b]quinolin-9-one

MS (EI) m/z: 227 ($M^+$).

m.p.: 263° C. (recrystallized from ethyl acetate).

$^1$H-NMR (DMSO-$d_6$) δ: 8.15 (1 H, d, J=8.4 Hz), 7.78 (1 H, s), 7.30 (1 H, s), 7.10 (1 H, d, J=8.4 Hz), 4.30 (3 H, s), 2.74 (2 H, q, J=7.4 Hz), 1.25 (3 H, t, J=7.6 Hz). One signal due to NH was not obtained.

Anal. Calcd. for $C_{13}H_{13}N_3O\cdot0.2H_2O$: C, 67.63; H, 5.85; N, 18.20. Found: C, 67.56; H, 5.72; N, 17.95.

Example 10
8-ISOPROPYL-1-METHYL-1,4-DIHYDRO-9H-PYRAZOLO[4,3-b]QUINOLIN-9-ONE.

Step 1. 4-[(3-Isopropylphenyl)amino]-1-methyl-1H-pyrazole-5-carboxylic acid.

The title compound was prepared according to the procedure of step 1 in EXAMPLE 1 using 3-isopropylaniline, instead of 4-fluoroaniline.

Rf value: 0.20 (methanol/dichloromethane=1/9).

$^1$H-NMR (DMSO-$d_6$) δ: 7.65 (1 H, s), 7.15 (1 H, t, J=7.4 Hz), 6.92 (1 H, s), 6.85 (1 H, d, J=9.3 Hz), 6.71 (1 H, d, J=6.5 Hz), 4.02 (3 H, s), 2.88–2.75 (1H, m), 1.19 (6 H, d, J=7.0 Hz). Signals due to NH and $CO_2H$ were not observed.

Step 2. 9-Chloro-8-isopropyl-1-methyl-1H-pyrazolo[4,3-b]quinoline and 9-chloro-6-isopropyl-1-methyl-1H-pyrazolo[4,3-b]quinoline.

The title compounds were prepared as an inseparable mixture with a ratio of 1.2:3 according to the procedure of step 2 in EXAMPLE 3 using 4-[(3-isopropylphenyl)amino]-1-methyl-1H-pyrazole-5-carboxylic acid (EXAMPLE 10, step 1), instead of 4-[(3-fluorophenyl)amino]-1-methyl-1H-pyrazole-5-carboxylic acid.

9-chloro-8-isopropyl-1-methyl-1H-pyrazolo[4,3-b]quinoline

Rf value: 0.60 (ethyl acetate/hexane=1/1).

$^1$H-NMR ($CDCl_3$) δ: 8.36 (1 H, s), 8.08–8.02 (1 H, m), 7.63–7.61 (2 H, m), 4.76–4.68 (1 H, m), 4.54 (3 H, s), 1.43 (6 H, d, J=6.5 Hz).

9-chloro-6-isopropyl-1-methyl-1H-pyrazolo[4,3-b]quinoline

Rf value: 0.60 (ethyl acetate/hexane=1/1).

$^1$H-NMR ($CDCl_3$) δ: 8.37 (1 H, s), 8.29 (1 H, d, J=9.2 Hz), 8.00 (1 H, br s), 7.57 (1 H, dd, J=1.4 and 9.2 Hz), 4.51 (3 H, s), 3.16 (1 H, quint, J=6.9 Hz), 1.39 (6 H, d, J=6.8 Hz).

Step 3. 8-Isopropyl-1-methyl-1,4-dihydro-9H-pyrazolo[4,3-b]quinolin-9-one

A mixture of 9-chloro-8-isopropyl-1-methyl-1H-pyrazolo[4,3-b]quinoline and 9-chloro-6-isopropyl-1-methyl-1H-pyrazolo[4,3-b]quinoline (EXAMPLE 10, step 2) was treated according to the procedure of step 3 in EXAMPLE 3 instead of 9-chloro-6-fluoro-1-methyl-1H-pyrazolo[4,3-b]quinoline. The title compound and 6-isopropyl-1-methyl-1,4-dihydro-9H-pyrazolo[4,3-b]quinolin-9-one were separable by column chromatography on silica gel eluting with methanol/dichloromethane (1:30).

MS (EI) m/z: 241 ($M^+$).

$^1$H-NMR (DMSO-$d_6$) δ: 7.73 (1 H, s), 7.54 (1 H, dd, J=7.2 and 8.1 Hz), 7.34 (1 H, dd, J=1.1 and 8.1 Hz), 7.13 (1 H, dd, J=1.1 and 7.2 Hz), 5.00–4.94 (1 H, m), 4.29 (3 H, s), 1.24 (6 H, d, J=6.8 Hz). One signal due to NH was not observed.

Example 11
7-BENZYL-1-METHYL-1,4-DIHYDRO-9H-PYRAZOLO[4,3-b]QUINOLIN-9-ONE

Step 1. 4-[(4-Benzylphenyl)amino]-1-methyl-1H-pyrazole-5-carboxylic acid

A mixture of 4-iodo-1-methyl-1H-pyrazole-5-carboxylic acid ((Manaev, Yu. A. et al., *J. Gen. Chem. USSR* (*Engl. Transl.*), 1982, 52 (11), 2291), 8.0 g, 31.74 mmol), 4-benzylaniline (21.03 g, 114.76 mmol) and copper powder (3.2 g) in a mixture of 5% aqueous sodium carbonate (160 ml) and dimethylsulfoxide (80 ml) was stirred for 17 h at 100° C. After cooling to room temperature, the mixture was filtered through a pad of Celite, which was washed with water, 2N aqueous sodium hydroxide and diethyl ether. The separated water layer was washed with diethyl ether (100 ml×2). The water layer was acidified with concentrated hydrochloric acid and the formed solid was collected by filtration, dried, to give 4.86 g (50%) of the pure title compound as a pale brown solid.

Rf value: 0.50 (methanol/dichloromethane/acetic acid=1/10/2 drops).

$^1$H-NMR (DMSO-$d_6$) δ: 7.63 (1 H, s), 7.50 (1 H, br s), 7.31–6.96 (9 H, m), 4.00 (3 H, s), 3.85 (2 H, s). One signal was not observed.

Step 2. 7-Benzyl-9-chloro-1-methyl-1H-pyrazolo[4,3-b]quinoline

A mixture of 4-[(4-benzylphenyl)amino]-1-methyl-1H-pyrazole-5-carboxylic acid (EXAMPLE 11, step 1, 4.86 g, 15.81 mmol) in phosphorus oxychloride (40 ml) was refluxed for 3 h. After cooling to room temperature, the mixture was concentrated and dried in vacuo. The mixture was dissolved in ethyl acetate (300 ml), washed with water (100 ml) and saturated aqueous sodium bicarbonate (100 ml×2) and dried over magnesium sulfate. Removal of solvent gave the dark red residue, which was chromatographed on a column of silica gel eluting with ethyl acetate/hexane (1/3) to afford 3.86 g (79%) of the title compound as a yellow solid.

Rf value: 0.50 (ethyl acetate/hexane=1/2).

$^1$H-NMR (CDCl$_3$) δ: 8.38 (1 H, s), 8.17 (1 H, br s), 8.09 (1 H, d, J=8.9 Hz), 7.54 (1 H, dd, J=1.8 and 8.9 Hz), 7.37–7.24 (5 H, m), 4.51 (3 H, s), 4.24 (2 H, s).

Step 3. 7-Benzyl-1-methyl-1,4-dihydro-9H-pyrazolo[4,3-b]quinolin-9-one

A mixture of 7-benzyl-9-chloro-1-methyl-1H-pyrazolo[4,3-b]quinoline (EXAMPLE 11, step 2, 1.00 g, 3.25 mmol) in 50% aqueous acetic acid (20 ml) was refluxed for 6 h. After cooling to room temperature, the formed solid was collected by filtration to give 905 mg (96%) of the title compound as a white solid.

MS (EI) m/z: 289 (M$^+$).

m.p.: 282° C. (recrystallized from acetic acid/water).

$^1$H-NMR (DMSO-d$_6$) δ: 8.07 (1 H, d, J=1.8 Hz), 7.79 (1 H, s), 7.55 (1 H, dd, J=2.0 and 8.6 Hz), 7.47 (1 H, d, J=8.6 Hz), 7.35–7.16 (5 H, m), 4.29 (3 H, s), 4.06 (2 H, s).

Anal. Calcd. for C$_{18}$H$_{15}$N$_3$O: C, 74.72; H, 5.23; N, 14.52. Found: C, 74.67; H, 5.25; N, 14.41.

Example 12

3-AMINO-1,7-DIMETHYL-1,4-DIHYDRO-9H-PYRAZOLO[4,3-b]QUINOLIN-9-ONE.

Step 1. 1,7-Dimethyl-3-nitro-1,4-dihydro-9H-pyrazolo[4,3-b]quinolin-9-one

A suspension of 4-bromo-1-methyl-3-nitro-1H-pyrazole-5-carboxylic acid ((Y. A. Manaev et al., *J. Gen. Chem. USSR.* (*Engl. Transl.*), 1982, 52, 2991), 11.0 g, 43.9 mmol), p-toluidine (23.5 g, 219 mmol), and copper powder (4.0 g, 63.0 mmol) in 5% aqueous sodium carbonate (200 ml) was stirring at 100° C. for 3 h by mechanical stirrer. After cooling to room temperature, 2N sodium hydroxide (50 ml), water (100 ml), and diethyl ether (300 ml) were added to the mixture. The separated aqueous layer was washed with ether (200 ml), acidified with concentrated hydrochloric acid, and extracted with ethyl acetate (300 ml×2). The combined organic layer was dried over magnesium sulfate, and concentrated in vacuo. To the residue (9.46 g) was added phosphorus oxychloride (90 ml), and the stirring mixture was refluxed for 1 h. After cooling to room temperature, the excess phosphorus oxychloride was removed in vacuo. To the black oily residue (ca. 10 g) was added 50% acetic acid (100 ml) at 0° C., and the mixture was refluxed with stirring for 3 h. After cooling to room temperature, the solvent was removed in vacuo, and the residue was suspended with methanol. The formed solid was collected by filtration to give 5.39 g (48%) of the title compound as a yellow solid.

MS (EI) m/z: 258 (M$^+$).

m.p.: >300° C.

$^1$H-NMR (DMSO-d$_6$) δ: 11.91 (1 H, br s), 8.04 (1 H, br s), 7.97 (1 H, d, J=8.4 Hz), 7.62 (1 H, dd, J=2.2 and 8.6 Hz), 4.43 (3 H, s), 2.44 (3 H, s).

Anal. Calcd. for C$_{12}$H$_{10}$N$_4$O$_3$.0.2H$_2$O: C, 55.05; H, 4.00; N, 21.40. Found: C, 55.11; H, 3.83; N, 21.15.

Step 2. 3-Amino-1,7-dimethyl-1,4-dihydro-9H-pyrazolo[4,3-b]quinolin-9-one

A mixture of 1,7-dimethyl-3-nitro-1,4-dihydro-9H-pyrazolo[4,3-b]quinolin-9-one (EXAMPLE 12, step 1, 4.76 g, 18.4 mmol), iron powder (5.15 g, 92.2 mmol), and ammonium chloride (986 mg, 18.4 mmol) in ethanol (120 ml), water (45 ml), and N,N-dimethylformamide (20 ml) was refluxed for 14 h. After cooling to room temperature, the mixture was filtered through a pad of Celite, which was washed with N,N-dimethylformamide (1.5 l). The filtrate was concentrated in vacuo, and the obtained residue was suspended with methanol. This solid was collected by filtration, and washed with dichloromethane, water and methanol to give 3.60 g (15.8 mmol, 86%) of the title compound as a yellow solid.

MS (EI) m/z: 228 (M$^+$).

m.p.: >300° C.

IR (KBr) ν: 3342, 3198, 1597, 1560, 1528, 1485, 1439, 1394, 1350, 1244, 1146, 957, 810, 667, 552 cm$^{-1}$.

$^1$H-NMR (DMSO-d$_6$) δ: 11.30 (1 H, br s), 8.00 (1 H, br s, 7.50–7.35 (2 H, m), 5.08 (2 H, br s), 4.05 (3H, s), 2.40 (3 H, s).

Anal. Calcd. for C$_{12}$H$_{12}$N$_4$O.0.2H$_2$O: C, 62.16; H, 5.39; N, 24.16. Found: C, 62.11; H, 5.22; N, 24.00.

Example 13

7-(4-CHLOLOBENZYL)-1-METHYL-1,4-DIHYDRO-9H-PYRAZOLO[4,3-b]QUINOLIN-9-ONE.

Step 1. 3-Formyl-4-nitrophenyl trifluoromethanesulfonate

To a solution of 2-nitro-5-hydroxybenzaldehyde (10 g, 60 mmol) in dichloromethane (100 ml), triethylamine (25 ml) and trifluoromethanesulfonic anhydride (12 ml, 69 mmol) were added successively at 0° C. After stirring for 2 h at room temperature, the mixture was poured into water (100 ml) and the organic layer was separated. The separated organic layer was washed with 2N aqueous hydrochloric acid (50 ml), saturated aqueous sodium bicarbonate (50 ml) and dried over magnesium sulfate. Removal of solvent gave 30 g of brown oil, which was chromatographed on a column of silica gel (300 g) eluting with ethyl acetate/hexane (1:1) to afford 14.9 g (83%) of the title compound as a clear yellow oil.

Rf value: 0.25 (ethyl acetate/hexane=1/1).

$^1$H-NMR (CDCl$_3$) δ: 10.44 (1 H, s), 8.29 (1 H, d, J=9.0 Hz), 7.85 (1 H, d, J=2.6 Hz), 7.67 (1 H, dd, J=2.6 and 9.0 Hz).

Step 2. 5-(4-Chlorobenzyl)-2-nitrobenzaldehyde

A mixture of 3-formyl-4-nitrophenyl trifluoromethanesulfonate (EXAMPLE 13, step 1, 3.0 g, 10 mmol), 4-chlorobenzyltributylstannane ((D. Marton et al., *Organometallics,* 1996, 15, 1645), 5.0 g, 12 mmol), dichlorobis(triphenylphosphine)palladium (II) (280 mg, 0.4 mmol) and hexamethylphosphoramide (20 ml) was heated at 100° C. for 15 h. After cooling to room temperature, the mixture was poured into water (100 ml), extracted with diethyl ether (70 ml×2), washed with water (50 ml×2) and dried over magnesium sulfate. Removal of solvent gave 8.5 g of brown tar, which was chromatographed on a column of silica gel (150 g) eluting with ethyl acetate/hexane (1:11) to afford 1.1 g (41%) of the title compound as a pale yellow oil.

Rf value: 0.30 (ethyl acetate/hexane=1/11).

$^1$H-NMR (CDCl$_3$) δ: 10.43 (1 H, s), 8.06 (1 H, d, J=8.4 Hz), 7.73 (1 H, s), 7.61 (1 H, s), 7.50 (1 H, d, J=8.4 Hz), 7.33–7.27 (2 H, m), 7.12–7.09 (2 H, m), 4.09 (2 H, s).

Step 3. [5-(4-Chlorobenzyl)-2-nitrophenyl](4-iodo-1-methyl-1H-pyrazol-5-yl)methanol To a solution of diisopropylamine (0.63 ml, 4.5 mmol) in tetrahydrofuran (10 ml), 1.59M n-butyllithium in hexane (2.8 ml, 4.5 mmol) was added dropwise at −78° C. After stirring for 20 min at 0° C., 4-iodo-1-methyl-1H-pyrazole ((Huettel et al., *Justus Liebigs Ann. Chem.,* 1955, 200), 0.85 g, 4.1 mmol) in tetrahydrofuran (1.0 ml) was added dropwise at −78° C. After stirring for 1 h, 5-(4-chlorobenzyl)-2-nitrobenzaldehyde (EXAMPLE 13, step 2, 1.1 g, 4.1 mmol) in tetrahydrofuran (3.0 ml) was added dropwise at −78° C. After stirring for further 3 h at −78° C., saturated aqueous ammonium chloride (20 ml) was added, extracted with ethyl acetate (50 ml×2) and dried over magnesium sulfate. Removal of solvent gave 2.5 g of yellow oil, which was chromatographed on a column of silica gel (50 g) eluting with ethyl acetate/hexane (5:12) to afford 0.79 g (40%) of the title compound as a white solid.

Rf value: 0.25 (ethyl acetate/hexane=5/12).

$^1$H-NMR (CDCl$_3$) δ: 8.00 (1 H, d, J=9.2 Hz), 7.31 (1 H, s), 7.30–7.25 (4 H, m), 7.06 (1 H, d, J=8.6 Hz), 6.65 (1 H, d, J=5.8 Hz), 4.01 (2 H, s), 3.90 (3 H, s), 2.87 (1 H, d, J=5.8 Hz).

Step 4. [5-(4-Chlorobenzyl)-2-nitrophenyl](4-iodo-1-methyl-1H-pyrazol-5-yl)methanone To a solution of [5-(4-chlorobenzyl)-2-nitrophenyl](4-iodo-1-methyl-1H-pyrazol-5-yl)methanol (EXAMPLE 13, step 3, 0.79 g, 1.6 mmol) in dimethylsulfoxide (10 ml), acetic anhydride (0.31 ml, 3.2 mmol) was added at room temperature. After stirring for 2 days at room temperature, saturated aqueous sodium bicarbonate (30 ml) was added, extracted with diethyl ether (50 ml×2), washed with water (50 ml×2) and dried over magnesium sulfate. Removal of solvent gave 0.9 g of yellow amorphous solid, which was chromatographed on a column of silica gel (50 g) eluting with ethyl acetate/hexane (1:6) to afford 0.64 g (82%) of the title compound as a pale yellow amorphous solid.

Rf value: 0.25 (ethyl acetate/hexane=1/6).

$^1$H-NMR (CDCl$_3$) δ: 8.17 (1 H, d, J=8.6 Hz), 7.50–7.45 (2 H, m), 7.30–7.22 (3 H, m), 7.15–7.10 (2 H, m), 4.29 (3 H, s), 4.05 (2 H, s).

Step 5. [2-Amino-5-(4-chlorobenzyl)phenyl](4-iodo-1-methyl-1H-pyrazol-5-yl)methanone A mixture of [5-(4-chlorobenzyl)-2-nitrophenyl](4-iodo-1-methyl-1H-pyrazol-5-yl)methanone (EXAMPLE 13, step 4, 0.64 g, 1.3 mmol), iron powder (0.37 g, 6.6 mmol) and ammonium chloride (7 mg, 0.13 mmol) in 75% aqueous ethanol (20 ml) was refluxed for 1.5 h. After cooling to room temperature, the mixture was filtered through a pad of Celite and the pad was washed with ethyl acetate (50 ml). The filtrate was concentrated to give yellow solid. The resultant solid was dissolved in ethyl acetate (100 ml), washed with water (50 ml) and dried over magnesium sulfate. Removal of solvent gave 0.54 g (89%) of the title compound as a pale yellow amorphous solid.

Rf value: 0.40 (ethyl acetate/hexane=1/2).

$^1$H-NMR (CDCl$_3$) δ: 7.53 (1 H, s), 7.25–7.20 (2 H, m), 7.15–7.05 (4 H, m), 6.69 (1 H, dd, J=2.4 and 6.6 Hz), 6.31 (2 H, br s), 3.90 (3 H, s), 3.67 (2 H, s).

Step 6. 9-Chloro-7-(4-chlorobenzyl)-1-methyl-1H-pyrazolo[4,3-b]quinoline

A mixture of [2-amino-5-(4-chlorobenzyl)phenyl](4-iodo-1-methyl-1H-pyrazol-5-yl)methanone (EXAMPLE 13, step 5, 0.54 g, 1.2 mmol), copper powder (0.13 g, 25 weight %) and potassium carbonate (0.82 g, 6.0 mmol) in N,N-dimethylformamide (30 ml) was heated at 150° C. for 16 h. After cooling to room temperature, the mixture was filtered through a pad of Celite, which was washed with N,N-dimethylformamide (50 ml). The filtrate was concentrated to give 0.75 g of brown solid. The residue was suspended in phosphorus oxychloride (30 ml) and refluxed for 30 min. After cooling to room temperature, the mixture was concentrated to give brown solid. Water (10 ml) was added to the solid and the mixture was basified with saturated aqueous sodium bicarbonate, extracted with diethyl ether (80 ml×2) and dried over magnesium sulfate. Removal of solvent afforded 0.50 g of brown solid, which was chromatographed on a column of silica gel (50 g) eluting with ethyl acetate/hexane (1:5) to afford 0.13 g (32%) of the title compound as a yellow solid.

Rf value: 0.10 (ethyl acetate/hexane=1/5).

$^1$H-NMR (CDCl$_3$) δ: 8.38 (1 H, s), 8.15 (1 H, s), 8.09 (1 H, d, J=9.0 Hz), 7.50 (1 H, d, J=9.0 Hz), 7.29 (2 H, d, J=8.3 Hz), 7.18 (1 H, d, J=8.3 Hz), 4.51 (3 H, s), 4.21 (2 H, s).

Step 7. 7-(4-Chlorobenzyl)-1-methyl-1,4-dihydro-9H-pyrazolo[4,3-b]quinolin-9-one A suspension of 9-chloro-7-(4-chlorobenzyl)-1-methyl-1H-pyrazolo[4,3-b]quinoline (EXAMPLE 13, step 6, 0.13 g, 0.38 mmol) in 50% aqueous acetic acid (10 ml) was refluxed for 16 h. After cooling to room temperature, water (10 ml) was added. The formed yellow solid was collected by filtration, washed with water (30 ml) and dried in vacuo to afford 0.10 g (81%) of the title compound as a pale yellow solid.

m.p.: >270° C. (recrystallized from acetic acid and water)

IR (KBr) ν: 3261, 3199, 1635, 1593, 1488, 1398, 1317, 804 cm$^{-1}$.

$^1$H-NMR (DMSO-d$_6$) δ: 11.77 (1 H, br s), 8.05 (1 H, d, J=1.5 Hz), 7.89 (1 H, s), 7.53 (1 H, dd, J=2.0 and 8.6 Hz), 7.47 (1 H, d, J=8.6 Hz), 7.35 (2 H, d, J=8.6 Hz), 7.28 (2 H, d, J=8.6 Hz).

Anal. Calcd. for C$_{18}$H$_{14}$ClN$_3$O.0.1H$_2$O: C, 66.26; H, 4.45; N, 12.83. Found: C, 66.40; H, 4.40; N, 12.91.

Example 14

7-(3-CHLOLOBENZYL)-1-METHYL-1,4-DIHYDRO-9H-PYRAZOLO[4,3-b]QUINOLIN-9-ONE.

Step 1. 5-(3-Chlorobenzyl)-2-nitrobenzaldehyde.

The title compound was prepared according to the procedure of step 2 in the EXAMPLE 13 using 3-chlorobenzyltributylstannane (D. Marton et al., Organometallics, 1996, 15, 1645), instead of 4-chlorobenzyltributylstannane.

Rf value: 0.50 (ethyl acetate/hexane=1/6).

$^1$H-NMR (CDCl$_3$) δ: 10.43 (1 H, s), 8.07 (1 H, d, J=8.4 Hz), 7.74 (1 H, d, J=2.0 Hz), 7.51 (1 H, dd, J=2.0 and 8.4 Hz), 7.28–7.23 (2 H, m), 7.15 (1 H, s), 7.08–7.04 (1 H, m).

Step 2. [5-(3-Chlorobenzyl)-2-nitrophenyl](4-iodo-1-methyl-1H-pyrazol-5-yl)methanol The title compound was prepared according to the procedure of step 3 in EXAMPLE 13 using 5-(3-chlorobenzyl)-2-nitrobenzaldehyde (EXAMPLE 14, step 1) instead of 5-(4-chlorobenzyl)-2-nitrobenzaldehyde.

Rf value: 0.40 (ethyl acetate/hexane=1/1).

$^1$H-NMR (CDCl$_3$) δ: 8.01 (1 H, d, J=8.8 Hz), 7.41 (1 H, s), 7.33–7.20 (4 H, m), 6.91 (1 H, m), 7.01 (1 H, s), 6.65 (1 H, d, J=6.0 Hz), 4.01 (2 H, s), 3.93 (3 H, s), 3.08 (1 H, d, J=6.0 Hz).

Step 3. [5-(3-Chlorobenzyl)-2-nitrophenyl](4-iodo-1-methyl-1H-pyrazol-5-yl)methanone The title compound was prepared according to the procedure of step 4 in EXAMPLE 13 using [5-(3-chlorobenzyl)-2-nitrophenyl](4-iodo-1-methyl-1H-pyrazol-5-yl)methanol (EXAMPLE 14, step 2), instead of [5-(4-chlorobenzyl)-2-nitrophenyl](4-iodo-1-methyl-1H-pyrazol-5-yl)methanol.

Rf value: 0.25 (ethyl acetate/hexane=1/6).

$^1$H-NMR (CDCl$_3$) δ: 8.18 (1 H, d, J=8.4 Hz), 7.52–7.47 (2 H, m), 7.32 (1 H, s), 7.26–7.24 (2 H, m), 7.17 (1 H, s), 7.10–7.07 (1 H, m), 4.30 (3 H, s), 4.10 (2 H, s).

Step 4. [2-Amino-5-(3-chlorobenzyl)phenyl](4-iodo-1-methyl-1H-pyrazol-5-yl)methanone The title compound was prepared according to the procedure of step 5 in EXAMPLE 13 using [5-(3-chlorobenzyl)-2-nitrophenyl](4-iodo-1-methyl-1H-pyrazol-5-yl)methanone (EXAMPLE 14, step 3), instead of [5-(4-chlorobenzyl)-2-nitrophenyl](4-iodo-1-methyl-1H-pyrazol-5-yl)methanone.

Rf value: 0.15 (ethyl acetate/hexane=1/6).

$^1$H-NMR (CDCl$_3$) δ: 7.53 (1 H, s), 7.22–7.14 (5 H, m), 7.05–7.02 (1 H, m), 6.72–6.67 (1 H, m), 6.32 (2 H, br s), 3.90 (3 H, s), 3.75 (2 H, s).

Step 5. 9-Chloro-7-(3-chlorobenzyl)-1-methyl-1H-pyrazolo,4.3-b]quinoline

The title compound was prepared according to the procedure of step 6 in EXAMPLE 13 using [2-amino-5-(3-chlorobenzyl)phenyl](4-iodo-1-methyl-1H-pyrazol-5-yl)methanone (EXAMPLE 14, step 4), instead of [2-amino-5-(4-chlorobenzyl)phenyl](4-iodo-1-methyl-1H-pyrazol-5-yl)methanone.

Rf value: 0.52 (ethyl acetate/hexane=1/3).

$^1$H-NMR (CDCl$_3$) δ: 8.39 (1 H, s), 8.16 (1 H, s), 8.11 (1 H, d, J=8.9 Hz), 7.50 (1 H, dd, J=2.0 and 8.9 Hz), 7.27–7.21 (3 H, m), 7.17–7.14 (1 H, m), 4.51 (3 H, s), 4.21 (2 H, s).

Step 6. 7-(3-Chlorobenzyl)-1-methyl-1,4-dihydro-9H-pyrazolo[4,3-b]quinolin-9-one The title compound was prepared according to the procedure of step 7 in EXAMPLE 13 using 9-chloro-7-(3-chlorobenzyl)-1-methyl-1H-pyrazolo[4,3-b]quinoline (EXAMPLE 14, step 5), instead of 9-chloro-7-(4-chlorobenzyl)-1-methyl-1H-pyrazolo[4,3-b]quinoline.

m.p.: 263° C. (recrystallized from acetic acid and water)

IR (KBr) v: 3263, 3201, 1589, 1541, 1488, 696 cm$^{-1}$.

$^1$H-NMR (CDCl$_3$) δ: 8.08 (1 H, s), 7.79 (1 H, s), 7.55 (1 H, dd, J=2.2 and 8.6 Hz), 7.48 (1 H, d, J=8.6 Hz), 7.38–7.22 (4 H, m), 4.30 (3 H, s), 4.08 (2 H, s).

Anal. Calcd. for C$_{18}$H$_{14}$ClN$_3$O: C, 66.77; H, 4.36; N, 12.98. Found: C, 66.68; H, 4.40; N, 12.96.

Example 15

7-(2-CHLOROBENZYL)-1-METHYL-1,4-DIHYDRO-9H-PYRAZOLO[4,3-b]QUINOLIN-9-ONE.

Step 1. 5-(2-Chlorobenzyl)-2-nitrobenzaldehyde

The title compound was prepared according to the procedure of step 2 in EXAMPLE 13 using 2-chlorobenzyltributylstannane (D. Marton et al., *Organometallics*, 1996, 15, 1645), instead of 4-chlorobenzyltributylstannane.

Rf value: 0.50 (ethyl acetate/hexane=1/6).

$^1$H-NMR (CDCl$_3$) δ: 10.43 (1 H, s), 8.05 (1 H, d, J=8.4 Hz), 7.74 (1 H, s), 7.52–7.50 (1 H, m), 7.42–7.38 (1 H, m), 7.29–7.20 (3 H, m), 4.24 (2 H, s).

Step 2. [5-(2-Chlorobenzyl)-2-nitrophenyl](4-iodo-1-methyl-1H-pyrazol-5-yl)methanol The title compound was prepared according to the procedure of step 3 in EXAMPLE 13 using 5-(2-chlorobenzyl)-2-nitrobenzaldehyde (EXAMPLE 15, step 1), instead of 5-(4-chlorobenzyl)-2-nitrobenzaldehyde.

Rf value: 0.15 (ethyl acetate/hexane=1/3).

$^1$H-NMR (CDCl$_3$) δ: 7.97 (1 H, d, J=8.3 Hz), 7.40–7.12 (7 H, m), 6.64 (1 H, d, J=5.9 Hz), 4.15 (2 H, s), 3.83 (3 H, s), 3.31 (1 H, br s).

Step 3. [5-(2-Chlorobenzyl)-2-nitrophenyl](4-iodo-1-methyl-1H-pyrazol-5-yl)methanone The title compound was prepared according to the procedure of step 4 in EXAMPLE 13 using [5-(2-chlorobenzyl)-2-nitrophenyl](4-iodo-1-methyl-1H-pyrazol-5-yl)methanol (EXAMPLE 15, step 2) instead of [5-(4-chlorobenzyl)-2-nitrophenyl](4-iodo-1-methyl-1H-pyrazol-5-yl)methanol.

Rf value: 0.20 (ethyl acetate/hexane=1/6).

$^1$H-NMR (CDCl$_3$) δ: 8.16 (1 H, d, J=8.6 Hz), 7.50 (1 H, dd, J=2.0 and 8.6 Hz), 7.45 (1 H, s), 7.42–7.37 (1 H, m), 7.31 (1 H, d, J=1.8 Hz), 7.27–7.22 (3 H, s), 4.28 (3 H, s), 4.25 (2 H, s).

Step 4. [2-Amino-5-(2-chlorobenzyl)phenyl](4-iodo-1-methyl-1H-pyrazol-5-yl)methanone The title compound was prepared according to the procedure of step 5 in EXAMPLE 13 using [5-(2-chlorobenzyl)-2-nitrophenyl](4-iodo-1-methyl-1H-pyrazol-5-yl)methanone (EXAMPLE 15, step 3), instead of [5-(4-chlorobenzyl)-2-nitrophenyl](4-iodo-1-methyl-1H-pyrazol-5-yl)methanone.

Rf value: 0.40 (ethyl acetate/hexane=1/4).

$^1$H-NMR (CDCl$_3$) δ: 7.51 (1 H, s), 7.36–7.30 (1 H, m), 7.22–7.12 (5 H, m), 6.68 (1 H, d, J=8.6 Hz), 6.30 (2 H, br s), 3.93 (2 H, s), 3.86 (3 H, s).

Step 5. 9-Chloro-7-(2-chlorobenzyl)-1-methyl-1H-pyrazolo[4,3-b]quinoline

The title compound was prepared according to the procedure of step 6 in EXAMPLE 13 using [2-amino-5-(2-chlorobenzyl)phenyl](4-iodo-1-methyl-1H-pyrazol-5-yl)methanone (EXAMPLE 15, step 4), instead of [2-amino-5-(4-chlorobenzyl)phenyl](4-iodo-1-methyl-1H-pyrazol-5-yl)methanone.

Rf value: 0.20 (ethyl acetate/hexane=1/6).

$^1$H-NMR (CDCl$_3$) δ: 8.39 (1 H, s), 8.16 (1 H, d, J=1.1 Hz), 8.11 (1 H, d, J=8.8 Hz), 7.56 (1 H, dd, J=2.0 and 8.8 Hz), 7.44–7.40 (1 H, m), 7.27–7.20 (3 H, m), 4.50 (3 H, s), 4.37 (2 H, s).

Step 6. 7-(2-Chlorobenzyl)-1-methyl-1,4-dihydro-9H-pyrazolo[4,3-b]quinolin-9-one The title compound was prepared according to the procedure of step 7 in EXAMPLE 13 using 9-chloro-7-(2-chlorobenzyl)-1-methyl-1H-pyrazolo[4,3-b]quinoline (EXAMPLE 15, step 5), instead of 9-chloro-7-(4-chlorobenzyl)-1-methyl-1H-pyrazolo[4,3-b]quinoline.

m.p.: 278° C. (recrystallized from acetic acid and water)

$^1$H-NMR (CDCl$_3$) δ: 11.70 (1 H, br s), 8.01 (1 H, s), 7.78 (1 H, s), 7.55–7.25 (7 H, m), 4.28(3 H, s), 4.19(2 H, s).

Anal. Calcd. for C$_{18}$H$_{14}$ClN$_3$O: C, 66.77; H, 4.36; N, 12.98. Found: C, 66.78; H, 4.40; N, 12.93.

Example 16

7-(4-METHOXYBENZYL)-1-METHYL-1,4-DIHYDRO-9H-PYRAZOLO[4,3-b]QUINOLIN-9-ONE.

Step 1. 5-(4-Methoxybenzyl)-2-nitrobenzaldehyde

The title compound was prepared according to the procedure of step 2 in EXAMPLE 13 using 4-methoxybenzyltributylstannane (A. Hormoz et al., *J. Organomet. Chem.*, 1981, 215, 49), instead of 4-chlorobenzyltributylstannane.

Rf value: 0.25 (ethyl acetate/hexane=1/10).

$^1$H-NMR (CDCl$_3$) δ: 10.42 (1 H, s), 8.04 (1 H, d, J=8.4 Hz), 7.73 (1 H, d, J=2.0 Hz), 7.50 (1 H, dd, J=2.0 and 8.4 Hz), 7.08 (2 H, d, J=6.6 Hz), 6.85 (2 H, d, J=6.6 Hz).

Step 2. [5-(4-Methoxybenzyl)-2-nitrophenyl](4-iodo-1-methyl-1H-pyrazol-5-yl)methanol The title compound was prepared according to the procedure of step 3 in EXAMPLE 13 using 5-(4-methoxybenzyl)-2-nitrobenzaldehyde (EXAMPLE 16, step 1), instead of 5-(4-chlorobenzyl)-2-nitrobenzaldehyde.

Rf value: 0.25 (ethyl acetate/hexane=1/2).

$^1$H-NMR (CDCl$_3$) δ: 7.97 (1 H, d, J=8.2 Hz), 7.41 (1 H, s), 7.31–7.24 (2 H, m), 7.06–7.02 (2 H, m), 6.86–6.80 (2 H, m), 6.64 (1 H, d, J=6.0 Hz), 3.97 (2 H, s), 3.87 (3 H, s), 3.79 (3 H, s), 3.10 (1 H, d, J=6.0 Hz).

Step 3. [5-(4-Methoxybenzyl)-2-nitrophenyl](4-iodo-1-methyl-1H-pyrazol-5-yl)methanone The title compound was prepared according to the procedure of step 4 in the EXAMPLE 13 using [5-(4-methoxybenzyl)-2-nitrophenyl](4-iodo-1-methyl-1H-pyrazol-5-yl)methanol (EXAMPLE 16, step 2), instead of [5-(4-chlorobenzyl)-2-nitrophenyl](4-iodo-1-methyl-1H-pyrazol-5-yl)methanol.

Rf value: 0.25 (ethyl acetate/hexane=1/6).

$^1$H-NMR (CDCl$_3$) δ: 8.14 (1 H, d, J=8.4 Hz), 7.50–7.45 (2 H, m), 7.30 (1 H, d, J=2.0 Hz), 7.12–7.08 (2 H, m), 6.87–6.82 (2 H, m), 4.29 (3 H, s), 4.08 (2 H, s), 3.79 (3 H, s).

Step 4. [2-Amino-5-(4-methoxybenzyl)phenyl](4-iodo-1-methyl-1H-pyrazol-5-yl)methanone The title compound was prepared according to the procedure of step 5 in EXAMPLE 13 using [5-(4-methoxybenzyl)-2-nitrophenyl](4-iodo-1-methyl-1H-pyrazol-5-yl)methanone (EXAMPLE 16, step 3), instead of [5-(4-chlorobenzyl)-2-nitrophenyl](4-iodo-1-methyl-1H-pyrazol-5-yl)methanone.

Rf value: 0.45 (ethyl acetate/hexane=1/2).

$^1$H-NMR (CDCl$_3$) δ: 7.53–7.50 (1 H, m), 7.26–7.23 (1 H, m), 7.17–7.04 (3 H, s), 6.82–6.78 (2 H, m), 6.69–6.65 (1 H, m), 6.28 (2 H, br s), 3.88 (3 H, s), 3.77 (2 H, s), 3.75 (3 H, s).

Step 5. 9-Chloro-7-(4-methoxybenzyl)-1-methyl-1H-pyrazolo[4,3-b]quinoline

The title compound was prepared according to the procedure of step 6 in EXAMPLE 13 using [2-amino-5-(4-methoxybenzyl)phenyl](4-iodo-1-methyl-1H-pyrazol-5-yl)methanone (EXAMPLE 16, step 4), instead of [2-amino-5-(4-chlorobenzyl)phenyl](4-iodo-1-methyl-1H-pyrazol-5-yl)methanone.

Rf value: 0.25 (ethyl acetate/hexane=1/5).

$^1$H-NMR (CDCl$_3$) δ: 8.38 (1 H, s), 8.15 (1 H, s), 8.08 (1 H, d, J=9.0 Hz), 7.52 (1 H, d, J=9.0 Hz), 7.17 (2 H, d, J=8.8 Hz), 6.86 (2 H, d, J=8.8 Hz), 4.50 (3 H, s), 4.18 (2 H, s), 3.80 (3 H, s).

Step 6. 7-(4-Methoxybenzyl)-1-methyl-1,4-dihydro-9H-pyrazolo[4,3-b]quinolin-9-one The title compound was prepared according to the procedure of step 7 in EXAMPLE 13 using 9-chloro-7-(4-methoxybenzyl)-1-methyl-1H-pyrazolo[4,3-b]quinoline (EXAMPLE 16, step 5), instead of 9-chloro-7-(4-chlorobenzyl)-1-methyl-1H-pyrazolo[4,3-b]quinoline.

m.p.: 248–249° C. (recrystallized from acetic acid and water)

IR (KBr) ν: 3267, 3205, 1589, 1541, 1510, 1488, 1431, 1247, 1028, 790 cm$^{-1}$.

$^1$H-NMR (CDCl$_3$) δ: 11.75 (1 H, br s), 8.03 (1 H, d, J=1.8 Hz), 7.79 (1 H, s), 7.52 (1 H, dd, J=2.2 and 8.8 Hz), 7.46 (1 H, d, J=8.6 Hz), 7.16 (1 H, d. J=8.6 Hz), 6.89–6.85 (1 H, m), 4.29 (3 H, s), 3.99 (2 H, s), 3.72 (3 H, s).

Anal. Calcd. for C$_{19}$H$_{17}$N$_3$O$_2$.0.1H$_2$O: C, 71.06; H, 5.40; N, 13.08. Found: C, 71.08; H, 5.32; N, 13.03.

Example 17

SODIUM 4-[[1-METHYL-1,4-DIHYDRO-9H-PYRAZOLO[4,3-b]QUINOLIN-9-ONE]-7-YL-METHYL]PHENOXIDE.

Step 1. 7-(4-Hydroxybenzyl)-1-methyl-1,4-dihydro-9H-pyrazolo[4,3-b]quinolin-9-one A mixture of 7-(4-methoxybenzyl)-1-methyl-1,4-dihydro-9H-pyrazolo[4,3-b]quinolin-9-one (EXAMPLE 16, step 6, 500 mg, 1.57 mmol), 47% aqueous hydrobromic acid (20 ml) and acetic acid (20 ml) was heated at reflux temperature for 2 h. After cooling to room temperature, water (40 ml) was added. The formed pale yellow solid was collected by filtration, washed with water (50 ml) and diethyl ether (50 ml) to give 470 mg (98%) of the title compound as a pale yellow solid.

Rf value: 0.30 (ethyl acetate/hexane=1/2).

$^1$H-NMR (DMSO-d$_6$) δ: 11.74 (1 H, br s), 9.20 (1 H, br s), 8.02 (1 H s), 7.78 (1 H, s), 7.51 (1 H, dd, J=2.1 and 8.7 Hz), 7.44 (1 H, d, J=8.7 Hz), 7.03 (2 H, d, J=8.4 Hz), 6.68 (2 H, d, J=8.4 Hz), 4.29 (3 H, s), 3.93 (2 H, s).

Step 2. Sodium 4-[[1-Methyl-1,4-dihydro-9H-pyrazolo[4,3-b]quinolin-9-one]-7-yl-methyl]phenoxide To a solution of 7-(4-hydroxybenzyl)-1-methyl-1,4-dihydro-9H-pyrazolo[4,3-b]quinolin-9-one (EXAMPLE 17, step 1, 159 mg, 0.52 mmol) in ethanol (15 ml) and tetrahydrofuran (5 ml), 2N aqueous sodium hydroxide (0.26 ml) was added at room temperature. After stirring for 2 h, removal of solvent gave pale yellow solid. The residual solid was washed with in diethyl ether (5 ml) and ethanol (0.5 ml) to give 158 mg (98%) of the title compound as a pale yellow solid.

m.p.: >250° C.

IR (KBr) ν: 3205, 1591, 1544, 1431, 1396, 1365, 1319, 1215 cm$^{-1}$.

$^1$H-NMR (DMSO-d$_6$) δ: 7.99 (1 H, s), 7.71 (1 H, s), 7.42 (1 H, d, J=8.6 Hz), 7.31 (1 H, dd, J=2.0 and 8.6 Hz), 7.02 (2 H, d, J=7.9 Hz), 6.67 (2 H, d, J=7.9 Hz), 4.28 (3 H, s), 3.89 (2 H, s).

Anal. Calcd. for C$_{18}$H$_{14}$N$_3$O$_2$Na.0.15H$_2$O: C, 69.58; H, 5.06; N, 13.52. Found: C, 69.55; H, 4.99; N, 13.53.

Example 18

7-[4-[2-(DIMETHYLAMINO)ETHOXY]BENZYL]-1-METHYL-1,4-DIHYDRO-9H-PYRAZOLO[4,3-b]QUINOLIN-9-ONE HYDROCHLORIDE.

Step 1. 9-Chloro-7-(4-hydroxybenzyl)-1-methyl-1H-pyrazolo[4,3-b]quinoline

To a suspension of 7-(4-methoxybenzyl)-1-methyl-1,4-dihydro-9H-pyrazolo[4,3-b]quinolin-9-one (EXAMPLE 17, step 1, 95 mg, 0.31 mmol) in oxalylchloride (2.5 ml) was added 1 drop of N,N-dimethylformamide at room temperature and the mixture was refluxed for 30 min. After cooling to room temperature, the mixture was concentrated in vacuo to give a yellow residue. The residue was basified with saturated aqueous sodium bicarbonate, washed with ethyl acetate (30 ml×2). Water phase was acidified with 2N aqueous hydrochloric acid (pH: ~5) to give a yellow solid, which was collected by filtration, washed with isopropyl alcohol (20 ml) and diethyl ether (10 ml) to afford 74 mg (74%) of the title compound as a pale yellow solid.

Rf value: 0.50 (ethyl acetate/hexane=1/2).

$^1$H-NMR (DMSO-d$_6$) δ: 8.59 (1 H, s), 8.22 (1 H, s), 8.10 (1 H, d, J=8.7 Hz), 7.68 (1 H, d, J=8.7 Hz), 7.42 (2 H, d, J=8.6 Hz), 7.19 (2 H, d, J=8.6 Hz), 4.35 (3 H, s), 4.29 (2 H, s).

Step 2. 7-[4-[2-(Dimethylamino)ethoxy]benzyl)-9-chloro-1-methyl-1H-pyrazolo[4,3-b]quinoline A mixture of 9-chloro-7-(4-hydroxybenzyl)-1-methyl-1H-pyrazolo[4,3-b]quinoline (EXAMPLE 18, step 1, 74 mg, 0.23 mmol), dimethylaminoethyl chloride hydrochloride (40 mg, 0.27 mmol) and potassium carbonate (160 mg, 1.15 mmol) in N,N-dimethylformamide (5 ml) was heated at 80° C. for 5 h. After cooling to room temperature, the mixture was poured into water (30 ml), extracted with ethyl acetate (50 ml×2), washed with water (30 ml×2), brine (30 ml) and dried over magnesium sulfate. Removal of solvent gave 130 mg of brown oil, which was chromatographed on a column of silica gel (30 g) eluting with methanol/dichloromethane (1:14) to afford 28 mg (31%) of the title compound as a pale yellow solid.

Rf value: 0.25 (methanol/dichloromethane=1/14).
$^1$H-NMR (DMSO-d$_6$) δ: 8.59 (1 H, s), 8.16 (1 H, s), 8.10–8.04 (1 H, m), 7.65–7.60 (1 H, m), 7.22 (2 H, d, J=8.6 Hz), 6.88 (2 H, d, J=8.6 Hz), 4.24 (3 H, s), 4.17 (2 H, s), 4.02–3.98 (2 H, m), 2.62–2.58 (2 H, m), 2.18 (6 H, s).

Step 3. 7-[4-[2-(Dimethylamino)ethoxy]benzyl]-1-methyl-1,4-dihydro-9H-pyrazolo]4,3-b]quinolin-9-one hydrochloride 7-[4-(2-(Dimethylamino)ethoxy)benzyl]-1-methyl-1,4-dihydro-9H-pyrazolo[4,3-b]quinolin-9-one was prepared according to the procedure of step 3 in EXAMPLE 11 using 7-[4-[2-(dimethylamino)ethoxy]benzyl]-9-chloro-1-methyl-1H-pyrazolo[4,3-b]-quinoline (Example 18, step 2), instead of 7-benzyl-9-chloro-1-methyl-1H-pyrazolo[4,3-b]quinoline. 7-[4-(2-(Dimethylamino)ethoxy)benzyl]-1-methyl-1,4-dihydro-9H-pyrazolo[4,3-b]quinolin-9-one (18 mg, 0.048 mmol) was treated with methanolic hydrochloric acid (5 ml) and the mixture was evaporated to give a yellow solid. The solid was recrystallized from 2-propanol and diethyl ether to afford 7 mg (27%) of the titled compound as a pale yellow solid.

m.p.: 235–240° C. (recrystallized from isopropyl alcohol and diethyl ether).
MS (EI) m/z: 376 (M$^+$).
IR (KBr) ν: 3265, 1633, 1589, 1398, 1242, 813 cm$^{-1}$.
$^1$H-NMR (DMSO-d$_6$) δ: 11.83 (1 H, s), 9.95–9.80 (1 H, br s), 8.02 (1 H, d, J=1.7 Hz), 7.79 (1 H, s), 7.54 (1 H, dd, J=2.0 and 8.6 Hz), 7.48 (1 H, d, J=8.4 Hz), 7.22 (1 H, d, J=8.6 Hz), 6.95 (1 H, d, J=8.6 Hz), 4.35–4.25 (5 H, m), 4.01 (2 H, s), 3.55–3.45 (2 H, m), 2.84 (6 H, s).

Example 19
7-(3-METHOXYBENZYL)-1-METHYL-1,4-DIHYDRO-9H-PYRAZOLO[4,3-b]QUINOLIN-9-ONE. Step 1. 4-[(4-Bromophenyl)amino]-1-methyl-1H-pyrazole-5-carboxylic acid The title compound was prepared according to the procedure of step 1 in EXAMPLE 1 (CJ-022,998) using 4-bromoaniline, instead of 4-fluoroaniline.
Rf value: 0.15 (methanol/dichloromethane=1/9).
$^1$H-NMR (DMSO-d$_6$) δ: 7.65 (1 H, s), 7.34 (2 H, d, J=8.9 Hz), 7.01 (2 H, d, J=8.9 Hz), 4.02 (3 H, s). Two signals due to NH and CO$_2$H were not observed.

Step 2. 7-Bromo-9-chloro-1-methyl-1H-pyrazolo[4,3-b]quinoline

The title compound was prepared according to the procedure of step 2 in EXAMPLE 3 (CJ-023,024) using 4-[(4-bromophenyl)amino]-1-methyl-1H-pyrazole-5-carboxylic acid (EXAMPLE 19, step 1), instead of 4-[(3-fluorophenyl)amino]-1-methyl-1H-pyrazole-5-carboxylic acid.
Rf value: 0.23 (ethyl acetate/hexane=1/3).
$^1$H-NMR (DMSO-d$_6$) δ: 8.54 (1 H, d, J=2.2 Hz), 8.41 (1 H, s), 8.06 (1 H, d, J=9.2 Hz), 7.57 (1 H, dd, J=2.2 and 9.2 Hz), 4.52 (3 H, s).

Step 3. 9-Chloro-7-(3-methoxybenzyl)-1-methyl-1H-pyrazolo[4,3-b]quinoline

A mixture of 7-bromo-9-chloro-1-methyl-1H-pyrazolo[4,3-b]quinoline (EXAMPLE 19, step 2, 0.20 g, 0.67 mmol), 3-methoxybenzyltributylstannane ((A. Hormoz et al., J. Organomet. Chem., 1981, 215, 49), 0.27 g, 0.67 mmol), dichlorobis(triphenylphosphine)palladium (II) (50 mg, 0.07 mmol) and hexamethylphosphoramide (5 ml) was heated at 100° C. for 6 h. After cooled to room temperature, the mixture was poured into water (100 ml), extracted with diethyl ether (70 ml×2), washed with water (50 ml×2) and dried over magnesium sulfate. Removal of solvent gave 0.23 g of blown oil, which was chromatographed on a column of silica gel (30 g) eluting with ethyl acetate/hexane (1:5) to afford 0.18 g (79%) of the title compound as a pale yellow solid Rf value: 0.25 (ethyl acetate/hexane=1/5).
$^1$H-NMR (CDCl$_3$) δ: 8.38 (1 H, s), 8.16 (1 H, d, J=0.8 Hz), 8.08 (1 H, d, J=9.0 Hz), 7.53 (1 H, dd, J=1.8 and 9.0 Hz), 7.24 (1 H, dd, 1.3 and 2.4 Hz), 6.85 (1 H, d, J=7.9 Hz), 6.80–6.75 (2 H, m), 4.50 (3 H, s), 4.21 (2 H, s), 3.78 (3 H, s).

Step 4. 7-(2-Methoxybenzyl)-1-methyl-1,4-dihydro-9H-pyrazolo[4,3-b]quinolin-9-one The title compound was prepared according to the procedure of step 7 in EXAMPLE 13 using 9-chloro-7-(3-methoxybenzyl)-1-methyl-1H-pyrazolo[4,3-b]quinoline (EXAMPLE 19, step 1), instead of 9-chloro-7-(4-chlorobenzyl)-1-methyl-1H-pyrazolo[4,3-b]quinoline.

m.p.: 246–250° C. (recrystallized from acetic acid and water)
IR (KBr) ν: 3150, 1591, 1541, 1489, 1456, 1255, 1100 cm$^{-1}$.
$^1$H-NMR (DMSO-d$_6$) δ: 8.06 (1 H, d, J=1.7 Hz), 7.79 (1 H, s), 7.55 (1 H, dd, J=1.7 and 8.6 Hz), 7.47 (1 H, d, J=8.6 Hz), 7.25–7.17 (1 H, m), 6.85–6.75 (3 H, s), 4.29 (3 H, s), 4.03 (2 H, s), 3.72 (3 H, s).

Example 20
7-(3-HYDROXYBENZYL)-1-METHYL-1,4-DIHYDRO-9H-PYRAZOLO[4,3-b]QUINOLIN-9-ONE.

The title compound was prepared according to the procedure of step 1 in EXAMPLE 17 using 7-(3-methoxybenzyl)-1-methyl-1,4-dihydro-9H-pyrazolo[4,3-b]quinolin-9-one (EXAMPLE 19, step 4), instead of 7-(2-methoxybenzyl)-1-methyl-1,4-dihydro-9H-pyrazolo[4,3-b]quinolin-9-one.

m.p.: >270° C. (recrystallized from acetic acid and water)
IR (KBr) ν: 3101, 1635, 1591, 1539, 1487, 1456, 1244, 1151, 825, 752, 698 cm$^{-1}$.
$^1$H-NMR (DMSO-d$_6$) δ: 9.29 (1 H, br s), 8.06 (1 H, s), 7.79 (1 H, s), 7.52 (1 H, dd, J=2.1 and 8.7 Hz), 7.47 (1 H, d, J=8.6 Hz), 7.09 (1 H, t, J=7.6 Hz), 6.68 (1 H, d, J=7.6 Hz), 6.62–6.55 (1 H, m), 4.30 (3 H, s), 3.96 (2 H, s).
Anal. Calcd. for $C_{18}H_{15}N_3O_2 \cdot H_2O$: C, 66.86; H, 5.30; N, 13.00. Found: C, 66.77; H, 5.32; N, 12.98.

Example 21
7-(2-METHOXYBENZYL)-1-METHYL-1,4-DIHYDRO-9H-PYRAZOLO[4,3-b]QUINOLIN-9-ONE.
Step 1. 5-(2-Methoxybenzyl)-2-nitrobenzaldehyde The title compound was prepared according to the procedure of step 2 in EXAMPLE 13 using 2-methoxybenzyltributylstannane* instead of 4-chlorobenzyltributylstannane.
Rf value: 0.45 (ethyl acetate/hexane=1/11).
$^1$H-NMR (CDCl$_3$) δ: 10.40 (1 H, s), 8.00 (1 H, d, J=8.2 Hz), 7.77 (1 H, d, J=1.9 Hz), 7.56–7.51 (1 H, m), 7.29–7.23 (1 H, m), 7.15–7.12 (1 H m), 6.98–6.86 (2 H, m), 4.08 (2 H, s), 3.80 (3 H, s).

* 2-methoxybenzyltributylstannane

To a suspension of tributyltin chloride (5.8 ml, 21.5 mmol) and zinc powder (2.8 g, 43 mmol) in tetrahydrofuran (20 ml) and saturated ammonium chloride (40 ml), 2-methoxybenzyl bromide ((D. S. Naraimhan et al., J. Heterocycl. Chem., 1997, 34, 835), 8.6 g, 43 mmol) was added dropwise on an ice bath at a rate sufficient to maintain a gentle reflux due to the exothermicity of the reaction. After addition, the ice bath was removed and the stirring was continued for 1 h. The organic layer was separated and concentrated. Purification by column chromatography on a column of silica gel eluting with hexane to give 5.26 g (30%) of the title compound as a clear colorless oil.
Rf value: 0.90 (hexane).
hu 1H-NMR (CDCl$_3$) δ: 7.01–6.96 (2 H, m), 6.81–6.72 (2 H, m), 3.78 (3 H, s), 2.22 (2 H, t, J=29 Hz), 1.46–1.35 (6 H, m), 1.31–1.17 (6 H, m), 0.85 (9 H, t, J=7.2 Hz), 0.77–0.71 (6 H, m).

Step 2. [5-(2-Methoxybenzyl)-2-nitrophenyl](4-iodo-1-methyl-1H-pyrazol-5-yl)methanol The title compound was prepared according to the procedure of step 3 in EXAMPLE 13 using 5-(2-methoxybenzyl)-2-nitrobenzaldehyde (EXAMPLE 21, step 1), instead of 5-(4-chlorobenzyl)-2-nitrobenzaldehyde.
Rf value: 0.25 (ethyl acetate/hexane=1/2).
$^1$H-NMR (CDCl$_3$) δ: 7.95 (1 H, d, J=8.2 Hz), 7.41 (1 H, s), 7.35–7.31 (1 H, m), 7.24–7.21 (1 H, m), 7.15 (1 H, d, J=1.5 Hz), 7.08 (1 H, dd, J=1.7 and 7.5 Hz), 6.92–6.83 (2 H, m), 6.63 (1 H, d, J=5.7 Hz), 3.99 (2 H, s), 3.78 (3 H, s), 3.70 (3 H, s), 3.41 (1 H, d J=5.7 Hz).

Step 3. [5-(2-Methoxybenzyl)-2-nitrophenyl](4-iodo-1-methyl-1H-pyrazol-5-yl)methanone The title compound was prepared according to the procedure of step 4 in EXAMPLE 13 using [5-(2-methoxybenzyl)-2-nitrophenyl](4-iodo-1-methyl-1H-pyrazol-5-yl)methanol (EXAMPLE 21, step 2), instead of [5-(4-chlorobenzyl)-2-nitrophenyl](4-iodo-1-methyl-1H-pyrazol-5-yl)methanol.
Rf value: 0.65 (ethyl acetate/hexane=1/2).
$^1$H-NMR (CDCl$_3$) δ: 8.12 (1 H, d, J=8.4 Hz), 7.51 (1 H, dd, J=1.8 and 8.4 Hz), 7.45 (1 H, s), 7.34 (1 H, d, J=2.0 Hz), 7.25 (1 H, dd, J=1.7 and 9.2 Hz), 7.15 (1 H, dd, J=1.7 and 7.3 Hz), 6.94–6.85 (2 H, m), 4.28 (3 H, s), 4.17 (2 H, s), 3.80 (3 H, s).

Step 4. [2-Amino-5-(2-methoxybenzyl)phenyl](4-iodo-1-methyl-1H-pyrazol-5-yl)methanone The title compound was prepared according to the procedure of step 5 in EXAMPLE 13 using [5-(2-methoxybenzyl)-2-nitrophenyl](4-iodo-1-methyl-1H-pyrazol-5-yl)methanone (EXAMPLE 21, step 3), instead of [5-(4-chlorobenzyl)-2-nitrophenyl](4-iodo-1-methyl-1H-pyrazol-5-yl)methanone.
Rf value: 0.40 (ethyl acetate/hexane=1/2).
$^1$H-NMR (CDCl$_3$) δ: 7.52 (1 H, s), 7.25–7.14 (3 H, m), 7.03 (1 H, d, J=7.4 Hz), 6.87–6.81 (2 H, m), 6.65 (1 H, d, J=8.4 Hz), 6.26 (2 H, br s), 3.83 (3 H, s), 3.78 (2 H, s), 3.76 (3 H, s).

Step 5. 9-Chloro-7-(2-methoxybenzyl)-1-methyl-1H-pyrazolo[4,3-b]quinoline

The title compound was prepared according to the procedure of step 6 in EXAMPLE 13 using [2-amino-5-(2-methoxybenzyl)phenyl](4-iodo-1-methyl-1H-pyrazol-5-yl)methanone (EXAMPLE 21, step 4), instead of [2-amino-5-(4-chlorobenzyl)phenyl](4-iodo-1-methyl-1H-pyrazol-5-yl)methanone.
Rf value: 0.25 (ethyl acetate/hexane=1/1).
$^1$H-NMR (CDCl$_3$) δ: 8.37 (1 H, s), 8.18 (1 H, s), 8.06 (1 H, d, J=8.7 Hz), 7.59 (1 H, d, J=1.8 and 8.9 Hz), 7.26–7.21 (1 H, m), 7.16 (1 H, d, J=7.7 Hz), 6.94–6.88 (2 H, m), 4.50 (3 H, s), 4.23 (2 H, s), 3.85 (3 H, s).

Step 6. 7-(2-Methoxybenzyl)-1-methyl-1,4-dihydro-9H-pyrazolo[4,3-b]quinolin-9-one The title compound was prepared according to the procedure of step 7 in EXAMPLE 13 using 9-chloro-7-(2-methoxybenzyl)-1-methyl-1H-pyrazolo[4,3-b]quinoline (EXAMPLE 21, step 5), instead of 9-chloro-7-(4-chlorobenzyl)-1-methyl-1H-pyrazolo[4,3-b]quinoline.

m.p.: 255° C. (recrystallized from acetic acid and water)
IR (KBr) ν: 3142, 1637, 1591, 1541, 1490, 1394, 1363, 1240, 763 cm$^{-1}$.
$^1$H-NMR (CDCl$_3$) δ: 11.74 (1 H, br s), 8.02 (1 H, d, J=2.0 Hz), 7.78 (1 H, s), 7.53 (1 H, dd, J=2.0 and 8.6 Hz), 7.44 (1 H, d, J=8.4 Hz), 7.25–7.14 (2 H, m), 6.99 (1 H, d, J=7.5 Hz), 6.89 (1 H, t, J=1.1 Hz), 4.29 (3 H, s), 4.00 (2 H, s), 3.79 (3 H, s).
Anal. Calcd. for C$_{19}$H$_{17}$N$_3$O$_2$.0.1H$_2$O: C, 71.06; H, 5.40; N, 13.08. Found: C, 70.98; H, 5.25; N, 12.97.

Example 22

SODIUM 2-[[1-METHYL-1,4-DIHYDRO-9H-PYRAZOLO[4,3-b]QUINOLIN-9-ONE]-7-YL-METHYL] PHENOXIDE.

Step 1. 7-(2-Hydroxybenzyl)-1-methyl-1,4-dihydro-9H-pyrazolo[4,3-b]quinolin-9-one A mixture of 7-(2-methoxybenzyl)-1-methyl-1,4-dihydro-9H-pyrazolo[4,3-b]quinolin-9-one (EXAMPLE 21, step 6, 0.25 g, 0.78 mmol), 47% aqueous hydrobromic acid (15 ml) and acetic acid (15 ml) was heated at reflux temperature for 2 h. After cooling to room temperature, water (30 ml) was added. The formed pale yellow solid was collected by filtration, washed with water (50 ml) and diethyl ether (50 ml) to give 0.19 g (82%) of the title compound as a pale yellow solid.
Rf value: 0.35 (ethyl acetate/hexane=1/2).
$^1$H-NMR (CDCl$_3$) δ: 11.72 (1 H, br s), 9.41 (1 H, br s), 8.04 (1 H, d, J=1.7 Hz), 7.78 (1 H, s), 7.55 (1 H, dd, J=2.0 and 8.6 Hz), 7.44 (1 H, d, J=8.6 Hz), 7.10–7.00 (2 H, m), 6.81 (1 H, d, J=7.1 Hz), 6.75–6.70 (1 H, m), 4.29 (3 H, s), 3.97 (2 H, s).

Step 2. Sodium 2-[[1-Methyl-1,4-dihydro-9H-pyrazolo[4,3-b]quinolin-9-one]-7-yl-methyl]phenoxide To a solution of 7-(2-hydroxybenzyl)-1-methyl-1,4-dihydro-9H-pyrazolo[4,3-b]quinolin-9-one (EXAMPLE 22, step 1, 0.18 g, 0.39 mmol) in ethanol (15 ml) and tetrahydrofuran (5 ml), 2N aqueous sodium hydroxide (0.19 ml, 0.39 mmol) was added at room temperature. After stirring for 2 h, removal of solvent gave a pale yellow brown solid. The resultant solid was washed with in diethyl ether (5 ml) and ethanol (0.5 ml) to give 0.12 g (94%) of the title compound as a pale yellow solid.
m.p.: >250° C.
IR (KBr) ν: 3288, 1635, 1587, 1533, 1454, 1431, 1407, 1247, 817, 767 cm$^{-1}$.
$^1$H-NMR (DMSO-d$_6$) δ: 8.00 (1 H, s), 7.70 (1 H, s), 7.42–7.37 (2 H, m), 7.03 (1 H, d, J=7.4 Hz), 6.99 (1 H, d, J=7.6 Hz), 6.81 (1 H, d, J=8.1 Hz), 6.72–6.67 (1 H, m), 4.28 (3 H, s), 3.93 (2 H, s).
Anal. Calcd. for C$_{18}$H$_{14}$N$_3$O$_2$Na.3H$_2$O.0.5C$_2$H$_6$O(ethanol): C, 56.43; H, 5.73; N, 10.39.
Found: C, 56.71; H, 5.25; N, 10.05.

Example 23

1-METHYL-7-(3-NITROBENZYL)-1,4-DIHYDRO-9H-PYRAZOLO[4,3-b]QUINOLIN-9-ONE.

Step 1. 9-Chloro-1-methyl-7-(3-nitrobenzyl)-1H-pyrazolo[4,3-b]quinoline

The title compound was prepared according to the procedure of step 3 in EXAMPLE 19 using tributyl(3-nitrobenzyl)stannane (H. Azizian et al., *J. Organomet. Chem.*, 1981, 215, 49), instead of 3-methoxybenzyltributylstannane.
MS (EI) m/z: 352 (M$^+$).
$^1$H-NMR (CDCl$_3$) δ: 8.20–8.10 (4 H, m), 8.40 (1 H, s), 7.64–7.57 (1 H, m), 7.54–7.47 (2 H, m), 4.52 (3 H, s), 4.35 (2 H, s).

Step 2. 1-Methyl-7-(3-nitrobenzyl)-1,4-dihydro-9H-pyrazolo[4,3-b]quinolin-9-one (CJ-024149)

The title compound was prepared according to the procedure of step 7 in EXAMPLE 13 using 9-chloro-1-methyl-7-(3-nitrobenzyl)-1H-pyrazolo[4,3-b]quinoline (EXAMPLE 23, step 1), instead of 9-chloro-7-(4-chlorobenzyl)-1-methyl-1H-pyrazolo[4,3-b]quinoline.

MS (EI) m/z: 334 ($M^+$).

m.p.: 279–283° C.

IR (KBr) ν: 3248, 3200, 3148, 3099, 1638, 1595, 1543, 1524, 1491, 1433, 1398, 1350, 1321, 1250, 1209, 1099, 979, 831, 810, 735, 691, 669 $cm^{-1}$.

$^1$H-NMR (DMSO-$d_6$) δ: 11.79 (1 H, br s), 8.16–8.11 (2 H, m), 8.11–8.07 (1 H, m), 7.80 (1 H, s), 7.76 (1 H, d, J=7.4 Hz), 7.65–7.58 (2 H, m), 7.50 (1 H, d, J=8.6 Hz), 4.29 (3 H, s), 4.24 (2 H, s).

Anal. Calcd. for $C_{18}H_{14}N_4O_3$: C, 64.67; H, 4.22; N, 16.76. Found: C, 64.33; H, 4.16; N, 16.57.

Example 24

7-(3-AMINOBENZYL)-1-METHYL-1,4-DIHYDRO-9H-PYRAZOLO[4,3-b]QUINOLIN-9-ONE HYDROCHLORIDE.

A mixture of 1-methyl-7-(3-nitrobenzyl)-1,4-dihydro-9H-pyrazolo[4,3-b]quinolin-9-one (EXAMPLE 23, step 2, 76 mg, 0.23 mmol), iron powder (63 mg, 1.1 mmol), and ammonium chloride (12 mg, 0.023 mmol) in ethanol (15 ml) and water (5 ml) was refluxed for 2 h. After cooling to room temperature, the mixture was filtered through a pad of Celite and the filtrate was concentrated in vacuo. The residue was collected by filtration and washed with ethanol and diisopropyl ether to give 60 mg (88%) of 7-(3-aminobenzyl)-1-methyl-1,4-dihydro-9H-pyrazolo[4,3-b]quinolin-9-one. 24 mg of this solid was treated with methanolic hydrochloric acid and the mixture was evaporated. The residue was washed with diisopropyl ether to give 29 mg of the title compound as a white solid.

MS (EI) m/z: 304 ($M^+$).

m.p.: 287° C. (decomposition).

IR (KBr) ν: 2830, 2520, 2579, 1643, 1597, 1541, 1474, 1408, 1396, 1369, 1344, 1277, 1256, 1204, 1186, 1153, 1101, 1007, 934, 872, 816, 797, 748, 692, 656, 448 $cm^{-1}$.

$^1$H-NMR (DMSO-$d_6$) δ: 11.88 (1 H, s), 8.08 (1 H, s), 7.80 (1 H, s), 7.58–7.31 (4 H, m), 7.22–7.15 (2 H, m), 4.30 (3 H, s), 4.13 (2 H, s). One signal due to $NH_2$ was not observed.

Anal. Calcd. for $C_{18}H_{16}N_4$·HCl·0.5$H_2O$: C, 55.97; H, 4.96; N, 14.50. Found: C, 56.13; H, 4.99; N, 14.10.

Example 25

7-(2-AMINOBENZYL)-1-METHYL-1,4-DIHYDRO-9H-PYRAZOLO[4,3-b]QUINOLIN-9-ONE HYDROCHLORIDE.

Step 1. 2-{2-[(9-Chloro-1-methyl-1H-pyrazolo[4,3-b]quinolin-7-yl)methyl]phenyl}-1H-isoindole-1,3(2H)-dione The title compound was prepared according to the procedure of step 3 in EXAMPLE 19 using 2-{2-[(tributylstannyl)methyl]phenyl}-1H-isoindole-1,3(2H)-dione* instead of 3-methoxybenzyltributylstannane.

Rf value: 0.39 (methanol/dichloromethane=1/15).

$^1$H-NMR (DMSO-$d_6$) δ: 8.55 (1 H, s), 7.91 (1 H, d, J=9.2 Hz), 7.79–7.70 (5 H, m), 7.63–7.33 (5 H, m), 4.37 (3 H, s), 4.18 (2 H, s).

*2-{2-[(Tributylstannyl)methyl]phenyl}-1H-isoindole-1,3(2H)-dione

The title compound was prepared according to the procedure of step 1 in EXAMPLE 21 using 2-[2-(bromomethyl)phenyl]-1H-isoindole-1,3(2H)-dione (M. Yamada et al., *J. Med. Chem.*, 1996, 39, 596), instead of 2-methoxybenzyl bromide.

Rf value: 0.57 (ethyl acetate/hexane=1/3).

$^1$H-NMR (CDCl$_3$) δ: 7.98–7.92 (2 H, m), 7.82–7.76 (2 H, m), 7.20–7.08 (4 H, m), 2.17 (2 H, s), 1.45–1.25 (6 H, m), 1.25–1.05 (6 H, m), 0.85–0.65 (15 H, m).

Step 2. 2-{2-[(1-Methyl-9-oxo-4,9-dihydro-1H-pyrazolo[4,3-b]quinolin-7-yl)methyl]phenyl}-1H-isoindole-1,3(2H)-dione The title compound was prepared according to the procedure of step 7 in EXAMPLE 13 using 2-{2-[(9-chloro-1-methyl-1H-pyrazolo[4,3-b]quinolin-7-yl)methyl]phenyl}-1H-isoindole-1,3(2H)-dione (EXAMPLE 25, step 1), instead of 9-chloro-7-(4-chlorobenzyl)-1-methyl-1H-pyrazolo[4,3-b]quinoline.

MS (EI) m/z: 434 ($M^+$).

m.p.: >300° C.

IR (KBr) ν: 3321, 1713, 1638, 1601, 1549, 1489, 1393, 1315, 1121, 1084, 970, 891, 754, 719, 637, 532 $cm^{-1}$.

$^1$H-NMR (DMSO-$d_6$) δ: 11.61 (1 H, s), 7.82–7.72 (6 H, m), 7.50–7.33 (4 H, m), 7.30–7.18 (2 H, m), 4.25 (3 H, s), 3.97 (2 H, s).

Anal. Calcd. for $C_{26}H_{18}N_4O_3$·0.7$H_2O$: C, 69.85; H, 4.37; N, 12.53. Found: C, 69.85; H, 4.19; N, 12.34.

Step 3. 7-(2-Aminobenzyl)-1-methyl-1,4-dihydro-9H-pyrazolo[4,3-b]quinolin-9-one hydrochloride A mixture of 2-{2-[(1-methyl-9-oxo-4,9-dihydro-1H-pyrazolo[4,3-b]quinolin-7-yl)methyl]phenyl}-1H-isoindole-1,3(2H)-dione (EXAMPLE 25, step 2, 242 mg, 0.558 mmol) and hydrazine hydrate (0.14 ml, 2.8 mmol) in ethanol (10 ml) was refluxed for 18 h. After cooling to room temperature, the mixture was evaporated in vacuo. The obtained residue was chromatographed on a column of silica gel eluting with methanol/dichloromethane (1:20) to give 139 mg (82%) of 7-(2-aminobenzyl)-1-methyl-1,4-dihydro-9H-pyrazolo[4,3-b]quinolin-9-one. 80 mg of this compound was treated with methanolic hydrochloric acid and the mixture was evaporated to give a yellow solid. This was washed with diisopropyl ether to give 78 mg of the title compound as a yellow solid.

MS (EI) m/z: 304 ($M^+$).

m.p.: 273° C.

IR (KBr) ν: 2812, 2573, 1636, 1595, 1539, 1495, 1412, 1340, 1281, 1215, 1188, 1155, 1103, 1011, 978, 876, 822, 756 $cm^{-1}$.

$^1$H-NMR (DMSO-$d_6$) δ: 11.89 (1 H, br s), 8.07 (1 H, s), 7.81 (1 H, s), 7.54 (1 H, s), 7.38–7.15 (3 H, m), 7.06 (1 H, d, J=7.6 Hz), 4.30 (3 H, s), 4.16 (2 H, s). One signal due to $NH_2$ was not observed.

Example 26

4-[(1-METHYL-9-OXO-4,9-DIHYDRO-1H-PYRAZOLO[4,3-b]QUINOLIN-7-YL)METHYL]BENZONITRILE.

Step 1. 4-[(9-Chloro-1-methyl-1H-pyrazolo[4,3-b]quinolin-7-yl)methyl]benzonitrile The title compound was prepared according to the procedure of step 3 in EXAMPLE 19 using 4-[(tributylstannyl)methyl]benzonitrile* instead of 3-methoxybenzyltributylstannane.

Rf value: 0.58 (methanol/dichloromethane=1/9).

$^1$H-NMR (CDCl$_3$) δ: 8.40 (1 H, s), 8.17–8.10 (2 H, m), 7.62 (2 H, d, J=8.2 Hz), 7.48 (1 H, dd, J=0.9, 8.9 Hz), 7.37 (2 H, d, J=8.6 Hz), 4.52 (3 H, s), 4.30 (2 H, s).

*4-[(Tributylstannyl)methyl]benzonitrile

The title compound was prepared according to the procedure of step 1 in EXAMPLE 21 using 4-(bromomethyl)benzonitrile instead of 2-methoxybenzyl bromide.

Rf value: 0.31 (ethyl acetate/hexane=1/30).

$^1$H-NMR (CDCl$_3$) δ: 7.44 (2 H, d, J=8.1 Hz), 7.03 (2 H, d, J=8.1 Hz), 2.37 (2 H, s), 1.50–1.35 (6 H, m), 1.35–1.15 (6 H, m), 0.90–0.78 (15 H, m).

Step 2. 4-[(1-Methyl-9-oxo-4,9-dihydro-1H-pyrazolo[4,3-b]quinolin-7-yl)methyl]benzonitrile The title compound was prepared according to the procedure of step 7 in EXAMPLE 13 using 4-[(9-chloro-1-methyl-1H-pyrazolo[4,3-b]quinolin-7-yl)methyl]benzonitrile (EXAMPLE 26, step 1), instead of 9-chloro-7-(4-chlorobenzyl)-1-methyl-1H-pyrazolo[4,3-b]quinoline.
MS (EI) m/z: 314 (M$^+$).
m.p.: 291° C.
IR (KBr) v: 3261, 3242, 3148, 2222, 1638, 1591, 1541, 1491, 1431, 1398, 1325, 1248, 1205, 976, 860, 825, 785, 667 cm$^{-1}$.
$^1$H-NMR (DMSO-d$_6$) δ: 11.79 (1 H, br s), 8.09 (1 H, br s), 7.81–7.74 (3 H, m), 7.56 (1 H, dd, J=2.0 and 8.7 Hz), 7.47 (2 H, d, J=8.2 Hz), 4.29 (3 H, s), 4.17 (2 H, s).
Anal. Calcd. for C$_{19}$H$_{14}$N$_4$O.0.7H$_2$O: C, 69.80; H, 4.75; N, 17.14. Found: C, 69.78; H, 4.37; N, 16.88.

Example 27
7-[4-(AMINOMETHYL)BENZYL]-1-METHYL-1,4-DIHYDRO-9H-PYRAZOLO[4,3-b]QUINOLIN-9-ONE HYDROCHLORIDE.

A mixture of 4-[(1-methyl-9-oxo-4,9-dihydro-1H-pyrazolo[4,3-b]quinolin-7-yl)methyl]benzonitrile (EXAMPLE 26, step 2, 100 mg, 0.32 mmol) and Raney-nickel (ca. 500 mg) in 2M ammonia-methanol was stirred under hydrogen atmosphere (4 atm) for 6 h at room temperature. The mixture was filtered through a pad of Celite and the pad was washed with methanol. The filtrate was concentrated in vacuo. The residue (ca 120 mg, yellow solid) was treated with methanolic hydrochloride (10 ml) and the mixture was evaporated. The obtained solid was washed with diisopropyl ether and methanol to give 96 mg (85%) of the title compound as a yellow solid.
MS (EI) m/z: 318 (M$^+$).
m.p.: >300° C.
$^1$H-NMR (DMSO-d$_6$) δ: 11.87 (1 H, s), 8.24 (3 H, br s), 8.03 (1 H, d, J=2.1 Hz), 7.79 (1 H, s), 7.56 (1 H, dd, J=2.1 and 8.6 Hz), 7.49 (1 H, d, J=8.4 Hz), 7.41 (2 H, d, J=8.1 Hz), 7.32 (2 H, d, J=8.2 Hz), 4.29 (3 H, s), 4.08 (2 H, s), 4.00 (1 H, d, J=7.6 Hz), 3.96 (1 H, d, J=7.6 Hz).

Example 28
3-[(1-METHYL-9-OXO-4,9-DIHYDRO-1H-PYRAZOLO[4,3-b]QUINOLIN-7-YL)METHYL]BENZONITRILE.
Step 1. 3-[(9-Chloro-1-methyl-1H-pyrazolo[4,3-b]quinolin-7-yl)methyl]benzonitrile A mixture of 7-bromo-9-chloro-1-methyl-1H-pyrazolo[4,3-b]quinoline (EXAMPLE 19, step 2, 800 mg, 2.70 mmol), 3-[(tributylstannyl)methyl]benzonitrile ((H. Azizian et al., *J. Organomet. Chem.*, 1981, 215, 49), 1.21 g, 2.97 mmol), dichlorobis(triphenylphosphine)palladium (II) (189 mg, 0.27 mmol) in hexamethylphosphoramide (15 ml) was stirred at 70° C. for 14 h. After cooling to room temperature, water (150 ml) was added, and extracted with ethyl acetate (300 ml×3). The combined organic layer was washed with water (100 ml), dried over magnesium sulfate, and concentrated in vacuo. The residue was chromatographed on a column of silica gel eluting with ethyl acetate/hexane (1:1.5 to 1:1) to give 572 mg (64%) of the title compound as a yellow solid.
Rf value: 0.59 (methanol/dichloromethane=1/9).
$^1$H-NMR (CDCl$_3$) δ: 8.40 (1 H, s), 8.17–8.10 (2 H, m), 7.62 (2 H, d, J=8.2 Hz), 7.48 (1 H, dd, J=0.9 and 8.9 Hz), 7.37 (2 H, d, J=8.6 Hz), 4.52 (3 H, s), 4.30 (2 H, s).
Step 2. 3-[(1-Methyl-9-oxo-4,9-dihydro-1H-pyrazolo[4,3-b]quinolin-7-yl)methyl]benzonitrile (CJ-024354)

A suspension of 3-[(9-chloro-1-methyl-1H-pyrazolo[4,3-b]quinolin-7-yl)methyl]benzonitrile (EXAMPLE 28, step 1, 729 mg, 2.19 mmol) in acetic acid (8 ml) and water (8 ml) was refluxed for 5 h. After cooling to room temperature, water (20 ml) was added and the precipitate was collected by filtration. This yellow solid was washed with water, ethanol and hexane to give 594 mg (86%) of the title compound as a yellow solid.
MS (EI) m/z: 314 (M$^+$).
m.p.: 275° C.
IR (KBr) v: 3261, 3206, 3150, 2226, 1634, 1591, 1543, 1489, 1456, 1427, 1396, 1323, 1248, 1205, 1159, 1097, 980, 916, 810, 692 cm$^{-1}$.
$^1$H-NMR (DMSO-d$_6$) δ: 11.79 (1 H, s), 8.09 (1 H, s), 7.80–7.76 (2 H, m), 7.71–7.46 (5 H, m), 4.30 (3 H, s), 4.14 (2 H, s).
Anal. Calcd. for C$_{19}$H$_{14}$N$_4$O.0.3H$_2$O: C, 71.37; H, 4.60; N, 17.52. Found: C, 71.53; H, 4.52; N, 17.53.

Example 29
3-[(1-METHYL-9-OXO-4,9-DIHYDRO-1H-PYRAZOLO[4,3-b]QUINOLIN-7-YL)METHYL]BENZAMIDE.

A mixture of 3-[(1-methyl-9-oxo-4,9-dihydro-1H-pyrazolo[4,3-b]quinolin-7-yl)methyl]benzonitrile (EXAMPLE 28, step 2, 100 mg, 0.32 mmol) and powdered potassium hydroxide (89 mg, 1.59 mmol) in 2-methyl-2-propanol (5 ml) and dimethylsulfoxide (2 ml) was stirred at 65° C. for 4.5 h. After cooling to room temperature, the mixture was poured into saturated aqueous ammonium chloride (50 ml), and the precipitate was collected by filtration. This yellow powder was washed with water, methanol and dichloromethane to give 55 mg (52%) of the title compound as a yellow solid.
MS (EI) m/z: 332 (M$^+$).
m.p.: >300° C.
IR (KBr) v: 3387, 3194, 3146, 1672, 1638, 1597, 1549, 1433, 1398, 1371, 1321, 1213, 1150, 1132, 982, 831, 742 cm$^{-1}$.
$^1$H-NMR (DMSO-d$_6$) δ: 11.77 (1 H, br s), 8.08 (1 H, d, J=1.7 Hz), 7.98–7.92 (1 H, m), 7.80–7.76 (2 H, m), 7.70 (1 H, d, J=6.8 Hz), 7.56 (1 H, dd, J=1.8 and 8.7 Hz), 7.48 (1 H, d, J=8.6 Hz), 7.45–7.30 (3 H, m), 4.29 (3 H, s), 4.11 (2 H, s).
Anal. Calcd. for C$_{19}$H$_{16}$N$_4$O$_2$.0.4H$_2$O: C, 67.21; H, 4.99; N, 16.50. Found: C, 67.19; H, 4.86; N, 16.26.

Example 30
3-[(1-METHYL-9-OXO-4,9-DIHYDRO-1H-PYRAZOLO[4,3-b]QUINOLIN-7-YL)METHYL]BENZOIC ACID. A suspension of 3-[(1-methyl-9-oxo-4,9-dihydro-1H-pyrazolo[4,3-b]quinolin-7-yl)methyl]benzamide (EXAMPLE 29, 106 mg, 0.318 mmol) in 6N hydrochloric acid (15 ml) was refluxed for 20 h. After cooling to room temperature, the precipitate was collected by filtration, and washed with diisopropyl ether. The obtained solid was chromatographed on a column of silica gel eluting with methanol/dichloromethane/acetic acid (1:10:0 to 1:5:trace) to give 45 mg (43%) of the title compound as a white solid.
MS (EI) m/z: 333 (M$^+$).
m.p.: >300° C.
IR (KBr) v: 3261, 3207, 3101, 1634, 1593, 1541, 1435, 1412, 1321, 1209, 978, 826, 793, 760,700, 669 cm$^{-1}$.
$^1$H-NMR (DMSO-d$_6$) δ: 8.06 (1 H, s), 7.83–7.74 (3 H, m), 7.53–7.46 (2 H, m), 7.32 (2 H, m), 4.28 (3 H, s), 4.06 (2 H, s). Two signals due to NH and CO$_2$H were not observed.
Anal. Calcd. for C$_{19}$H$_{15}$N$_3$O$_3$.3.8H$_2$O: C, 56.80; H, 5.67; N, 10.46. Found: C, 57.07; H, 5.63; N, 10.07.

Example 31
7-[3-(AMINOMETHYL)BENZYL]-1-METHYL-1,4-DIHYDRO-9H-PYRAZOLO[4,3-b]QUINOLIN-9-ONE HYDROCHLORIDE.

A mixture of 3-[(1-methyl-9-oxo-4,9-dihydro-1H-pyrazolo[4,3-b]quinolin-7-yl)methyl]benzonitrile (EXAMPLE 28, step 2, 150 mg, 0.477 mmol) and Raney-nickel (ca. 500 mg) in 2M methanolic ammonia was stirred under hydrogen atmosphere (4 atm) for 4 h at room temperature. The mixture was filtered through a pad of Celite, which was washed with methanol. The filtrate was concentrated in vacuo. The solid (ca. 180 mg) was treated with methanolic hydrochloric acid (5 ml) and the mixture was evaporated. The residue was recrystallized from methanol/diisopropyl ether to give 154 mg (91%) of the title compound as a yellow solid.
MS (EI) m/z: 318 (M$^+$).
m.p.: >300° C. (recrystallized from methanol/diisopropyl ether).
IR (KBr) v: 2955, 2620, 1591, 1537, 1477, 1406, 1283, 1263, 1219, 1194, 1099, 1011, 974, 804, 743, 700, 650 cm$^{-1}$.
$^1$H-NMR (DMSO-d$_6$) δ: 12.07 (1 H, br s), 8.45 (3 H, br s), 8.08 (1 H, br s), 7.79 (1 H, s), 7.56 (1 H, dd, J=1.6 and 9.1 Hz), 7.53 (1 H, d, J=8.6 Hz), 7.42–7.25 (4 H, m), 4.29 (3 H, s), 4.07 (2 H, s), 3.99 (1 H, d, J=5.8 Hz), 3.95 (1 H, J=6.1 Hz).

Example 32
2-[(1-METHYL-9-OXO-4,9-DIHYDRO-1H-PYRAZOLO[4,3-b]QUINOLIN-7-YL)METHYL]BENZAMIDE.

Step 1. 2-[(9-Chloro-1-methyl-1H-pyrazolo[4,3-b]quinolin-7-yl)methyl]benzonitrile The title compound was prepared according to the procedure of step 3 in EXAMPLE 19 using 2-[(tributylstannyl)methyl]benzonitrile* instead of 3-methoxybenzyltributylstannane.
Rf value: 0.19 (ethyl acetate/hexane=1/2).
$^1$H-NMR (DMSO-d$_6$) δ: 8.60 (1 H, s), 8.22 (1 H, br s), 8.13 (1 H, d, J=8.9 Hz), 7.87 (1 H, d, J=7.4 Hz), 7.80–8.60 (3 H, m), 7.50–7.40 (1 H, m), 4.49 (2 H, s), 4.43 (3 H, s).
*2-[(Tributylstannyl)methyl]benzonitrile The title compound was prepared according to the procedure of step 1 in EXAMPLE 21 using 2-(bromomethyl)benzonitrile instead of 2-methoxybenzyl bromide.
Rf value: 0.70 (ethyl acetate/hexane=1/3).
$^1$H-NMR (CDCl$_3$) δ: 7.49 (1 H, d, J=7.6 Hz), 7.36 (1 H, t, J=7.9 Hz), 7.12–6.99 (2 H, m), 2.56 (2 H, s), 1.55–1.35 (6 H, m), 1.35–1.20 (6 H, m), 1.00–0.75 (m, 15H).

Step 2. 2-[(1-Methyl-9-oxo-4,9-dihydro-1H-pyrazolo[4,3-b]quinolin-7-yl)methyl]benzonitrile The title compound was prepared according to the procedure of step 7 in EXAMPLE 13 using 2-[(9-chloro-1-methyl-1H-pyrazolo[4,3-b]quinolin-7-yl)methyl]benzonitrile (EXAMPLE 32, step 1), instead of 9-chloro-7-(4-chlorobenzyl)-1-methyl-1H-pyrazolo[4,3-b]quinoline.
MS (EI) m/z: 314 (M$^+$).
m.p.: 272° C.
IR (KBr) v: 3260, 3196, 3003, 2953, 2222, 1638, 1593, 1541, 1487, 1431, 1400, 1321, 1204, 1130, 974, 922, 799, 760, 631 cm$^{-1}$.
$^1$H-NMR (DMSO-d$_6$) δ: 8.28 (1 H, br s), 8.08 (1 H, br s), 7.65 (1 H, d, J=7.7 Hz), 7.62 (1 H, s), 7.58–7.48 (2 H, m), 7.37–7.29 (2 H, m), 4.43 (3 H, s), 4.33 (2 H, s). One signal due to NH was not observed.
Anal. Calcd. for $C_{19}H_{14}N_4O.0.4H_2O$: C, 70.97; H, 4.64; N, 17.42. Found: C, 70.92; H, 4.28; N, 17.03.

Step 3. 2-[(1-Methyl-9-oxo-4,9-dihydro-1H-pyrazolo[4,3-b]quinolin-7-yl)methyl]benzamide The title compound was prepared according to the procedure of EXAMPLE 29 using 2-[(1-methyl-9-oxo-4,9-dihydro-1H-pyrazolo[4,3-b]quinolin-7-yl)methyl]benzonitrile (EXAMPLE 32, step 2), instead of 3-[(1-methyl-9-oxo-4,9-dihydro-1H-pyrazolo[4,3-b]quinolin-7-yl)methyl]benzonitrile.
MS (EI) m/z: 332 (M$^+$).
m.p.: >300° C.
IR (KBr) v: 3242, 3090, 1638, 1601, 1543, 1485, 1414, 1396, 1364, 1319, 1151, 1134, 1099, 974, 746, 664, 635 cm$^{-1}$.
$^1$H-NMR (DMSO-d$_6$) δ: 8.05 (1 H, br s), 7.78 (2 H, s), 7.54 (1 H, dd, J=2.0 and 8.7 Hz), 7.46–7.20 (6 H, m), 4.30–4.24 (5 H, m). One signal due to NH was not observed.
Anal. Calcd. for $C_{19}H_{16}N_4O_2.0.8H_2O$: C, 65.81; H, 5.12; N, 16.16. Found: C, 65.88; H, 4.97; N, 15.79.

Example 33
7-[2-(AMINOMETHYL)BENZYL]-1-METHYL-1,4-DIHYDRO-9H-PYRAZOLO[4,3-b]QUINOLIN-9-ONE HYDROCHLORIDE.

Step 1. 2-[2-(9-Chloro-1-methyl-1H-pyrazolo[4,3-b]quinoline-7-yl)benzyl]-1H-isoindole-1,3(2H)-dione The title compound was prepared according to the procedure of step 3 in EXAMPLE 19 using 2-[2-(tributylstannyl)benzyl]-1H-isoindole-1,3(2H)-dione* instead of 3-methoxybenzyltributylstannane.
Rf value: 0.10 (ethyl acetate/hexane=1/2).
$^1$H-NMR (DMSO-d$_6$) δ: 8.54 (1 H, s), 7.97 (1 H, d, J=9.0 Hz), 7.66 (1 H, s), 7.60–7.49 (3 H, m), 7.44–7.28 (6 H, m), 4.83 (2 H, s), 4.42 (2 H, s), 4.39 (3 H, s).
*2-[2-(tributylstannyl)benzyl]-1H-isoindole-1,3(2H)-dione The title compound was prepared according to the procedure of step 1 in EXAMPLE 21 using 2-(2-bromobenzyl)-1H-isoindole-1,3(2H)-dione (M. Shugo et al., JP 06199791 A2), instead of 2-methoxybenzylbromide.
Rf value: 0.85 (ethyl acetate/hexane=1/3).
$^1$H-NMR (CDCl$_3$) δ: 7.88–7.84 (2 H, m), 7.73–7.71 (2 H, m), 7.16 (1 H, d, J=7.5 Hz), 7.12–7.04 (1 H, m), 7.03–6.88 (2 H, m), 4.77 (2 H, s), 2.53 (2 H, s), 1.50–1.36 (6 H, m), 1.35–1.20 (6 H, m), 0.90–0.83 (15 H, m).

Step 2. 2-[2-[(1-Methyl-9-oxo-4,9-dihydro1H-pyrazolo[4,3-b]quinoline-7-yl)methyl]benzyl]-1H-isoindole-1,3(2H)-dione The title compound was prepared according to the procedure of step 7 in EXAMPLE 13 using 2-[2-(9-chloro-1-methyl-1H-pyrazolo[4,3-b]quinoline-7-yl)benzyl]-1H-isoindole-1,3(2H)-dione (EXAMPLE 33, step 1), instead of 9-chloro-7-(4-chlorobenzyl)-1-methyl-1H-pyrazolo[4,3-b]quinoline.
Rf value: 0.20 (ethyl acetate/hexane=1/2).
$^1$H-NMR (DMSO-d$_6$) δ: 11.72 (1 H, s), 7.84 (1 H, s), 7.76 (1 H, s), 7.77–7.65 (4 H, m), 7.45–7.35 (2 H, m), 7.35–7.21 (4 H, m), 4.75 (2 H, m), 4.27 (3 H, s), 4.25 (2 H, s).

Step 3. 7-[2-(Aminomethyl)benzyl]-1-methyl-1,4-dihydro-9H-pyrazolo[4,3-b]quinolin-9-one hydrochloride A mixture of 2-[2-[(1-methyl-9-oxo-4,9-dihydro-1H-pyrazolo[4,3-b]quinoline-7-yl)methyl]benzyl]-1H-isoindole-1,3(2H)-dione (EXAMPLE 33, step 2, 70 mg, 0.16 mmol) and hydrazine mono hydrate (0.012 ml, 0.24 mmol) in ethanol (1 ml) was refluxed for 24 h. After cooling to room temperature, the mixture was concentrated in vacuo. 85 mg of pale yellow solid obtained was chromatographed on a column of basic silica gel (30 g) eluting with methanol/dichloromethane (1:100) to afford 30 mg (60%) of the free base of the title compound as a yellow solid. The solid was dissolved in 10% methanolic hydrochloric acid (5 m) and removal of solvent gave pale a yellow solid. Recrystallization from ethanol and diethyl ether afforded 64 mg (96%) of the title compound as a pale yellow solid.

m.p.: >250° C. (recrystallized from ethanol and diethyl ether)

IR (KBr) v: 3429, 2958, 1635, 1616, 1595, 1541, 1521, 1508, 1489, 1409 cm$^{-1}$.

$^1$H-NMR (DMSO-d$_6$) δ: 11.87 (1 H, s), 8.00 (2 H, br s), 7.81 (1 H, s), 7.51 (1 H, s), 7.51–7.41 (3 H, m), 7.38–7.33 (2 H, m), 7.28–7.20 (1 H, m), 4.29 (3 H, s), 4.21 (2 H, s), 4.08–3.96 (2 H, m).

MS (EI): 318 (M$^+$)

Anal. Calcd. for C$_{19}$H$_{18}$N$_4$O.HCl.1.5H$_2$O: C, 59.76; H, 5.81; N, 14.67. Found: C, 59.53; H, 5.58; N, 14.43.

Example 34

7-[2-(2-AMINOETHYL)BENZYL]-1-METHYL-1,4-DIHYDRO-9H-PYRAZOLO[4,3-b]QUINOLIN-9-ONE HYDROCHLORIDE.

Step 1. {2-[(9-Chloro-1-methyl-1H-pyrazolo[4,3-b]quinolin-7-yl)methyl]phenyl}acetonitrile The title compound was prepared according to the procedure of step 3 in EXAMPLE 19 using {2-[(tributylstannyl)methyl]phenyl }acetonitrile* instead of 3-methoxybenzyltributylstannane.

Rf value: 0.45 (methanol/dichloromethane=1/9).

$^1$H-NMR (CDCl$_3$) δ: 8.40 (1 H, s), 8.13 (1 H, d, J=8.9 Hz), 8.08 (1 H, br s), 7.50–7.44 (2 H, m), 7.40–7.34 (2 H, m), 4.51 (3 H, s), 4.32 (2 H, s), 3.66 (2 H, s).

*{2-[(Tributylstannyl)methyl]phenyl}acetonitrile

The title compound was prepared according to the procedure of step 1 in EXAMPLE 21 using [2-(bromomethyl)phenyl]acetonitrile (G. Stefancich et al., *J. Heterocycl. Chem.*, 1979, 16, 1443), instead of 2-methoxybenzyl bromide.

Rf value: 0.70 (ethyl acetate/hexane=1/5).

$^1$H-NMR (CDCl$_3$) δ: 7.34–7.29 (1 H, m), 7.21–7.13 (1 H, m), 7.06–6.99 (2 H, m), 3.57 (2 H, s), 2.27 (2 H, s), 1.48–1.32 (6 H, m), 1.32–1.18 (6 H, m), 0.90–0.78 (15 H, m).

Step 2. {2-[(1-Methyl-9-oxo-4,9-dihydro-1H-pyrazolo[4,3-b]quinolin-7-yl)methyl]phenyl}acetonitrile (CJ-024330)

The title compound was prepared according to the procedure of step 7 in EXAMPLE 13 using {2-[(9-chloro-1-methyl-1H-pyrazolo[4,3-b]quinolin-7-yl)methyl]phenyl}acetonitrile (EXAMPLE 34, step 1), instead of 9-chloro-7-(4-chlorobenzyl)-1-methyl-1H-pyrazolo[4,3-b]quinoline.

MS (EI) m/z: 328 (M$^+$).

m.p.: 257° C.

IR (KBr) v: 3254, 3233, 3200, 3182, 3145, 3096, 2240, 1634, 1591, 1541, 1431, 1398, 1371, 1248, 1205, 1150, 974, 934, 829, 748, 669, 442 cm$^{-1}$.

$^1$H-NMR (DMSO-d$_6$) δ: 11.80 (1 H, s), 7.99 (1 H, s), 7.80 (1 H, s), 7.49 (2 H, s), 7.45–7.40 (1 H, m), 7.35–7.30 (2 H, m), 7.23–7.20 (1 H, m), 4.29 (3H, s), 4.15 (2 H, s), 3.98 (2 H, s).

Anal. Calcd. for C$_{20}$H$_{16}$N$_4$O.0.2H$_2$O: C, 72.36; H, 4.98; N, 16.88. Found: C, 72.16; H, 4.79; N, 16.93.

Step 3. 7-[2-(2-Aminoethyl)benzyl]-1-methyl-1,4-dihydro-9H-pyrazolo[4,3-b]quinolin-9-one hydrochloride The title compound was prepared according to the procedure of EXAMPLE 31 using {2-[(1-methyl-9-oxo-4,9-dihydro-1H-pyrazolo[4,3-b]quinolin-7-yl)methyl]phenyl}acetonitrile (EXAMPLE 34, step 2), instead of 3-[(1-methyl-9-oxo-4,9-dihydro-1H-pyrazolo[4,3-b]quinolin-7-yl)methyl]benzonitrile.

MS (EI) m/z: 302 ([M-CH$_2$NH$_2$]$^+$).

m.p.: >300° C.

IR (KBr) v: 3400, 2950, 2343, 1638, 1589, 1543, 1487, 1435, 1321, 1205, 1103, 978, 827, 752, 669, 637 cm$^{-1}$.

$^1$H-NMR (DMSO-d$_6$) δ: 12.02 (1 H, br s), 8.10 (2 H, br s), 7.95 (1 H, s), 7.79 (1 H, s), 7.54 (2 H, s), 7.28–7.20 (4 H, m), 4.28 (3 H, s), 4.15 (2 H, s), 2.92 (4 H, br s).

Example 35

1-METHYL-7-(3-PYRIDINYLMETHYL)-1,4-DIHYDRO-9H-PYRAZOLO[4,3-b]QUINOLIN-9-ONE HYDROCHLORIDE.

Step 1. 9-Chloro-1-methyl-7-(3-pyridinylmethyl)-1H-pyrazolo[4,3-b]quinoline

The title compound was prepared according to the procedure of step 3 in EXAMPLE 19 using 3-(tributylstannylmethyl)pyridine (B. Cimetiere et al., *Bioorg. Med. Chem. Lett.*, 1998, 8, 1381), instead of 3-methoxybenzyltributylstannane.

Rf value: 0.18 (ethyl acetate/hexane=1/2).

$^1$H-NMR (DMSO-d$_6$) δ: 8.62 (1 H, d, J=1.7 Hz), 8.59 (1 H, s), 8.44 (1 H, dd, J=1.7 and 4.7 Hz), 8.22 (1 H, s), 8.10 (1 H, d, J=8.8 Hz), 7.77–7.72 (1 H, m), 7.68 (1 H, dd, J=1.8 and 8.8 Hz), 7.37–7.32 (1 H, m), 4.43 (3 H, s), 4.30 (2 H, s), 3.32 (6 H, s).

Step 2. 1-Methyl-7-(3-pyridinylmethyl)-1,4-dihydro-9H-pyrazolo[4,3-b]quinolin-9-one hydrochloride.

A suspension of 9-chloro-1-methyl-7-(3-pyridinylmethyl)-1H-pyrazolo[4,3-b]quinoline (EXAMPLE 35, step 1, 0.17 g, 0.54 mmol) in 50% aqueous acetic acid (10 ml) was refluxed for 16 h. After cooling to room temperature, water (10 ml) was added. The pale yellow solid was collected by filtration, washed with water (30 ml) and dried in vacuo to afford 0.13 g (83%) of free base of the title compound as a pale yellow solid. The solid was dissolved in 10% methanolic hydrochloric acid (5 m) and concentrated. Recrystallization from isopropyl alcohol and diethyl ether afforded 68 mg (38%) of the title compound as a pale yellow solid.

m.p.: 259° C. (recrystallized from isopropyl alcohol and diethyl ether)

IR (KBr) v: 3078, 1641, 1608, 1554, 1487, 1431, 1184, 1107, 833 cm$^{-1}$.

$^1$H-NMR (DMSO-d$_6$) δ: 11.92 (1 H, s), 8.89 (1 H, s), 8.75 (1 H, d, J=5.3 Hz), 8.37 (1 H, d, J=8.1 Hz), 8.16 (1 H, s), 7.91 (1 H, dd, J=5.7 Hz), 7.81 (1 H, s), 7.62 (1 H, dd, J=2.0, 8.6 Hz), 7.52 (1 H, d, J=8.6 Hz), 4.30 (5 H, s).

Anal. Calcd. for C$_{17}$H$_{14}$N$_4$O.HCl.0.15H$_2$O: C, 61.97; H, 4.68; N, 17.00. Found: C, 61.73; H, 4.70; N, 16.92.

Example 36

7-[HYDROXY(PHENYL)METHYL]-1-METHYL-1,4-DIHYDRO-9H-PYRAZOLO[4,3-b]-QUINOLIN-9-ONE.

Step 1. 7-Benzoyl-1-methyl-1,4-dihydro-9H-pyrazolo[4,3-b]quinolin-9-one

To a suspension of 7-benzyl-1-methyl-1,4-dihydro-9H-pyrazolo[4,3-b]quinolin-9-one (EXAMPLE 11, step 3, 80 mg, 0.28 mmol) in acetic anhydride (3.0 ml), chromium(VI) oxide (69 mg, 0.69 mmol) was added at room temperature. After stirring for 16 h, the black mixture was poured into water (10 ml) and 2N aqueous hydrogen chloride (20 ml) was added. The mixture was extracted with ethyl acetate (50 ml×2), washed with saturated aqueous sodium bicarbonate (30 ml) and dried over magnesium sulfate. Removal of solvent gave 105 mg of yellow oil, which was chromatographed on a column of silica gel (20 g) eluting with methanol/dichloromethane (1:25) to afford 56 mg (67%) of the title compound as a pale yellow amorphous solid.

Rf value: 0.20 (ethyl acetate/hexane=1/2).
$^1$H-NMR (CDCl$_3$) δ: 9.04 (1 H, d, J-1.8 Hz), 8.14 (1 H, dd, J=1.8 and 8.7 Hz), 7.88–7.82 (2 H, m), 7.68–7.49 (3 H, m), 7.18 (1 H, s), 6.96 (1 H, d, J=8.7 Hz), 4.49 (1 H, s).

Step 2. (9-Chloro-1-methyl-1H-pyrazolo[4,3-b]quinolin-7-yl)(phenyl)methanone

A solution of 7-benzoyl-1-methyl-1,4-dihydro-9H-pyrazolo[4,3-b]quinolin-9-one (EXAMPLE 36, step 1, 33 mg, 0.11 mmol) in phosphorus oxychloride (3 ml) was refluxed for 3 h. After evaporation, the residue was dissolved in ethyl acetate (20 ml) and washed with saturated aqueous sodium bicarbonate (20 ml). The water layer was extracted with ethyl acetate (20 ml×2) and the combined organic layer was dried over sodium sulfate. Removal of solvent gave an oily residue, which was purified by preparative thin layer chromatography developing with ethyl acetate/hexane (2:1) to afford 24 mg (69%) of the title compound as a white solid.
MS (EI) m/z: 321 (M$^+$).
$^1$H-NMR (CDCl$_3$) δ: 8.83 (1 H, d, J=1.6 Hz), 8.47 (1 H, s), 8.30 (1 H, d, J=8.9 Hz), 8.14 (1 H, dd, J=1.6 and 8.9 Hz), 7.92 (2 H, d, 7.2 Hz), 7.68–7.54 (3 H, m), 4.54 (3 H, s).

Step 3. (9-Chloro-1-methyl-1H-pyrazolo[4,3-b]quinolin-7-yl)(phenyl)methanol

To a suspension of (9-chloro-1-methyl-1H-pyrazolo[4,3-b]quinolin-7-yl)(phenyl)methanone (EXAMPLE 36, step 2, 205 mg, 0.64 mmol) in ethanol (90 ml) was added sodium borohydride (24 mg, 0.64 mmol) at 0° C. After the mixture was stirred at room temperature for 14 h, water (90 ml) was added and extracted with ethyl acetate (100 ml×2). The organic extracts were dried over sodium sulfate and concentrated. Purification by column chromatography on silica gel eluting with ethyl acetate/hexane (1:1) gave 141 mg (68%) of the title compound as a white solid.
Rf value: 0.25 (ethyl acetate/hexane=1/1, developed twice).
$^1$H-NMR (CDCl$_3$) δ: 8.49 (1 H, br s), 8.39 (1 H, s), 8.12 (1 H, d, J=8.9 Hz), 7.62 (1 H, dd, J=1.9 and 8.9 Hz), 7.47–4.31 (5 H, m), 6.10 (1 H, d, J=2.7 Hz), 4.52 (3 H, s), 2.48 (1 H, d, J=3.5 Hz).

Step 4. 7-[Hydroxy(phenyl)methyl]-1-methyl-1,4-dihydro-9H-pyrazolo[4,3-b]-quinolin-9-one The title compound was prepared according to the procedure of step 7 in EXAMPLE 13 using (9-chloro-1-methyl-1H-pyrazolo[4,3-b]quinolin-7-yl)(phenyl)methanol (EXAMPLE 36, step 3), instead of 9-chloro-7-(4-chlorobenzyl)-1-methyl-1H-pyrazolo[4,3-b]quinoline.
Rf value: 0.10 (methanol/dichloromethane=1/9).
$^1$H-NMR (DMSO-d$_6$) δ: 11.75 (1 H, s), 8.24 (1 H, d, J=1.9 Hz), 7.78 (1 H, s), 7.63 (1 H, dd, J=1.9 and 8.5 Hz), 7.46 (1 H, d, J=8.5 Hz), 7.41–7.21 (5 H, m), 5.96 (1 H, d, J=4.1 Hz), 5.82 (1 H, d, J=4.3 Hz), 4.30 (3 H, s).

Example 37
1-METHYL-5-PHENYL-1,4-DIHYDRO-9H-PYRAZOLO[4,3-b]QUINOLIN-9-ONE.

1-Methyl-5-phenyl-1,4-dihydro-9H-pyrazolo[4,3-b]quinolin-9-one

A mixture of 5-bromo-1-methyl-1,4-dihydro-9H-pyrazolo[4,3-b]quinolin-9-one (EXAMPLE 5, 50 mg, 0.18 mmol), tributylphenyltin (0.12 ml, 0.36 mmol), tetrakis(triphenylphosphine)palladium (0) (62 mg, 0.054 mmol) and lithium chloride (19 mg, 0.45 mmol) in 1,4-dioxane (2 ml) was refluxed for 16 h. After cooling to room temperature, the mixture was evaporated, dissolved in ethyl acetate (20 ml) and the insoluble material was filtered off. The filtrate was concentrated in vacuo and purified by preparative thin layer chromatography developing with ethyl acetate/hexane (1/2). The obtained solid was recrystallized from diethyl ether to afford 17 mg (33%) of the title compound as a solid.

MS (EI) m/z: 274 (M$^+$).
$^1$H-NMR (DMSO-d$_6$) δ: 8.50 (1 H, d, J=8.3 Hz), 8.30 (1 H, br s), 7.58–7.47 (7 H, m), 7.31 (1 H, dd, J=7.2 and 8.3 Hz), 4.42 (3 H, s).

Example 38
8-(4-HYDROXYPHENYL)-1-METHYL-1,4-DIHYDRO-9H-PYRAZOLO[4,3-b]QUINOLIN-9-ONE.

Step 1. 8-Bromo-9-chloro-1-methyl-1H-pyrazolo[4,3-b]quinoline

The title compound was prepared according to the procedures of step 1 and 2 in EXAMPLE 3 using 3-bromoaniline, instead of 3-fluoroaniline.
Rf value: 0.50 (ethyl acetate/hexane=1/4).
$^1$H-NMR (CDCl$_3$) δ: 8.34 (1 H, s), 8.18 (1 H, d, J=8.6 Hz), 7.97 (1 H, d, J=8.1 Hz), 7.45 (1 H, t, J=8.2 Hz), 4.54 (3 H, s).

Step 2. 9-Chloro-8-(4-methoxyphenyl)-1-methyl-1H-pyrazolo[4.3-b]quinoline

A mixture of 8-bromo-9-chloro-1-methyl-1H-pyrazolo[4,3-b]quinoline (EXAMPLE 38, step 1, 100 mg, 0.337 mmol), 4-methoxyphenylboronic acid (56 mg, 0.371 mmol) and dichlorobis(triphenylphosphine)palladium (II) (24 mg, 0.034 mmol) in a mixture of saturated aqueous sodium bicarbonate (0.5 ml) and 1,2-dimethoxyethane (2.5 ml) was refluxed for 5 h. After cooling to room temperature, the mixture was diluted with diethyl ether (100 ml), washed with saturated aqueous sodium bicarbonate (30 ml) and dried over magnesium sulfate. Removal of solvent gave a solid, which was chromatographed on a column of silica gel eluting with ethyl acetate/hexane (1:5) to afford 65 mg (60%) of the title compound as a yellow solid.
Rf value: 0.45 (ethyl acetate/hexane=1/4).
$^1$H-NMR (CDCl$_3$) δ: 8.40 (1 H, s), 8.20 (1 H, dd, J=1.3 and 8.6 Hz), 7.67 (1 H, dd, J=7.0 and 8.8 Hz), 7.43 (1 H, dd, J=1.3 and 6.8 Hz), 7.27 (2 H, d, J=8.8 Hz), 6.97 (2 H, d, J=8.8 Hz), 4.41 (3 H, s), 3.90 (3 H, s).

Step 3. 8-(4-Methoxyphenyl)-1-methyl-1,4-dihydro-9H-pyrazolo[4.3-b]quinolin-9-one The title compound was prepared according to the procedure of step 3 in EXAMPLE 11 (CJ-023224) using 9-chloro-8-(4-methoxyphenyl)-1-methyl-1H-pyrazolo[4,3-b]quinoline (EXAMPLE 38, step 2), instead of 7-benzyl-9-chloro-1-methyl-1H-pyrazolo[4,3-b]quinoline.
MS (EI) m/z: 304 (M$^+$).
$^1$H-NMR (DMSO-d$_6$) δ: 11.76 (1 H, br s), 7.77 (1 H, s), 7.59 (1 H, dd, J=7.2 and 8.4 Hz), 7.50 (1 H, dd, J=1.3 and 8.4 Hz), 7.17 (2 H, d, J=8.6 Hz), 6.90 (2 H, d, J=8.8 Hz), 6.84 (1 H, dd, J=1.3 and 7.0 Hz), 4.16 (3 H, s), 3.81 (3 H, s).

Step 4. 8-(4-Hydroxyphenyl)-1-methyl-1,4-dihydro-9H-pyrazolo[4,3-b]quinolin-9-one A mixture of 8-(4-methoxyphenyl)-1-methyl-1,4-dihydro-9H-pyrazolo[4,3-b]quinolin-9-one (EXAMPLE 38, step 3, 41 mg, 0.14 mmol) in a mixture of 48% hydrobromic acid (1 ml) and acetic acid (1 ml) was refluxed for 7 h. After cooling to room temperature, water was added to the mixture. The formed solid was collected by filtration to give 37 mg (94%) of the title compound as a solid.
MS (EI) m/z: 290 (M$^+$).
m.p.: >300° C. (recrystallized from acetic acid/water).
IR (KBr) ν: 3312, 1612, 1587, 1545, 1516, 1447, 1258, 1240 cm$^{-1}$.
$^1$H-NMR (DMSO-d$_6$) δ: 11.72 (1 H, br s), 9.28 (1 H, br s), 7.76 (1 H, s), 7.57 (1 H, dd, J=7.0 and 8.4 Hz), 7.47 (1 H, dd, J=1.3 and 8.4 Hz), 7.04 (2 H, d, J=8.6 Hz), 6.82 (1 H, dd, J=1.3 and 7.0 Hz), 6.72 (2 H, d, J=8.4 Hz), 4.16 (3 H, s).
Anal. Calcd. for C$_{17}$H$_{13}$N$_3$O$_2$.0.6H$_2$O: C, 67.59; H, 4.74; N, 13.91. Found: C, 67.21; H, 4.57; N, 13.71.

Example 39
8-(3-HYDROXYPHENYL)-1-METHYL-1,4-DIHYDRO-9H-PYRAZOLO[4,3-b]QUINOLIN-9-ONE Step 1. 9-Chloro-8-(3-methoxyphenyl)-1-methyl-1H-pyrazolo[4,3-b]quinoline The title compound was prepared according to the procedure of step 2 in EXAMPLE 38 (CJ-024001) using 3-methoxyphenylboronic acid, instead of 4-methoxyphenylboronic acid.

Rf value: 0.45 (ethyl acetate/hexane=1/4).

$^1$H-NMR (CDCl$_3$) δ: 8.40 (1 H, s), 8.22 (1 H, dd, J=1.3 and 8.7 Hz), 7.67 (1 H, dd, J=6.9 and 8.7 Hz), 7.45 (1 H, dd, J=1.3 and 6.9 Hz), 7.33 (1 H, t, J=8.1 Hz), 6.99–6.92 (3 H, m), 4.41 (3 H, s), 3.85 (3 H, s).

Step 2. 8-(3-Methoxyphenyl)-1-methyl-1,4-dihydro-9H-pyrazolo[4,3-b]quinolin-9-one The title compound was prepared according to the procedure of step 3 in EXAMPLE 11 using 9-chloro-8-(3-methoxyphenyl)-1-methyl-1H-pyrazolo[4,3-b]quinoline (EXAMPLE 39, step 1), instead of 7-benzyl-9-chloro-1-methyl-1H-pyrazolo[4,3-b]quinoline.

MS (EI) m/z: 304 (M$^+$).

$^1$H-NMR (DMSO-d$_6$) δ: 11.79 (1 H, br s), 7.77 (1 H, s), 7.60 (1 H, dd, J=7.0 and 8.6 Hz), 7.53 (1 H, dd, J=1.5 and 8.4 Hz), 7.24 (1 H, t, J=8.1 Hz), 6.89–6.77 (4 H, m), 4.15 (3 H, s), 3.76 (3 H, s).

Step 3. 8-(3-Hydroxyphenyl)-1-methyl-1,4-dihydro-9H-pyrazolo[4,3-b]quinolin-9-one The title compound was prepared according to the procedure of step 4 in EXAMPLE 38 using 8-(3-methoxyphenyl)-1-methyl-1,4-dihydro-9H-pyrazolo[4,3-b]quinolin-9-one (EXAMPLE 39, step 2), instead of 8-(4-methoxyphenyl)-1-methyl-1,4-dihydro-9H-pyrazolo[4,3-b]quinolin-9-one.

MS (ESI) m/z: 292 (M$^+$+1), 290 (M$^+$−1)

m.p.: >300° C. (recrystallized from acetic acid/water).

IR (KBr) ν: 3265, 3159, 1622, 1595, 1553, 1429, 1161, 907, 781 cm$^{-1}$.

$^1$H-NMR (DMSO-d$_6$) δ: 11.77 (1 H, br s), 9.24 (1 H, s), 7.77 (1 H, s), 7.59 (1 H, dd, J=7.0 and 8.4 Hz), 7.51 (1 H, dd, J=1.5 and 4.3 Hz), 7.11 (1 H, t, J=7.7 Hz), 6.82 (1 H, dd, J=1.3 and 6.8 Hz), 6.69 (1 H, ddd, J=1.1, 2.4 and 8.1 Hz), 6.65–6.60 (2 H, m), 4.16 (3 H, s).

Anal. Calcd. for C$_{17}$H$_{13}$N$_3$O$_2$.2.2H$_2$O: C, 61.70; H, 5.30; N, 12.70. Found: C, 61.92; H, 4.90; N, 12.58.

Example 40
7-[3-HYDROXYPHENYL]-1-METHYL-1,4-DIHYDRO-9H-PYRAZOLO[4,3-b]QUINOLIN-9-ONE.

Step 1. 9-Chloro-7-(3-methoxyphenyl)-1-methyl-1H-pyrazolo[4,3-b]quinoline

A mixture of 7-bromo-9-chloro-1-methyl-1H-pyrazolo[4,3-b]quinoline (EXAMPLE 19, step 2, 100 mg, 0.34 mmol), 3-methoxyphenylboronic acid (56 mg, 0.37 mmol), dichlorobis(triphenylphosphine)palladium (II) (24 mg, 0.034 mmol), saturated aqueous sodium bicarbonate (2.0 ml) and 1,2-dimethoxyethane (8.0 ml) was refluxed for 30 min. After cooling to room temperature, the mixture was poured into water (50 ml), extracted with ethyl acetate (50 ml×2) and dried over magnesium sulfate. Removal of solvent gave 120 mg of blown oil, which was chromatographed on a column of silica gel (20 g) eluting with ethyl acetate/hexane (1:6) to afford 62 mg (57%) of the title compound as a pale yellow oil.

Rf value: 0.25 (ethyl acetate/hexane=1/6).

$^1$H-NMR (CDCl$_3$) δ: 8.53 (1 H, d, J=1.4 Hz), 8.42 (1 H, s), 8.26 (1 H, d, J=9.0 Hz), 7.99 (1 H, dd, J=2.0 and 9.0 Hz), 7.49–7.30 (3 H, m), 7.01–6.98 (1 H, m), 4.54 (3 H, s), 3.93 (3 H, s).

Step 2. 7-(3-Methoxyphenyl)-1-methyl-1,4-dihydro-9H-pyrazolo[4,3-b]quinolin-9-one The title compound was prepared according to the procedure of step 7 in EXAMPLE 13 using 9-chloro-7-(3-methoxyphenyl)-1-methyl-1H-pyrazolo[4,3-b]quinoline (EXAMPLE 40, step 1), instead of 9-chloro-7-(4-chlorobenzyl)-1-methyl-1H-pyrazolo[4,3-b]quinoline.

Rf value: 0.40 (ethyl acetate/hexane=1/2).

$^1$H-NMR (DMSO-d$_6$) δ: 11.92 (1 H, br s), 8.48 (1 H, s), 8.05–8.00 (1 H, m), 7.84 (1 H, s), 7.63 (1 H, d, J=8.4 Hz), 7.45–7.37 (1 H, m), 7.32×7.27 (1 H, m), 7.24 (1 H, s), 6.99–6.92 (1 H, m), 4.33 (3 H, s), 3.85 (3 H, s).

Step 3. 7-(3-Hydroxyphenyl)-1-methyl-1.4-dihydro-9H-pyrazolo[4,3-b]quinolin-9-one The title compound was prepared according to the procedure of step 4 in EXAMPLE 38 using 7-(3-methoxyphenyl)-1-methyl-1,4-dihydro-9H-pyrazolo[4,3-b]quinolin-9-one (EXAMPLE 40, step 2), instead of 8-(4-methoxyphenyl)-1-methyl-1,4-dihydro-9H-pyrazolo[4,3-b]quinolin-9-one.

m.p.: >250° C. (recrystallized from acetic acid and water)

IR (KBr) ν: 3197, 1593, 1542, 1473, 1404, 1303, 1201, 1161, 682 cm$^{-1}$.

$^1$H-NMR (DMSO-d$_6$) δ: 11.92 (1 H, br s), 9.57 (1 H, s), 8.43 (1 H, d, J=2.0 Hz), 7.95 (1 H, dd, J=2.4 and 8.8 Hz), 7.84 (1 H, s), 7.62 (1 H, d, J=8.8 Hz), 7.32–7.26 (1 H, m), 7.16–7.10 (2 H, m), 6.78–6.76 (1 H, m), 4.33 (3 H, s).

Anal. Calcd. for C$_{17}$H$_{13}$N$_3$O$_2$.2H$_2$O: C, 62.38; H, 5.23; N, 12.84. Found: C, 61.83; H, 4.62; N, 13.92.

Example 41
8-(4-AMINOPHENYL)-1-METHYL-1,4-DIHYDRO-9H-PYRAZOLO[4,3-b]QUINOLIN-9-ONE HYDROCHLORIDE.

Step 1. 9-Chloro-1-methyl-8-(4-nitrophenyl)-1H-pyrazolo[4,3-b]quinoline

The title compound was prepared according to the procedure of step 2 in EXAMPLE 38 using 4-nitrophenylboronic acid, instead of 4-methoxyphenylboronic acid.

Rf value: 0.30 (ethyl acetate/hexane=1/4).

$^1$H-NMR (CDCl$_3$) δ: 8.43 (1 H, s), 8.33–8.27 (3 H, m), 7.71 (1 H, dd, J=6.9 and 8.7 Hz), 7.57 (2 H, d, J=8.7 Hz), 7.43 (1 H, dd, J=1.3 and 6.9 Hz), 4.41 (3 H, s).

Step 2. 4-(9-chloro-1-methyl-1H-pyrazolo[4,3-b]quinolin-8-yl)aniline

A mixture of 9-chloro-1-methyl-8-(4-nitrophenyl)-1H-pyrazolo[4,3-b]quinoline (EXAMPLE 41, step 1, 45 mg, 0.13 mmol), iron powder (37 mg, 0.67 mmol) and ammonium chloride (0.7 mg, 0.013 mmol) in a mixture of ethanol (4 ml) and water (1.5 ml) was refluxed for 8 h. After cooling to room temperature, the mixture was filtered through a pad of Celite. The filtrate was concentrated, dissolved in ethyl acetate (300 ml), washed with water (100 ml) and dried over magnesium sulfate. Removal of solvent gave 41 mg (99%) of the title compound as a solid.

Rf value: 0.25 (ethyl acetate/hexane=1/4).

$^1$H-NMR (CDCl$_3$) δ: 8.39 (1 H, s), 8.17 (1 H, dd, J=1.3 and 8.8 Hz), 7.65 (1 H, dd, J=7.0 and 8.8 Hz), 7.43 (1 H, dd, J=1.5 and 7.0 Hz), 7.14 (2 H, d, J=8.6 Hz), 6.76 (2 H, d, J=8.4 Hz), 4.41 (3 H, s), 3.81 (2 H, br s).

Step 3. 8-(4-Aminophenyl)-1-methyl-1,4-dihydro-9H-pyrazolo[4,3-b]quinolin-9-one hydrochloric acid A mixture of 4-(9-chloro-1-methyl-1H-pyrazolo[4,3-b]quinolin-8-yl)aniline (EXAMPLE 41, step 2, 41 mg, 0.13 mmol) in 50% aqueous acetic acid (2 ml) was refluxed for 18 h. After cooling to room temperature, saturated sodium hydrogen carbonate (5 ml) was added to the mixture. The formed solid was collected by filtration, washed with water and dried. The obtained solid was dissolved in 10% methanolic hydrochloric acid (3 ml) and the mixture was stirred at room temperature for 18 h. The mixture was concentrated and recrystallized from ethanol to afford 19 mg (46%) of the title compound as a solid.

MS (ESI) m/z: 291 (M$^+$+1), 289 (M$^+$−1).

$^1$H-NMR (DMSO-d$_6$) δ: 11.93 (1 H, br s), 7.79 (1 H, s), 7.64 (1 H, dd, J=6.9 and 8.6 Hz), 7.57 (1 H, dd, J=1.3 and 8.4 Hz), 7.34 (2 H, d, J=8.4 Hz), 7.27 (2 H, d, J=8.6 Hz), 6.86 (1 H, dd, J=1.3 and 6.9 Hz), 4.14 (3 H, s).

Example 42

ETHYL (2E)-3-(1-METHYL-9-OXO-4,9-DIHYDRO-1H-PYRAZOLO[4,3-b]QUINOLIN-7-YL)-2-PROPENOATE.

Step 1. Ethyl (2E)-3-(9-chloro-1-methyl-1H-pyrazolo[4,3-b]quinolin-7-yl)-2-propenoate A mixture of 9-chloro-7-bromo-1-methyl-1H-pyrazolo[4,3-b]quinoline (EXAMPLE 19, step 2, 1 g, 3.4 mmol), ethyl acrylate (0.42 ml, 3.9 mmol), triethylamine (0.53 ml, 3.8 mmol), palladium acetate (76 mg, 0.34 mmol) and tri-o-tolylphosphine (0.62 g, 2.0 mmol) in N,N-dimethylformamide (80 ml) was stirred at 120° C. for 7 h. The mixture was cooled to room temperature and filtered through a pad of Celite. The filtrate was concentrated, diluted with ethyl acetate (50 ml) and washed with saturated aqueous sodium bicarbonate (50 ml). The water layer was extracted with ethyl acetate (50 ml×2) and the organic layers were combined. After dryness over sodium sulfate and evaporation, the residue was purified by column chromatography on silica gel eluting with ethyl acetate/hexane (1:3) to afford 0.79 g (74%) of the title compound as a pale yellow solid.

Rf value: 0.20 (ethyl acetate/hexane=1/3).

$^1$H-NMR (CDCl$_3$) δ: 8.44 (1 H, d, J=1.6 Hz), 8.41 (1 H, s), 8.18 (1 H, d, J=9.2 Hz), 7.93 (1 H, d, J=15.9 Hz), 7.90 (1 H, dd, J=1.6 and 9.2 Hz), 6.63 (1 H, d, J=15.9 Hz), 4.53 (3 H, s), 4.32 (2 H, q, J=7.1 Hz), 1.38 (3 H, t, J=7.1 Hz).

Step 2. Ethyl (2E)-3-(1-methyl-9-oxo-4,9-dihydro-1H-pyrazolo[4,3-b]quinolin-7-yl)-2-propenoate (CJ-024,080)

The title compound was prepared according to the procedure of step 3 in EXAMPLE 11 using ethyl (2E)-3-(9-chloro-1-methyl)-1H-pyrazolo[4,3-b]quinolin-7-yl)-2-propenoate (EXAMPLE 42, step 1), instead of 7-benzyl-9-chloro-1-methyl-1H-pyrazolo[4,3-b]quinoline.

MS (EI) m/z: 297 (M$^+$).

$^1$H-NMR (DMSO-d$_6$) δ: 12.07 (1 H, s), 8.41 (1 H, s), 8.08 (1 H, d, J=9.2 Hz), 7.85 (1 H, s), 7.77 (1 H, d, J=15.8 Hz), 7.54 (1 H, d, J=8.4 Hz), 6.60 (1 H, d, J=15.8 Hz), 4.32 (3 H, s), 4.19 (2 H, q, J=7.0 Hz), 1.27 (3 H, t, J=7.0 Hz).

Example 43

3-(1-METHYL-9-OXO-4,9-DIHYDRO-1H-PYRAZOLO[4,3-b]QUINOLIN-7-YL)PROPANENITRILE.

Step 1. (2E)-3-(9-Chloro-1-methyl-1H-pyrazolo [4,3-b]quinolin-7-yl)-2-propenitrile The title compound was prepared according to the procedure of step 1 in EXAMPLE 42 using acrylonitrile instead of ethyl acrylate.

MS (EI) n/z: 268 (M$^+$).

$^1$H-NMR (CDCl$_3$) δ: 8.43 (1 H, s), 8.39 (1 H, d, J=1.9 Hz), 8.21 (1 H, d, J=9.2 Hz), 7.81 (1 H, dd, J=19 and 9.2 Hz), 7.66 (1 H, d, J=16.6 Hz), 6.09 (1 H, d, J=16.6 Hz), 4.54 (3 H, s).

Step 2. (2E)-3-(1-Methyl-9-oxo-4,9-dihydro-1H-pyrazolo[4,3-b]quinolin-7-yl)-2-propenitrile The title compound was prepared according to the procedure of step 3 in EXAMPLE 11 using (2E)-3-(9-chloro-1-methyl-1H-pyrazolo[4,3-b]quinolin-7-yl)-2-propenitrile (EXAMPLE 43, step 1), instead of 7-benzyl-9-chloro-1-methyl-1H-pyrazolo[4,3-b]quinoline.

MS (EI) m/z: 250 (M$^+$).

$^1$H-NMR (DMSO-d$_6$) δ: 12.13 (1 H, s), 8.43 (1 H, d, J=1.8 Hz), 8.00 (1 H, dd, J=1.8 and 9.0 Hz), 7.86 (1 H, s), 7.81 (1 H, d, J=16.8 Hz), 7.55 (1 H, d, J=9.0 Hz), 6.43 (1 H, d, J=16.8 Hz), 4.31 (3 H, s).

Step 3. 3-(1-Methyl-9-oxo-4,9-dihydro-1H-pyrazolo[4,3-b]quinolin-7-yl)-2-propanenitrile (CJ-024,138)

To a suspension of (2E)-3-(1-methyl-9-oxo-4,9-dihydro-1H-parazolo[4,3-b]quinolin-7-yl)-2-propenitrile (EXAMPLE 43, step 2, 79 mg, 0.32 mmol) in a mixture of ethanol (150 ml) and tetrahydrofuran (5 ml) was added 40 mg of 10% palladium on carbon.

The mixture was stirred at room temperature under hydrogen atmosphere (1 atm) for 3.5 h. The mixture was filtered through a pad of Celite. And the filtrate was evaporated to give 55 mg (69%) of the title compound as a yellow solid.

MS (EI) m/z: 252 (M$^+$).

$^1$H-NMR (DMSO-d$_6$) δ: 8.14 (1 H, d, J=2.1 Hz), 7.80 (1 H, s), 7.60 (1 H, dd, J=2.1 and 8.7 Hz), 7.50 (1 H, d, J=8.7 Hz), 4.31 (3 H, s), 3.00 (2 H, t, J=7.2 Hz), 2.86 (2 H, t, J=7.1 Hz). One signal due to NH was not observed.

Example 44

7-(3-AMINOPROPYL)-1-METHYL-1,4-DIHYDRO-9H-PYRAZOLO[4,3-b]-QUINOLIN-9-ONE HYDROCHLORIDE.

A mixture of 3-(1-methyl-9-oxo-4,9-dihydro-1H-pyrazolo[4,3-b]quinolin-7-yl)-2-propanenitrile (EXAMPLE 43, step 3, 30 mg, 0.12 mmol), and Raney-nickel in 2M ammonia-ethanol (11 ml) was stirred at room temperature under hydrogen atmosphere (1 atm) for 24 h. The mixture was filtered through a pad of Celite and the filtrate was evaporated. The residue was chromatographed on a column of silica gel eluting with methanol/dichloromethane (1:100 to 1:20). The obtained 7-(3-aminopropyl)-1-methyl-1,4-dihydro-9H-pyrazolo[4,3-b]-quinolin-9-one was treated with methanolic hydrochloric acid and the formed solid was washed with diethyl ether. 23 mg (65%) of the title compound was obtained as a solid.

MS (EI) m/z: 256 (M$^+$).

m.p.: >300° C. (recrystallized from diethyl ether).

$^1$H-NMR (DMSO-d$_6$) δ: 11.84 (1 H, s), 8.09 (1 H, s), 7.81 (1 H, s), 7.54–7.49 (2 H, m), 4.31 (3 H, s), 2.83–2.74 (4 H, m), 1.92–1.87 (2 H, m).

Anal. Calcd. for C$_{14}$H$_{16}$N$_4$O.1.1HCl.H$_2$O: C, 53.48; H, 6.12; N, 17.82. Found: C, 53.12; H, 5.75; N, 17.57.

Example 45

7-ANILINO-1-METHYL-1,4-DIHYDRO-9H-PYRAZOLO[4,3-b]-QUINOLIN-9-ONE

Step 1. 9-Chloro-1-methyl-7-nitro-1H-pyrazolo[4,3-b]quinoline

A mixture of 1-methyl-7-nitro-1,4-dihydro-9H-pyrazolo [4,3-b]-quinolin-9-one ((Stepanov et. al., *Chem. Heterocycl. Compd.* (*Engl. Transl.*), 1985, 21, 905), 0.13 g, 0.53 mmol) and phosphorus oxychloride (3 ml) was refluxed for 3 h. After evaporation, the obtained residue was dissolved in ethyl acetate (100 ml), washed with saturated sodium bicarbonate (50 ml) and dried over sodium sulfate. Removal of solvent gave a residue which was chromatographed on a column of silica gel eluting with ethyl acetate/dichloromethane/hexane (1:4:4) to give 104 mg (78%) of the title compound as a solid.

MS (EI) m/z: 262 (M$^+$).

$^1$H-NMR (DMSO-d$_6$) δ: 9.20 (1 H, d, J=2.3 Hz), 8.76 (1 H, s), 8.45 (1 H, dd, J=2.3 and 9.5 Hz), 8.36 (1 H, d, J=9.5 Hz), 4.48 (3 H, s).

Step 2. 9-Chloro-1-methyl-1H-pyrazolo[4,3-b]quinolin-7-amine

The title compound was prepared according to the procedure of step 2 in the EXAMPLE 41 using 9-chloro-1-methyl-7-nitro-1H-pyrazolo[4,3-b]quinoline (EXAMPLE 45, step 1), instead of 9-chloro-1-methyl-8-(4-nitrophenyl)-1H-pyrazolo[4,3-b]quinoline.
MS (EI) m/z: 256 (M$^+$).
$^1$H-NMR (DMSO-d$_6$) δ: 8.38 (1 H, s), 7.84 (1 H, d, J=9.3 Hz), 7.25 (1 H, dd, J=2.1 and 9.3 Hz), 7.80(1 H, d, J=2.1 Hz), 6.14 (2 H, br s), 4.35 (3 H, s).

Step 3. 9-Chloro-1-methyl-N-phenyl-1H-pyrazolo[4,3-b]quinolin-7-amine

A mixture of 9-chloro-1-methyl-1H-pyrazolo[4,3-b]quinolin-7-amine (EXAMPLE 45, step 2, 0.16 g, 0.7 mmol), phenylboronic acid (0.17 g, 1.4 mmol), triethylamine (0.39 ml, 2.8 mmol) and copper acetate (0.25 g, 1.4 mmol) in dichloromethane (50 ml) was stirred at room temperature for 3.5 h and at refluxing temperature for 22 h. After filtration through a pad of Celite, the filtrate was diluted with dichloromethane (50 ml), washed with saturated aqueous sodium bicarbonate (50 ml) and dried over sodium sulfate. Removal of solvent gave a residue, which was chromatographed on a column of silica gel eluting with ethyl acetate/hexane (1:1) to give 23 mg (10%) of the title compound as a solid.
MS (EI) m/z: 308 (M$^+$).
$^1$H-NMR (CDCl$_3$) δ: 8.32 (1 H, s), 8.06 (1 H, d, J=9.5 Hz), 7.80 (1 H, d, J=2.2 Hz), 7.44 (1 H, dd, J=2.2 and 9.5 Hz), 7.40 (2 H, t, J=7.7 Hz), 7.32–7.30 (2 H, m) 7.10 (1 H, t, J=7.3 Hz), 6.18 (1 H, br s), 4.46 (3 H, s).

Step 4. 7-Anilino-1-methyl-1,4-dihydro-9H-pyrazolo[4,3-b]-quinolin-9-one

The title compound was prepared according to the procedure of step 3 in EXAMPLE 11 (CJ-023,224) using 9-chloro-1-methyl-N-phenyl-1H-pyrazolo[4,3-b]quinolin-7-amine (EXAMPLE 45, step 3), instead of 7-benzyl-9-chloro-1-methyl-1H-pyrazolo[4,3-b]quinoline.
MS (EI) m/z: 290 (M$^+$).
$^1$H-NMR (DMSO-d$_6$) δ: 11.68 (1 H, s), 8.24 (1 H, s), 7.94 (1 H, br s), 7.77 (1 H, s), 7.49 (2 H, br s), 7.24 (2 H, t, J=7.0 Hz), 7.08 (2 H, d, J=7.8 Hz), 6.82 (1 H, t, J=6.8 Hz), 4.30 (3 H, s).

Example 46
N-(1-METHYL-9-OXO-4,9-DIHYDRO-1H-PYRAZOLO[4,3-b]QUINOLIN-7-YL)BENZAMIDE.

Step 1. N-(9-Chloro-1-methyl-1H-pyrazolo[4,3-b]quinolin-7-yl)benzamide

A mixture of 9-chloro-1-methyl-1H-pyrazolo[4,3-b]quinolin-7-amine (EXAMPLE 45, step 2, 0.1 g, 0.43 mmol) and benzoyl chloride (0.06 ml, 0.52 mmol) in pyridine (8 ml) was stirred at room temperature for 4 h. After concentration, the residue was dissolved in dichloromethane (50 ml), washed with 2M hydrochloric acid (30 ml) and dried over sodium sulfate. Removal of solvent gave a residue, which was chromatographed on a column of silica gel eluting with ethyl acetate/hexane (2:1) to afford 41 mg (28%) of the title compound as a white solid.
MS (EI) m/z: 336 (M$^+$).
$^1$H-NMR (CDCl$_3$) δ: 8.91 (1 H, d, J=2.3 Hz), 8.40 (1 H, s), 8.21 (1 H, d, 9.3 Hz), 8.16 (1 H, br s), 7.99–7.96 (2 H, m), 7.84 (1 H, dd, J=2.3 and 9.3 Hz), 7.62–7.48 (3 H, m), 4.52 (3 H, s).

Step 2. N-(1-Methyl-9-oxo-4,9-dihydro-1H-pyrazolo[4.3-b]quinolin-7-yl)benzamide

The title compound was prepared according to the procedure of step 3 in EXAMPLE 11 (CJ-023,224) using N-(9-chloro-1-methyl-1H-pyrazolo[4,3-b]quinolin-7-yl)benzamide (EXAMPLE 46, step 1), instead of 7-benzyl-9-chloro-1-methyl-1H-pyrazolo[4,3-b]quinoline.
MS (EI) m/z: 318 (M$^+$).
m.p.: >300° C.
$^1$H-NMR (DMSO-d$_6$) δ: 11.83 (1 H, s), 10.45 (1 H, s), 8.67 (1 H, d, J=2.4 Hz), 8.12 (1 H, dd, J=2.4 and 9.3 Hz), 8.02–8.00 (2 H, m), 7.81 (1 H, s), 7.61–7.50 (4 H, m), 4.32 (3 H, s).
Anal. Calcd. for C$_{18}$H$_{14}$N$_4$O$_2$.1.4H$_2$O: C, 62.93; H, 4.93; N, 16.31. Found: C, 62.80; H, 4.39; N, 15.81.

Example 47
4-ETHYL-1,7DIMETHYL-1,4-DIHYDRO-9H-PYRAZOLO[4,3-b]QUINOLIN-9-ONE.

Step 1. 1-Methyl-4-[(4-methylphenyl)amino]-1H-pyrazole-5-carboxylic acid

A mixture of 4-iodo-1-methyl-1H-pyrazole-5-carboxylic acid ((Y. A. Manaev et al., *J. Gen. Chem. USSR.* (*Engl. Transl.*), 1982, 52, 2291), 2.92 g, 11.6 mmol), p-toluidine (6.20 g, 57.9 mmol), and copper powder (1.17 g, 18.4 mmol) in 5% aqueous sodium carbonate (60 ml) was stirring at 100° C. for 5 h. After cooling to room temperature, diethyl ether (100 ml) and 2N aqueous sodium hydroxide (100 ml) were added. This mixture was filtered through a pad of Celite, which was washed with 2N sodium hydroxide (200 ml) and ether (100 ml). The separated aqueous layer was washed with ether (100 ml), filtered through a pad of Celite again, and acidified with concentrated hydrochloric acid. The precipitate was collected by filtration, and washed with water to give 1.77 g (76.6 mmol, 66%) of the title compound as a gray powder.
MS (EI) m/z: 231 (M$^+$).
$^1$H-NMR (DMSO-d$_6$) δ: 7.61 (1 H, s), 7.05 (2 H, d, J=8.6 Hz), 6.98 (2 H, d, J=8.9 Hz), 4.00 (3 H, s), 2.22 (3 H, s). Two signals due to NH and CO$_2$H were not observed.

Step 2. 1,7-Dimethyl-1,4-dihydro-9H-pyrazolo[4,3-b]quinolin-9-one (UK-264,650)

A solution of 1-methyl-4-[(4-methylphenyl)amino]-1H-pyrazole-5-carboxylic acid (EXAMPLE 47, step 1, 1.00 g, 4.32 mmol) in phosphorus oxychloride (30 ml) was refluxed for 45 min. After cooling to room temperature, excess phosphorus oxychloride was removed in vacuo. To the brown residue, water (15 ml) and acetic acid (15 ml) were added and refluxed for 22 h. After cooling to room temperature, the solvent was removed in vacuo. The brown residue was washed with methanol to give 448 mg (2.10 mmol, 49%) of the title compound as a pale gray solid.
MS (EI) m/z: 213 (M$^+$).
m.p.: >300° C.
IR (KBr) ν: 3242, 3192, 3144, 3096, 2361, 2343, 1638, 1595, 1541, 1491, 1396, 1250, 1211, 1132, 957, 804, 669 cm$^{-1}$.
$^1$H-NMR (DMSO-d$_6$) δ:11.72 (1 H, br s), 8.03 (1 H, br s), 7.79 (1 H, s), 7.51 (1 H, dd, J=2.0 and 8.4 Hz), 7.45 (1 H, d, J=8.7 Hz), 4.30 (3 H, s), 2.41 (3 H, s).
Anal. Calcd. for C$_{12}$H$_{11}$N$_3$O: C, 67.59; H, 5.20; N, 19.71. Found: C, 67.28; H, 5.28; N, 19.75.

Step 3. 4-Ethyl-1,7-dimethyl-1,4-dihydro-9H-pyrazolo[4,3-b]quinolin-9-one (CJ-022841).

A mixture of 1,7-dimethyl-1,4-dihydro-9H-pyrazolo[4,3-b]quinolin-9-one (EXAMPLE 47, step 2, 21 mg, 0.01 mmol), iodoethane (0.02 ml, 0.25 mmol), and potassium carbonate (41 mg, 0.29 mmol) in N,N-dimethylformamide (2 ml) was stirred at 100° C. for 2 h. After cooling to room temperature, the solvent was removed in vacuo. The residue was dissolved in ethyl acetate (20 ml) and washed with water (20 ml). Removal of solvent gave a yellow solid, which was washed with hexane to afford 11 mg (47%) of the title compound as a yellow solid.

MS (EI) m/z: 241 (M+).
IR (KBr) v: 2980, 1638, 1599, 1528, 1477, 1437, 1379, 1308, 1290, 1182, 1086, 1040, 962, 874, 754 cm$^{-1}$.
$^1$H-NMR (DMSO-d$_6$) δ: 8.15 (1 H, br s), 8.09 (1 H, s), 7.70 (1 H, d, J=8.9 Hz), 7.61 (1 H, dd, J=2.4 and 8.9 Hz), 4.44 (2 H, q, J=7.0 Hz), 4.32 (3 H, s), 2.44 (3 H, s), 1.31 (3 H, t, J=7.0 Hz).

Example 48

4-BUTYL-1,7-DIMETHYL-1,4-DIHYDRO-9H-PYRAZOLO[4,3-b]QUINOLIN-9-ONE.

To a suspension of sodium hydride (60–72% in mineral oil, 38 mg, 0.94 mmol) in tetrahydrofuran (2 ml) was added a suspension of 1,7-dimethyl-1,4-dihydro-9H-pyrazolo[4,3-b]quinolin-9-one (EXAMPLE 47, step 2, 100 mg, 0.469 mmol) in tetrahydrofuran (5 ml) at 0° C. After 30 min, 1-iodobutane (0.11 ml, 0.94 mmol) was added. The mixture was stirred at room temperature for 3 h and at 70° C. for 4 h. After cooling to room temperature, water (30 ml) was added and extracted with ethyl acetate (50 ml×2). The combined organic layer was dried over magnesium sulfate, and concentrated in vacuo. The obtained solid was washed with hexane to give 67 mg (53%) of the title compound as a yellow solid.
MS (EI) m/z: 269 (M+).
m.p.: 262° C.
IR (KBr) v: 2957, 2932, 2864, 1636, 1603, 1533, 1477, 1441, 1377, 1325, 1300, 1204, 1184, 959, 806, 789 cm$^{-1}$.
$^1$H-NMR (CDCl$_3$) δ: 8.37 (1H, br s), 7.65 (1 H, s), 7.53 (1 H, dd, J=2.4 and 8.2 Hz), 7.38 (1 H, d, J=8.8 Hz), 4.46 (3 H, s), 4.25 (2 H, t, J=7.7 Hz), 2.49 (3 H, s), 1.92–1.80 (2 H, m), 1.52–1.40 (2 H, m), 1.00 (3 H, t, J=7.1 Hz).

Example 49

4-HEXYL-1,7-DIMETHYL-1,4-DIHYDRO-9H-PYRAZOLO[4,3-b]QUINOLIN-9-ONE.

The title compound was prepared according to the procedure of EXAMPLE 48 using 1-iodohexane instead of 1-iodobutane.
MS (EI) m/z: 297 (M+).
m.p.: 80–82° C.
$^1$H-NMR (CDCl$_3$) δ: 8.20 (1 H, br s), 8.15 (1 H, s), 7.75 (1 H, d, J=8.8 Hz), 7.75 (1 H, dd, J=2.4 and 8.8 Hz), 4.43 (2 H, t, J=7.7 Hz), 4.37 (3 H, s), 2.49 (3 H, s), 1.78 (2 H, quintet, J=7.5 Hz), 1.48–1.25 (6 H, m), 0.88 (3 H, t, J=7.1 Hz).

Example 50

4-(5-IODOPHENYL)-1,7-DIMETHYL-1,4-DIHYDRO-9H-PYRAZOLO[4,3-b]QUINOLIN-9-ONE.

To a suspension of sodium hydride (60–72% in mineral oil, 0.14 g, 3.5 mmol), which was washed with hexane and dried in vacuo, in N,N-dimethylformamide (25 ml) was added a N,N-dimethylformamide solution of 1,7-dimethyl-1,4-dihydro-9H-pyrazolo[4,3-b]quinolin-9-one (EXAMPLE 47, step 2, 0.5 g, 2.3 mmol) at 0° C. The mixture was allowed to warm up to room temperature and stirred for 1 h. After 1,5-diiodopentane (1.74 ml, 11.7 mmol) was added at 0° C., the mixture was stood at room temperature for 2 days. Additional sodium hydride (60–72% in mineral oil, 92 mg, 2.3 mmol) was added at room temperature. The mixture was stirred for 6 h, quenched with water and extracted with ethyl acetate (50 ml×2). The organic layer was dried over magnesium sulfate and concentrated. Purification by column chromatography on silica gel eluting with ethyl acetate/hexane (1:1) gave 436 mg (46%) of the title compound as a yellow solid.

MS (EI) m/z: 409 (M+).
m.p.: 123° C.
IR (KBr) v: 2930, 2862, 1638, 1609, 1531, 1435, 1304, 1204, 1171, 957, 797 cm$^{-1}$.
$^1$H-NMR (CDCl$_3$) δ: 8.37 (1 H, s), 7.65 (1 H, s), 7.53 (1 H, dd, J=2.2 and 8.9 Hz), 7.36 (1 H, d, J=8.9 Hz), 4.46 (3 H, s), 4.26 (2 H, t, J=7.7 Hz), 3.18 (2 H, t, J=6.8 Hz), 2.49 (3 H, s), 1.93–1.85 (4 H, m), 1.60–1.56 (2 H, m).
Anal. Calcd. for C$_{17}$H$_{20}$IN$_3$O: C, 49.89; H, 4.93; N, 10.27. Found: C, 50.21; H, 5.02; N, 10.30.

Example 51

(1,7-DIMETHYL-9-OXO-1,9-DIHYDRO-4H-PYRAZOLO[4,3-b]QUINOLIN-4-YL)ACETONITRILE.

The title compound was prepared according to the procedure of step 3 in EXAMPLE 47 using bromoacetonitrile instead of iodoethane.
MS (EI) m/z: 252 (M+).
m.p.: 214–219° C.
IR (KBr) v: 3103, 2361, 2341, 1634, 1607, 1533, 1479, 1435, 1306, 1286, 1184, 1040, 993, 959, 808 cm$^{-1}$.
$^1$H-NMR (DMSO-d$_6$) δ: 8.08 (1 H, s), 8.08–8.05 (1 H, m), 7.65–7.60 (2 H, m), 5.60 (2 H, s), 4.21 (3 H, s), 2.35 (3 H, s).
Anal. Calcd. for C$_{14}$H$_{12}$N$_4$O.0.1H$_2$O: C, 66.18; H, 4.84; N, 22.05. Found: C, 66.16; H, 4.80; N, 21.78.

Example 52

2-(1,7-DIMETHYL-9-OXO-1,9-DIHYDRO-4H-PYRAZOLO[4,3-b]QUINOLIN-4-YL)ACETAMIDE (CJ-022,972).

To a solution warmed at 85° C. of (1,7-dimethyl-9-oxo-1,9-dihydro-4H-pyrazolo[4,3-b]quinolin-4-yl)acetonitrile (EXAMPLE 51, 69 mg, 0.27 mmol) in 2-methyl-2-propanol (5 ml) was added powdered potassium hydroxide (76 mg, 1.4 mmol). The mixture was stirred at 85° C. for 10 min. After cooling to ca. 40° C., the mixture was poured into water (30 ml) and extracted with ethyl acetate (30 ml×3). The combined organic layer was washed with brine (50 ml), dried over magnesium sulfate, and concentrated in vacuo. The residue was washed with diisopropyl ether and ethyl acetate to give 43 mg (59%) of the title compound as a yellow solid.
MS (EI) m/z: 270 (M+).
m.p.: 247–252° C.
$^1$H-NMR (DMSO-d$_6$) δ: 8.02 (1 H, br s), 7.90 (1 H, s), 7.62 (1 H, br s), 7.48 (1 H, dd, J=2.4 and 8.9 Hz), 7.29 (1 H, d, J=8.9 Hz), 7.25 (1 H, br s), 4.87 (2 H, s), 4.20 (3 H, s), 2.32 (3 H, s).
Anal. Calcd. for C$_{14}$H$_{14}$N$_4$O$_2$.0.15C$_4$H$_8$O$_2$(ethyl acetate): C, 61.85; H, 5.40; N, 19.76.
Found: C, 61.46; H, 5.31; N, 19.92.

Example 53

1,7-DIMETHYL-4-[2-(METHYLSULFANYL)ETHYL]-1,4-DIHYDRO-9H-PYRAZOLO[4,3-b]QUINOLIN-9-ONE.

To a suspension of sodium hydride (60–72% in mineral oil, 225 mg, 5.6 mmol), which was washed with hexane and dried in vacuo, in N,N-dimethylformamide (40 ml) was added a solution of 1,7-dimethyl-1,4-dihydro-9H-pyrazolo[4,3-b]quinolin-9-one (EXAMPLE 47, step 2, 0.80 g, 3.75 mmol) in N,N-dimethylformamide at 0° C. The mixture was stirred at 0° C. for 10 min and at room temperature for 2 h. Chloromethyl methyl sulfide (0.87 ml, 7.5 mmol) was added at 0° C. and the mixture was stirred at room temperature for 10.5 h. Further more, sodium hydride (60–72% in mineral oil, 68 mg, 2.8 mmol) and chloromethyl methyl sulfide (0.87 ml, 7.5 mmol) were added. After 2 h, the mixture was heated at 50° C. for 15.5 h. The mixture was poured into brine (50 ml) and extracted with ethyl acetate (50 ml×2). The organic extracts were dried over magnesium sulfate and concentrated. Purification by column chromatography on silica gel eluting with ethyl acetate/hexane (1:1) gave 0.46 g (43%) of the title compound as a pale yellow solid.

MS (EI) m/z: 287 (M$^+$).

m.p.: 125° C.

IR (KBr) ν: 3099, 2922, 2860, 1636, 1603, 1528, 1477, 1439, 1308, 1296, 1271, 1254, 1202, 1178, 1099, 1047, 1003, 959, 800, 679, 667 cm$^{-1}$.

$^1$H-NMR (CDCl$_3$) δ: 8.36 (1 H, s), 7.68 (1 H, s), 7.54 (1 H, dd, J=2.3 and 8.7 Hz), 7.37 (1 H, d, J=8.7 Hz), 4.46 (3 H, s), 4.49–4.40 (2 H, m), 2.94 (2 H, t, J=7.6 Hz), 2.49 (3H, s), 2.19 (3H, s).

Anal. Calcd. for C$_{15}$H$_{17}$N$_3$OS: C, 62.69; H, 5.96; N, 14.62. Found: C, 62.48; H, 5.74; N, 14.54.

Example 54

4-[3-(DIMETHYLAMINO)PROPYL]-1,7-DIMETHYL-1,4-DIHYDRO-9H-PYRAZOLO[4,3-b]QUINOLIN-9-ONE HYDROCHLORIDE.

A mixture of 1,7-dimethyl-1,4-dihydro-9H-pyrazolo[4,3-b]quinolin-9-one (UK-264650) (EXAMPLE 47, step 2, 100 mg, 0.375 mmol), 3-(dimethylamino)propyl chloride hydrochloride (178 mg, 1.13 mmol) and potassium carbonate (311 mg, 2.25 mmol) in N,N-dimethylformamide (2 ml) was stirred at 100° C. for 6 h. After cooling to room temperature, water (50 ml) was added and extracted with ethyl acetate (50 ml×3). The combined organic layer was dried over magnesium sulfate and evaporated. To this residue (106 mg) was added methanolic hydrochloric acid and the mixture was concentrated in vacuo. The solid was recrystallized from ethanol/diisopropyl ether to give 99 mg (79%) of the title compound as a yellow solid.

MS (EI) m/z: 298 (M$^+$).

m.p.:240° C. (recrystallized from ethanol/diisopropyl ether).

IR (KBr) ν: 3499, 3425, 3084, 2940, 2680, 2475, 1641, 1611, 1533, 1477, 1443, 1313, 1184, 1043, 814,783 cm$^{-1}$.

$^1$H-NMR (DMSO-d$_6$) δ: 8.16 (1 H, br s), 8.14 (1 H, s), 7.75 (1 H, d, J=8.6 Hz), 7.63 (1 H, dd, J=2.2 and 8.6 Hz), 4.46 (2 H, t, J=7.3 Hz), 4.33 (3 H, s), 3.20–3.10 (2 H, m), 2.76 (6 H, s), 2.45 (3 H, s), 2.20–2.05 (2 H, m).

Anal. Calcd. for C$_{17}$H$_{22}$N$_4$O.HCl.0.8H$_2$O: C, 58.46; H, 7.10; N, 16.04. Found: C, 58.61; H, 7.03; N, 15.99.

Example 55

4-[2-(DIMETHYLAMINO)ETHYL]-1,7-DIMETHYL-1,4-DIHYDRO-9H-PYRAZOLO[4,3-b]QUINOLIN-9-ONE HYDROCHLORIDE.

The title compound was prepared according to the procedure of EXAMPLE 54 using 2-(dimethylamino)ethyl chloride hydrochloride instead of 3-(dimethylamino)propyl chloride hydrochloride.

MS (EI) m/z: 284 (M$^+$).

m.p.: 255° C. (recrystallized from methanol/diisopropyl ether).

IR (KBr) ν: 3485, 3423, 2926, 2581, 1463, 1638, 1609, 1537, 1481, 1441, 1310, 1290, 1207, 1192, 1011, 966, 814, 783 cm$^{-1}$.

$^1$H-NMR (DMSO-d$_6$) δ: 10.35 (1 H, br), 8.19 (1 H, s), 8.16 (1 H, br s), 7.78 (1 H, d, J=8.9 Hz), 7.66(1 H, dd, J=2.2 and 8.9 Hz), 4.85 (2 H, br s), 4.33 (3 H, s), 3.50–3.40 (2 H, m), 2.90 (6 H, s), 2.46 (3 H, s).

Anal. Calcd. for C$_{16}$H$_{20}$N$_4$O.HCl.0.7H$_2$O: C, 57.64; H, 6.77; N, 16.80. Found: C, 57.58; H, 6.67; N, 16.51.

Example 56

1,7-DIMETHYL-4-[2-(4-MORPHOLINYL)ETHYL-1,4-DIHYDRO-9H-PYRAZOLO[4,3-b]QUINOLIN-9-ONE HYDROCHLORIDE.

The title compound was prepared according to the procedure of EXAMPLE 54 using 4-(2-chloroethyl)morpholine hydrochloride instead of 3-(dimethylamino)propyl chloride hydrochloride.

MS (EI) m/z: 326 (M$^+$).

m.p.: 244–249° C. (recrystallized from methanol/diisopropyl ether).

IR (KBr) ν: 3430, 3082, 2874, 2386, 1636, 1601, 1529, 1477, 1443, 1315, 1207, 1192, 1132, 1094, 1034, 962, 872, 841, 827, 756 cm$^{-1}$.

$^1$H-NMR (DMSO-d$_6$) δ: 11.5 (1 H, br s), 8.30 (1 H, s), 8.19 (1 H, br s), 7.84 (1 H, d, J=8.4 Hz), 7.70 (1 H, dd, J=2.4 and 8.4 Hz), 4.92–4.81 (2 H, m), 4.36 (3 H, s), 4.12–4.00 (2 H, m), 3.91–3.78 (2 H, m), 3.65–3.45 (4 H, m), 2.49 (3 H, s). One signal due to CH$_2$ was not observed.

Anal. Calcd. for C$_{18}$H$_{22}$N$_4$O$_2$.HCl.0.1H$_2$O: C, 59.29; H, 6.41; N, 15.36. Found: C, 59.14; H, 6.46; N, 15.30.

Example 57

4-[4-(DIMETHYLAMINO)BUTYL]-1,7-DIMETHYL-14-DIHYDRO-9H-PYRAZOLO[4,3-b]QUINOLIN-9-ONE HYDROCHLORIDE.

Step 1. 4-(4-Iodobutyl)-1,7-dimethyl-1,4-dihydro-9H-pyrazolo[4,3-b]quinolin-9-one The title compound was prepared according to the procedure of EXAMPLE 50 using 1,4-diiodobutane instead of 1,5-diiodopentane.

MS (EI) m/z: 395 (M$^+$).

m.p.: 150° C.

IR (KBr) ν: 3736, 2950, 1638, 1601, 1522, 1508, 1474, 1437, 1313, 1178, 804 cm$^{-1}$.

H-NMR (CDCl$_3$) δ: 8.37 (1 H, br s), 7.66 (1 H, s), 7.54 (1 H, dd, J=2.4 and 8.6 Hz), 7.38 (1 H, d, J=8.6 Hz), 4.46 (3 H, s), 4.28 (2 H, t, J=7.0 Hz), 3.21 (2 H, t, J=6.3 Hz), 2.49 (3 H, s), 2.07–1.92 (4 H, m).

Anal. Calcd. for C$_{16}$H$_{18}$IN$_3$O.0.1C$_6$H$_{14}$: C, 49.37; H, 4.84; N, 10.40. Found: C, 49.30; H, 4.74; N, 10.41.

Step 2. 4-[4-(Dimethylamino)butyl]-1,7-dimethyl-1,4-dihydro-9H-pyrazolo[4,3-b]quinolin-9-one A mixture of 4-(4-iodobutyl)-1,7-dimethyl-1,4-dihydro-9H-pyrazolo[4,3-b]quinolin-9-one (EXAMPLE 57, step 1, 0.10 g, 0.25 mmol), an aqueous dimethylamine solution (abt. 50%, 91 mg, 1.0 mmol) and ethanol (10 ml) was refluxed for 9 h. 45 mg of the dimethylamine solution (0.5 mmol) was added and the resulting mixture was stirred for 1 h. The mixture was evaporated, basified with saturated aqueous sodium bicarbonate (30 ml), extracted with dichloromethane (30 ml×2) and dried over sodium sulfate. After concentration, the residue was purified by column chromatography on silica gel eluting with methanol/dichloromethane (1:9) to afford 75 mg (95%) of the title compound as a white solid.

Rf value: 0.35 (methanol/dichloromethane=1/9).

$^1$H-NMR (DMSO-d$_6$) δ: 8.14 (1 H, br s), 8.10 (1 H, s), 7.72 (1 H, d, J=8.6 Hz), 7.60 (1 H, dd, J=2.4 and 8.6 Hz), 4.39 (2 H, t, J=7.3 Hz), 4.32 (3 H, s), 2.43 (3 H, s), 2.24 (2 H, t, J=6.8 Hz), 2.11 (6 H, s), 1.75 (2 H, quint, J=7.8 Hz), 1.51 (2 H, quint, J=7.8 Hz).

Step 3. 4-[4-(Dimethylamino)butyl]-1,7-dimethyl-1,4-dihydro-9H-pyrazolo[4,3-B]quinolin-9-one hydrochloride 4-[4-(Dimethylamino)butyl]-1,7-dimethyl-1,4-dihydro-9H-pyrazolo[4,3-b]quinolin-9-one (EXAMPLE 57, step 2, 75 mg, 0.24 mmol) was treated with methanolic hydrochloric acid (2 ml). The mixture was concentrated to give a solid, which was recrystallized from 2-propanol. 51 mg (60%) of the title compound was obtained as a white solid.

MS (EI) m/z: 312 (M$^+$).

m.p.: 240° C. (recrystallized from 2-propanol).

IR (KBr) ν: 2924, 2565, 2469, 1638, 1607, 1533, 1487, 1433, 1312, 1203, 1188, 1053, 1001, 955, 826, 797, 783 cm$^{-1}$.

$^1$H-NMR (DMSO-d$_6$) δ: 8.15 (1 H, br s), 8.14 (1 H, s), 7.72 (1 H, d, J=9.2 Hz), 7.62 (1 H, dd, J=2.2 and 9.2 Hz), 4.45–4.38 (2 H, m), 4.32 (3 H, s), 3.08–3.00 (2 H, m), 2.70 (6 H, s), 2.44 (3 H, s), 1.80–1.70 (4 H, m).

Anal. Calcd. for C$_{18}$H$_{24}$N$_4$O.HCl.0.5H$_2$O: C, 60.41; H, 7.32; N, 15.65. Found: C, 60.23; H, 7.22; N, 15.54.

Example 58

4-[6-(DIMETHYLAMINO)HEXYL]-1,7-DIMETHYL-1,4-DIHYDRO-9H-PYRAZOLO[4,3-b]QUINOLIN-9-ONE HYDROCHLORIDE

Step 1. 4-(6-Iodohexyl)-1,7-dimethyl-1,4-dihydro-9H-pyrazolo[4,3-b]quinolin-9-one The title compound was prepared according to the procedure of EXAMPLE 50 using 1,6-diiodohexane instead of 1,5-diiodopentane.

MS (EI) m/z: 423 (M$^+$).

m.p.: 135° C.

IR (KBr)ν: 2939, 2853, 1638, 1601, 1528, 1474, 1435, 1308, 1173, 818, 802 cm$^{-1}$.

$^1$H-NMR (CDCl$_3$) δ: 8.37 (1 H, br s), 7.64 (1 H, s), 7.53 (1 H, dd, J=2.4 and 8.6 Hz), 7.37 (1 H, d, J=8.6 Hz), 4.47 (3 H, s), 4.25 (2 H, t, J=7.4 Hz), 3.18 (2 H, t, J=6.8 Hz), 2.49 (3 H, s), 1.92–1.79 (4 H, m), 0.48–1.45 (4 H, m).

Anal. Calcd. for C$_{18}$H$_{22}$IN$_3$O: C, 51.08; H, 5.24; N, 9.93. Found: C, 51.47; H, 5.41; N, 9.88.

Step 2. 4-[6-(Dimethylamino)hexyl]-1,7-dimethyl-1,4-dihydro-9H-pyrazolo[4,3-b]quinolin-9-one The title compound was prepared according to the procedure of step 2 in EXAMPLE 57 using 4-(6-iodohexyl)-1,7-dimethyl-1,4-dihydro-9H-pyrazolo[4,3-b]quinolin-9-one (EXAMPLE 58, step 1), instead of 4-(4-iodobutyl)-1,7-dimethyl-1,4-dihydro-9H-pyrazolo[4,3-b]quinolin-9-one.

Rf value: 0.35 (methanol/dichloromethane=1/9).

$^1$H-NMR (CDCl$_3$) δ: 8.36 (1 H, br s), 7.64 (1 H, s), 7.52 (1 H, dd J=2.2 and 9.2 Hz), 7.37 (1 H, d, J=9.2 Hz), 4.46 (3 H, s), 4.24 (2 H, t, J=7.6 Hz), 2.49 (3 H, s), 231×2.22 (2 H, m), 1.89–1.86 (2 H, m), 1.49–1.40 (6 H, m).

Step 3. 4-[6-(Dimethylamino)hexyl]-1,7-dimethyl-1,4-dihydro-9H-pyrazolo[4,3-b]quinolin-9-one hydrochloride The title compound was prepared according to the procedure of step 3 in EXAMPLE 57 using 4-[6-(dimethylamino)hexyl]-1,7-dimethyl-1,4-dihydro-9H-pyrazolo[4,3-b]quinolin-9-one (EXAMPLE 58, step 2), instead of 4-[4-(dimethylamino)butyl]-1,7-dimethyl-1,4-dihydro-9H-pyrazolo[4,3-b]quinolin-9-one.

MS (EI) m/z: 340 (M$^+$).

m.p.: 210° C. (recrystallized from 2-propanol/ethyl acetate).

IR (KBr) ν: 3452, 3364, 3267, 2945, 2719, 1638, 1601, 1531, 1474, 1433, 1312, 1209, 1180, 1161, 1101, 959, 818, 785 cm$^{-1}$.

$^1$H-NMR (CDCl$_3$) δ: 8.37 (1 H, s), 7.65 (1 H, s), 7.55 (1 H, d, J=9.2 Hz), 7.38 (1 H, d, J=8.8 Hz), 4.46 (3 H, s), 4.28 (2 H, t, J=7.9 Hz), 2.92 (2 H, m), 2.76 (6 H, s), 2.49 (3 H, s), 1.89 (4 H, m), 1.47 (4 H, m).

Anal. Calcd. for C$_{20}$H$_{28}$N$_4$O.HCl.2.5H$_2$O: C, 56.93; H, 8.12; N, 13.28. Found: C, 57.32; H, 8.37; N, 13.36.

Example 59

4-(3-AMINOPROPYL)-1,7-DIMETHYL-1,4-DIHYDRO-9H-PYRAZOLO[4,3-b]QUINOLIN-9-ONE HYDROCHLORIDE.

Step 1. A mixture of 4-(3-iodopropyl)-1,7-dimethyl-1,4-dihydro-9H-pyrazolo[4,3-b]quinolin-9-one and 4-allyl-1,7-dimethyl-1,4-dihydro-9H-pyrazolo[4,3-b]quinolin-9-one The title compounds were prepared as an inseparable mixture with a ratio of 1:1 according to the procedure of EXAMPLE 48 using 1,3-diiodopropane instead of 1-iodobutane.

Rf value: 0.26 (ethyl acetate/hexane=1/2).

Step 2. 4-(3-Azidopropyl)-1,7-dimethyl-1,4-dihydro-9H-pyrazolo[4,3-b]quinolin-9-one To a solution of an inseparable mixture of 4-(3-iodopropyl)-1,7-dimethyl-1,4-dihydro-9H-pyrazolo[4,3-b]quinolin-9-one and 4-allyl-1,7-dimethyl-1,4-dihydro-9H-pyrazolo[4,3-b]quinolin-9-one (EXAMPLE 59, step 1, 1.02 g) in N,N-dimethylformamide (15 ml) was added sodium azide (0.52 g, 8.0 mmol). The suspension was heated at 70° C. for 16 h and at 90° C. for 6 h. Water (30 ml) was added and the mixture was extracted with ethyl acetate (30 ml×2). The organic extracts were dried over sodium sulfate and concentrated to give a mixture of the title compound and 4-allyl-1,7-dimethyl-1,4-dihydro-9H-pyrazolo[4,3-b]quinolin-9-one with a ratio of 1:1 (0.91 g).

Rf value: 0.30 (ethyl acetate/hexane=1/1).

$^1$H-NMR (CDCl$_3$) of 4-(3-azidopropyl)-1,7-dimethyl-1,4-dihydro-9H-pyrazolo[4,3-b]quinolin-9-one δ: 8.36 (1 H, br s), 7.70 (1 H, s), 7.56–7.48 (1 H, m), 7.39 (1 H, d, J=8.6 Hz), 4.46 (3 H, s), 4.36 (2 H, t, J=7.2 Hz), 3.44 (2 H, t, J=6.1 Hz), 2.48 (3 H, s), 2.12 (2 H, quint, J=6.6 Hz).

Step 3. 4-(3-Aminopropyl)-1,7-dimethyl-1,4-dihydro-9H-pyrazolo[4,3-b]quinolin-9-one A mixture of 4-(3-azidopropyl)-1,7-dimethyl-1,4-dihydro-9H-pyrazolo[4,3-b]quinolin-9-one and 4-allyl-1,7-dimethyl-1,4-dihydro-9H-pyrazolo[4,3-b]quinolin-9-one (EXAMPLE 59, step 2, 0.93 g) was dissolved in ethanol (15 ml). The mixture was stirred, in the presence of 0.19 g of 10% palladium on carbon, for 5 h at room temperature under 4 atm of hydrogen. The mixture was filtered through a pad of Celite and the filtrate was concentrated in vacuo. The residue was purified by column chromatography on basic silica gel eluting with methanol/dichloromethane (1:100) to give 0.28 g of the title compound as a solid.

MS (EI) m/z: 270 (M$^+$).

$^1$H-NMR (DMSO-d$_6$) δ: 8.14 (1 H, br s), 8.10 (1 H, s), 7.73 (1 H, d, J=8.9 Hz), 7.60 (1 H, dd, J=1.9 and 8.9 Hz), 4.43 (2 H, t, J=7.2 Hz), 4.32 (3 H, s), 2.61 (2 H, t, J=6.6 Hz), 2.44 (3 H, s), 1.81 (2 H, quint, J=7.3 Hz). One signal due to NH$_2$ was not observed.

Step 4. 4-(3-Aminopropyl)-1,7-dimethyl-1,4-dihydro-9H-pyrazolo[4,3-b]quinolin-9-one hydrochloride The title compound was prepared according to the procedure of step 3 in EXAMPLE 57 using 4-(3-aminopropyl)-1,7-dimethyl-1,4-dihydro-9H-pyrazolo[4,3-b]quinolin-9-one (EXAMPLE 59, step 3), instead of 4-[4-(dimethylamino)butyl]-1,7-dimethyl-1,4-dihydro-9H-pyrazolo[4,3-b]quinolin-9-one.

MS (EI) m/z: 270 (M$^+$).

$^1$H-NMR (DMSO-d$_6$) δ: 8.18 (1 H, s), 8.16 (1 H, br s), 7.92 (2 H, br s), 7.76 (1 H, d, J=8.9 Hz), 7.63 (1 H, dd, J=2.2, 8.9 Hz), 4.97 (2 H, t, J=7.2 Hz), 4.32 (3 H, s), 2.96–2.86 (2 H, m), 2.45 (3 H, s), 2.09–1.98 (2 H, m). One signal due to NH$_2$ was not observed.

Example 60
N-[3-(1,7-DIMETHYL-9-OXO-1,9-DIHYDRO-4H-PYRAZOLO[4,3-b]QUINOLIN-4-YL)PROPYL] METHANESULFONAMIDE.

To a suspension of 4-(3-aminopropyl)-1,7-dimethyl-1,4-dihydro-9H-pyrazolo[4,3-b]quinolin-9-one (EXAMPLE 59, step 3, 0.10 g, 0.37 mmol) in dichloromethane (10 ml) were added 10 drops of pyridine and 10 drops of methanesulfonyl chloride at room temperature. The mixture was stirred at room temperature for 60 h, diluted with dichloromethane (40 ml) and washed with water (20 ml). The organic layer was washed with 2N hydrochloric acid (20 ml) and saturated aqueous sodium bicarbonate (20 ml), dried over sodium sulfate and evaporated. The residue was purified by column chromatography on silica gel eluting with methanol/dichloromethane (1:9). The obtained solid was recrystallized from ethyl acetate and hexane to give 29 mg (22%) of the title compound as a pale yellow solid.

MS (EI) m/z: 348 ($M^+$).
m.p.: 179° C. (recrystallized from ethyl acetate and hexane).
IR (KBr) v: 3140, 2910, 1640, 1599, 1528, 1439, 1329, 1155, 785 $cm^{-1}$.
$^1$H-NMR (CDCl$_3$) δ: 8.37 (1 H, br s), 7.68 (1 H, s), 7.54 (1 H, dd, J=2.4 and 8.9 Hz), 7.38 (1 H, d, J=8.9 Hz), 4.66 (3 H, s), 4.40 (2 H, t, J=7.4 Hz), 4.42–4.37 (1 H, m), 3.26 (2 H, q, J=6.4 Hz), 2.97 (3 H, s), 2.49 (3 H, s), 2.16 (2 H, quint, J=7.2 Hz).
Anal. Calcd. for $C_{16}H_{20}N_4O_3S \cdot 0.4H_2O$: C, 54.04; H, 5.90; N, 15.75. Found C, 54.13; H, 5.62; N, 15.50.

Example 61
4-{3-[ETHYL(METHYL)AMINO]PROPYL}-1,7-DIMETHYL-1,4-DIHYDRO-9H-PYRAZOLO[4,3-b]QUINOLIN-9-ONE HYDROCHLORIDE.

Step 1. 4-{3-[Ethyl(methyl)amino]propyl}-1,7-dimethyl-1,4-dihydro-9H-pyrazolo[4,3-b]quinolin-9-one The title compound was prepared according to the procedure of step 2 in EXAMPLE 57 using an inseparable mixture of 4-(3-iodopropyl)-1,7-dimethyl-1,4-dihydro-9H-pyrazolo[4,3-b]quinolin-9-one and 4-allyl-1,7-dimethyl-1,4-dihydro-9H-pyrazolo[4,3-b]quinolin-9-one (EXAMPLE 59, step 1) and N-ethylmethylamine instead of dimethylamine. The title compound and 4-allyl-1,7-dimethyl-1,4-dihydro-9H-pyrazolo[4,3-b]quinolin-9-one were separable by column chromatography on silica gel eluting with methanol/dichloromethane (1:9).

Rf value: 0.30 (methanol/dichloromethane=1/9).
$^1$H-NMR (DMSO-d$_6$) δ: 8.14 (1 H, br s), 8.04 (1 H, s), 7.71 (1 H, d, J=8.6 Hz), 7.61 (1 H, dd, J=1.9 and 8.6 Hz), 4.39 (2 H, t, J=7.0 Hz), 4.32 (3 H, s), 2.44 (3 H, s), 2.37–2.28 (4 H, m), 2.12 (3 H, s), 1.87 (2 H, quint, J=6.8 Hz), 0.98 (3 H, t, J=7.0 Hz).

Step 2. 4-{3-[Ethyl(methyl)amino]propyl}-1,7-dimethyl-1,4-dihydro-9H-pyrazolo[4,3-b]quinolin-9-one hydrochloride The title compound was prepared according to the procedure of step 3 in EXAMPLE 57 using 4-{3-[ethyl(methyl)amino]propyl}-1,7-dimethyl-1,4-dihydro-9H-pyrazolo[4,3-b]quinolin-9-one (EXAMPLE 61, step 1), instead of 4-[4-(dimethylamino)butyl]-1,7-dimethyl-1,4-dihydro-9H-pyrazolo[4,3-b]quinolin-9-one.

MS (EI) m/z: 312 ($M^+$).
m.p.: 213° C. (recrystallized from diisopropyl ether).
IR (KBr) v: 3418, 2951, 2687, 1638, 1609, 1531, 1477, 1445, 1313, 1186, 1047, 820 $cm^{-1}$.
$^1$H-NMR (CDCl$_3$) δ: 8.36 (1 H, m), 7.75 (1 H, s), 7.62–7.56 (1 H, m), 7.48 (1 H, d, J=8.1 Hz), 4.55–4.51 (2 H, m), 4.45 (3 H, s), 3.14 (2 H, m), 2.95 (2 H, m), 2.69 (3 H, d, J=5.1 Hz), 2.65–2.45 (2 H, m), 2.48 (3 H, s), 1.38 (3 H, t, J=7.2 Hz).

Example 62
4-(2-CHLOROETHYL)-1,7-DIMETHYL-1,4-DIHYDRO-9H-PYRAZOLO[4,3-b]QUINOLIN-9-ONE (CJ-023,230).

Step 1. 4-[2-(Benzyloxy)ethyl]-1,7-dimethyl-1,4-dihydro-9H-pyrazolo 4,3-b]quinolin-9-one The title compound was prepared according to the procedure of step 3 in EXAMPLE 47 using benzyl 2-bromoethyl ether instead of iodoethane.

MS (EI) m/z: 347 ($M^+$).
m.p.:116–119° C.
IR (KBr) v: 2920, 2830, 1638, 1607, 1531, 1477, 1437, 1310, 1213, 1123, 1042, 804, 733, 694 $cm^{-1}$.
$^1$H-NMR (DMSO-d$_6$) δ: 8.14 (1 H, br s), 8.04 (1 H, s), 7.74 (1 H, d, J=9.0 Hz), 7.57 (1 H, dd, J=2.1 and 8.7 Hz), 7.24–7.18 (3 H, m), 7.09–7.02 (2 H, m), 4.64 (2 H, t, J=5.1 Hz), 4.41 (2 H, s), 4.31 (3 H, s), 3.82 (2 H, t, J=4.8 Hz), 2.44 (3 H, s).
Anal. Calcd. for $C_{21}H_{21}N_3O_2$: C, 72.60; H, 6.09; N, 12.09. Found: C, 72.51; H, 6.08; N 12.05.

Step 2. 4-(2-Hydroxyethyl)-1,7-dimethyl-1,4-dihydro-9H-pyrazolo[4,3-b]quinolin-9-one A mixture of 4-[2-(benzyloxy)ethyl]-1,7-dimethyl-1,4-dihydro-9H-pyrazolo[4,3-b]quinolin-9-one (EXAMPLE 62, step 1, 670 mg, 1.93 mmol) and 10% palladium on carbon (500 mg) in acetic acid (30 ml) was stirred at room temperature under hydrogen atmosphere (4 atm) for 12 h. The mixture was filtered through a pad of Celite, and the filtrate was concentrated in vacuo to give 498 mg (100%) of the title compound as a yellow solid.

MS (EI) m/z: 257 ($M^+$).
m.p.: 214–215° C.
IR (KBr) v: 3364, 3123, 1722, 1638, 1597, 1529, 1441, 1310, 1263, 1207, 1082, 1061, 1040, 962, 850, 806, 783 $cm^{-1}$.
$^1$H-NMR (DMSO-d$_6$) δ: 8.13 (1 H, br s), 8.01 (1 H, s), 7.72 (1 H, d, J=7.58 (1 H, dd, J=1.9 and 8.6 Hz), 4.90 (1 H, t, J=5.7 Hz), 4.45 (2 H, t, J=5.7 Hz), 4.31 (3 H, s), 3.79 (2 H, t, J=5.1 Hz), 2.43 (3 H, s).

Step 3. 4-(2-Chloroethyl)-1,7-dimethyl-1,4-dihydro-9H-pyrazolo[4,3-b]quinolin-9-one To a solution of 4-(2-hydroxyethyl)-1,7-dimethyl-1,4-dihydro-9H-pyrazolo[4,3-b]quinolin-9-one (EXAMPLE 62, step 2, 468 mg, 1.82 mmol) in tetrahydrofuran (10 ml) and N,N-dimethylformamide (5 ml) was added dropwise thionyl chloride (0.20 ml, 2.7 mmol). After stirring at room temperature for 2 h, the mixture was concentrated in vacuo, poured into water (100 ml) and extracted with ethyl acetate (100 ml×3). The combined organic layer was dried over magnesium sulfate and evaporated. The residue was chromatographed on a column of silica gel eluting with ethyl acetate/hexane (1:1.5 to ethyl acetate only) to give 151 mg (30%) of the title compound as a white solid.

MS (EI) m/z: 275 ($M^+$).
m.p.: 196° C.
IR (KBr) v: 1638, 1607, 1533, 1475, 1443, 1313, 1271, 1204, 1188, 1151, 1011, 957, 808, 785, 743, 665 $cm^{-1}$.
$^1$H-NMR (DMSO-d$_6$) δ: 8.15 (1 H, br s), 8.10 (1 H, s), 7.74 (1 H, d, J=9.2 Hz), 7.61 (1 H, dd, J=2.4 and 8.9 Hz), 4.81 (2 H, t, J=6.5 Hz), 4.32 (3 H, s), 4.04 (2 H, t, J=6.2 Hz), 2.44 (3 H, s).
Anal. Calcd. for $C_{14}H_{14}ClN_3O$: C, 60.98; H, 5.12; N, 15.24. Found: C, 61.05; H, 5.24; N, 15.13.

Example 63
4-(2-AMINOETHYL)-1,7-DIMETHYL-1,4-DIHYDRO-9H-PYRAZOLO[4,3-b]QUINOLIN-9-ONE HYDROCHLORIDE.

Step 1. 4-(2-Azidoethyl)-1,7-dimethyl-1,4-dihydro-9H-pyrazolo[4,3-b]quinolin-9-one To a solution of 4-(2-chloroethyl)-1,7-dimethyl-1,4-dihydro-9H-pyrazolo[4,3-b]quinolin-9-one (EXAMPLE 62, step 3, 109 mg, 0.396 mmol) in N,N-dimethylformamide (7 ml) was added sodium azide (77 mg, 1.2 mmol) at room temperature. The resulting mixture was heated at 70° C. for 9.5 h. After cooling to room temperature, water (50 ml) was added and extracted with ethyl acetate (50 ml×3). The combined organic layer was dried over magnesium sulfate and concentrated in vacuo to give 110 mg (99%) of the title compound as a yellow solid.

Rf value: 0.38 (ethyl acetate/hexane=2/1).

$^1$H-NMR (DMSO-$d_6$) δ: 8.15 (1 H, br s), 8.10 (1 H, s), 7.77 (1 H, d, J=8.9 Hz), 7.62 (1 H, dd, J=3.0 and 8.6 Hz), 4.65 (2 H, t, J=5.4 Hz), 4.32 (3 H, s), 3.78 (2 H, t, J=5.8 Hz), 2.44 (3 H, s).

Step 2. 4-(2-Aminoethyl)-1,7-dimethyl-1,4-dihydro-9H-pyrazolo[4,3-b]quinolin-9-one hydrochloride A mixture of 4-(2-azidoethyl)-1,7-dimethyl-1,4-dihydro-9H-pyrazolo[4,3-b]quinolin-9-one (EXAMPLE 63, step 1, 110 mg, 0.391 mmol) and 10% palladium on carbon (150 mg) in a mixture of ethanol (15 ml) and tetrahydrofuran (5 ml) was stirred at room temperature for 6 h under hydrogen atmosphere (4 atm). The catalyst was removed by filtration through a pad of Celite and the filtrate was concentrated in vacuo. The residue was treated with methanolic hydrochloric acid (5 ml) and the obtained solid was recrystallized from methanol/diisopropyl ether to give 50 mg (44%) of the title compound as a yellow solid.

MS (EI) m/z: 256 (M$^+$).

m.p.: >280° C. (recrystallized from methanol/diisopropyl ether).

$^1$H-NMR (DMSO-$d_6$) δ: 8.16 (1 H, br s), 8.13 (1 H, s), 8.09 (2 H, br s), 7.73 (1 H, d, J=8.6 Hz), 7.65 (1 H, dd, J=1.1 and 8.4 Hz), 4.63 (2 H, t, J=7.0 Hz), 4.33 (3 H, s), 3.20 (2 H, br s), 2.45 (3 H, s).

Anal. Calcd. for $C_{14}H_{16}N_4O\cdot HCl\cdot 0.8H_2O$: C, 54.74; H, 6.10; N, 18.24. Found: C, 54.94; H, 6.22; N, 17.94.

Example 64
1,7-DIMETHYL-4-(4-PIPERIDINYL)-1,4-DIHYDRO-9H-PYRAZOLO[4,3-b]QUINOLIN-9-ONE.

Step 1. tert-Butyl 4-(1,7-dimethyl-9-oxo-1,9-dihydro-4H-pyrazolo[4,3-b]quinolin-4-yl)-1-piperidinecarboxylate A mixture of 1,7-dimethyl-1,4-dihydro-9H-pyrazolo[4,3-b]quinolin-9-one (EXAMPLE 47, step 2, 0.1 g, 0.47 mmol), tert-butyl 4-[(methylsulfonyl)oxy]-1-piperidinecarboxylate ((Leeson et al., *Bioorg. Med. Chem. Lett.*, 1999, 9, 1285), 0.66 g, 2.4 mmol) and potassium carbonate (0.13 g, 0.94 mmol) in dimethylsulfoxide (15 ml) was heated at 85° C. for 46.5 h. The reaction mixture was diluted with toluene/ethyl acetate (1:3, 30 ml), washed with water (30 ml), and dried over sodium sulfate. Removal of solvent gave a residue, which was chromatographed on a column of silica gel eluting with ethyl acetate/hexane (1:1) to afford 49 mg (26%) of the title compound as a pale brown solid.

Rf value: 0.55 (ethyl acetate/dichloromethane/toluene=20/20/1).

$^1$H-NMR (CDCl$_3$) δ: 8.38 (1 H, s), 7.72 (1 H, s), 7.58–7.46 (2 H, m), 4.85–4.68 (1 H, m), 4.45 (3 H, s), 4.45–4.37 (2 H, m), 2.99–2.88 (2 H, m), 2.59–2.48 (2 H, m), 2.48 (3 H, s), 1.91–1.87 (2 H, m) 1.54 (9 H, s).

Step 2. 1,7-Dimethyl-4-(4-piperidinyl)-1,4-dihydro-9H-pyrazolo[4,3-b]quinolin-9-one To a solution of tert-butyl 4-(1,7-dimethyl-9-oxo-1,9-dihydro-4H-pyrazolo[4,3-b]quinolin-4-yl)-1-piperidinecarboxylate (EXAMPLE 64, step 1, 62 mg, 0.16 mmol) in dichloromethane (5 ml) was added trifluoroacetic acid (0.03 ml, 0.39 mmol) and the mixture was stirred at room temperature for 7 h and at 45° C. for 21 h. After evaporation, the residue was dissolved in dichloromethane (20 ml), washed with saturated aqueous sodium bicarbonate (20 ml) and dried over sodium sulfate. Removal of solvent gave 22 mg (47%) of the title compound as a white solid.

MS (EI) m/z: 296 (M$^+$).

$^1$H-NMR (DMSO-$d_6$) δ: 8.32 (1 H, s), 8.26 (1 H, br s), 7.98 (1 H, d, J=9.0 Hz), 7.58 (1 H, dd, J=2.4 and 9.0 Hz), 4.32 (3 H, s), 3.13–3.09 (2 H, m), 2.79–2.72 (3 H, m), 2.50–2.46 (2 H, m), 2.46 (3 H, s), 1.68 (2 H, m). One signal due to NH was not observed.

Example 65
1,7-DIMETHYL-4-(1-METHYL-4-PIPERIDINYL)-1,4-DIHYDRO-9H-PYRAZOLO[4,3-b]QUINOLIN-9-ONE HYDROCHLORIDE.

Step 1. 1,7-Dimethyl-4-(1-methyl-4-piperidinyl)-1,4-dihydro-9H-pyrazolo[4,3-b]quinolin-9-one To a solution of 1,7-dimethyl-4-(4-piperidinyl)-1,4-dihydro-9H-pyrazolo[4,3-b]quinolin-9-one (EXAMPLE 64, step 2, 34 mg, 0.11 mmol) in tetrahydrofuran (1 ml) was added a mixture of 3M sulfuric acid (56 μl, 0.17 mmol) and formalin (29 mg) at 0° C. Sodium borohydride (5.1 mg, 0.14 mmol) was added and the resulting mixture was stirred at room temperature for 12 h. The mixture was treated with 2N sodium hydroxide (20 ml) and extracted with ethyl acetate (20 ml×2). The organic extracts were dried over sodium sulfate and evaporated. The obtained residue was purified by preparative thin layer chromatography developing with methanol/dichloromethane (1:9) to afford 24 mg (67%) of the title compound as a white solid.

MS (EI) m/z: 310 (M$^+$).

$^1$H-NMR (DMSO-$d_6$) δ: 8.15 (1 H, br s), 8.08 (1 H, s), 7.92 (1 H, d, J=9.0 Hz), 7.59 (1 H, dd, J=2.4 and 9.0 Hz), 4.32 (3 H, s), 3.00–2.90 (2 H, m), 2.73–2.25 (5 H, m), 2.43 (3 H, s), 1.78–1.75 (2 H, m).

Step 2. 1,7-Dimethyl-4-(1-methyl-4-piperidinyl)-1,4-dihydro-9H-pyrazolo[4,3-b]quinolin-9-one hydrochloride The title compound was prepared according to the procedure of step 3 in EXAMPLE 57 using 1,7-dimethyl-4-(1-methyl-4-piperidinyl)-1,4-dihydro-9H-pyrazolo[4,3-b]quinolin-9-one (EXAMPLE 65, step 1), instead of 4-[4-(dimethylamino)butyl]-1,7-dimethyl-1,4-dihydro-9H-pyrazolo[4,3-b]quinolin-9-one.

MS (EI) m/z: 310 (M$^+$).

$^{-1}$H-NMR (DMSO-$d_6$) δ: 8.37 (1 H, s), 8.17 (1 H, br s), 7.98 (1 H, d, J=12 Hz), 7.66–7.62 (1 H, m), 4.33 (3 H, s), 3.67–3.58 (2 H, m), 3.00–2.27 (5 H, m), 2.44 (3 H, s), 2.05–1.97 (2 H, m).

Example 66
4-{[(DIMETHYLAMIHNO)METHYL]PHENYL}-1,7-DIMETHYL-1,4-DIHYDRO-9H-PYRAZOLO[4,3-b]QUINOLIN-9-ONE HYDROCHLORIDE Step 1. 4-{[(dimethylamino)methyl]phenyl}-1,7-dimethyl-1,4-dihydro-9H-pyrazolo[4,3-b]quinolin-9-one A mixture of 1,7-dimethyl-1,4-dihydro-9H-pyrazolo[4,3-b]quinolin-9-one (EXAMPLE 47, step 2, 0.25 g, 1.2 mmol), 1-(4-iodophenyl)-N,N-dimethylmethanamine ((Stanko et al., *J. Org. Chem. USSR* (*Engl. Transl.*), 1985, 21, 514), 1.53 g, 5.9 mmol), copper (II) oxide (0.125 g, 1.57 mmol) and potassium carbonate (0.81 g, 5.9 mmol) in N,N-dimethylformamide (15 ml) was refluxed for 45 h. After cooling to room temperature, the mixture was filtered through a pad of Celite. The filtrate was evaporated and the obtained solid was washed with water and 2-propanol to give 159 mg (39%) of the title compound as a white solid.
MS (EI) m/z: 346 (M⁺).
$^1$H-NMR (DMSO-d$_6$) δ: 8.18 (1 H, br s), 7.61 (2 H, d, J=8.1 Hz), 7.49 (2 H, d, J=8.1 Hz), 7.50–7.46 (1 H, m), 7.19 (1 H, s), 6.91 (1 H, d, J=8.6 Hz), 4.35 (3 H, s), 3.58–3.52 (2 H, br), 2.34 (3 H, s), 2.24 (6 H, s).
Step 2. 4-{[(dimethylamino)methyl]phenyl}-1,7-dimethyl-1,4-dihydro-9H-pyrazolo[4,3-b]quinolin-9-one hydrochloride The title compound was prepared according to the procedure of step 3 in EXAMPLE 57 using 4-{[(dimethylamino)methyl]phenyl}-1,7-dimethyl-1,4-dihydro-9H-pyrazolo[4,3-b]quinolin-9-one (EXAMPLE 66, step 1), instead of 4-[4-(dimethylamino)butyl]-1,7-dimethyl-1,4-dihydro-9H-pyrazolo[4,3-b]quinolin-9-one. Recrystallization from diisopropyl ether gave 56 mg (32%) of the title compound
m.p.: >300° C. (recrystallized from diisopropyl ether).
IR(KBr)v:2947, 2633, 2509, 2467, 1641, 1611, 1518, 1475, 1437, 1310, 1207, 1157, 961, 818 cm$^{-1}$.
$^1$H-NMR (DMSO-d$_6$) δ: 8.19 (1 H, br s), 7.86 (2 H, d, J=8.6 Hz), 7.68 (2 H, d, J=8.1 Hz), 7.47 (1 H, dd, J=1.9 and 8.9 Hz), 7.27 (1 H, s), 6.94 (1 H, d, J=8.9 Hz), 4.44 (2 H, d, J=4.6 Hz), 4.35 (3 H, s), 2.83 (3 H, s), 2.81 (3 H, s), 2.44 (3 H, s).

Example 67
1-METHYL-5,6,7,8-TETRAHYDRO-1H-PYRAZOLO[4,3-b]QUINOLIN-9-OL.

A solution of 1-methyl-1H-pyrazol-4-amine ((J. Catalan et al., *J. Heterocycl. Chem.*, 1985, 22, 997), 200 mg, 2.06 mmol), 2-oxocyclohexanecarboxylate (351 mg, 2.06 mmol), and p-toluenesulfonic acid monohydrate (10 mg, 0.05 mmol) in toluene (20 ml) was stirred at 120° C. for 2.5 h. After cooling to room temperature, the solvent was removed in vacuo. Diphenyl ether (5 ml) was added to the residue (ca. 300 mg) and the resulting mixture was heated at 240° C. for 40 min. After cooling to room temperature, hexane (2 ml) was added. The precipitate was collected by filtration and washed with dichloromethane to give 190 mg (46%) of the title compound as a white solid.
MS (EI) m/z: 203 (M⁺).
m.p.: >300° C.
IR (KBr) v: 3244, 3045, 2928, 1583, 1525, 1429, 1389, 1313, 1167, 932, 823, 810, 502 cm$^{-1}$.
$^1$H-NMR (DMSO-d$_6$) δ: 11.41 (1 H, br s), 7.61 (1 H, s), 4.19 (3 H, s), 2.66 (2 H, t, J=5.7 Hz), 2.42 (2 H, t, J=5.7 Hz), 1.77–1.61 (4 H, m).
Anal. Calcd. for C$_{11}$H$_{13}$N$_3$O.0.1H$_2$O: C, 64.44; H, 6.49; N, 20.49. Found: C, 64.49; H, 6.43; N, 20.81.

Example 68
7-BENZYL-1-METHYL-5,6,7,8-TETRAHYDRO-1H-PYRAZOLO[4,3-b]QUINOLIN-9-OL HYDROCHLORIDE.

The title compound was prepared according to the procedure of step 4 in EXAMPLE 67 using ethyl 5-benzyl-2-oxocyclohexanecarboxylate (G. A. Russell and L. O. Ochrymowycz, *J. Org. Chem.*, 1969, 34, 3624) instead of 2-oxocyclohexanecarboxylate.
MS (EI) m/z: 293 (M⁺).
m.p.: >250° C.
IR (KBr) v: 2926, 2856, 1599, 1537, 1495, 1391, 1215, 1177, 1130, 1099, 826, 750, 702, 660 cm$^{-1}$.
$^1$H-NMR (DMSO-d$_6$) δ: 11.56 (1 H, br s), 7.62 (1 H, s), 7.35–7.20 (5 H, m), 4.18 (3 H, s), 2.75–2.60 (5 H, m), 2.00–1.80 (3 H, m), 1.45–1.30 (1 H, m).

Example 69
7-(4-CHLOROBENZYL)-1-METHYL-5,6,7,8-TETRAHYDRO-1H-PYRAZOLO[4,3-b]QUINOLIN-9-OL HYDROCHLORIDE.
Step 1. 8-(4-Chlorobenzyl)-1,4-dioxaspiro[4.5]decane
A mixture of 8-(4-chlorobenzylidene)-1,4-dioxaspiro[4.5]decane ((A. Rosowsky et al., *J. Med. Chem.*, 1999, 42, 1007), 8.20 g, 31.0 mmol) and 5% palladium on carbon (500 mg) in ethanol (150 ml) was stirred at room temperature for 3 h under hydrogen atmosphere (1 atm). The mixture was filtered through a pad of Celite and the filtrate was concentrated in vacuo. The residue was chromatographed on a column of silica gel eluting with ethyl acetate/hexane (1:9) to give 3.94 g (48%) as a colorless oil.
Rf value: 0.36 (ethyl acetate/hexane=1/5).
$^1$H-NMR (CDCl$_3$) δ: 7.24 (2 H, J=11.6 Hz), 7.06 (2 H, d, J=8.4 Hz), 3.93 (4 H, s), 2.50 (2 H, d, J=7.0 Hz), 1.78–1.60 (4 H, m), 1.60–1.42 (3 H, m), 1.35–1.19 (2 H, m).
Step 2. 4-(4-Chlorobenzyl)cyclohexanone
A solution of 8-(4-chlorobenzyl)-1,4-dioxaspiro[4.5]decane (EXAMPLE 69, step 1, 3.94 g, 14.8 mmol) in a mixture of 2N hydrochloric acid (20 ml) and tetrahydrofuran (40 ml) was stirred at room temperature for 27 h. Diethyl ether (150 ml) and water (100 ml) were added, and the separated aqueous layer was extracted with diethyl ether (100 ml). The combined organic layer was washed with brine (100 ml), dried over magnesium sulfate and evaporated. The residue was chromatographed on a column of silica gel eluting with ethyl acetate/hexane (1:5) to give 2.81 g (85%) of the title compound as a colorless oil.
Rf value: 0.22 (ethyl acetate/hexane=1/5).
$^1$H-NMR (CDCl$_3$) δ: 7.27 (2 H, d, J=8.2 Hz), 7.10 (2 H, d, J=8.2 Hz), 2.58 (2 H, d, J=6.8 Hz), 2.42–2.21 (4 H, m), 2.07–1.92 (3 H, m), 2.07–1.92 (3 H, m), 1.53–1.35 (2 H, m).
Step 3. Ethyl 5-(4-chlorobenzyl)-2-oxocyclohexanecarboxylate
To a suspension of sodium hydride (60–72% in mineral oil, 1.51 g, 37.9 mmol), which was washed with hexane 3 times, and diethyl carbonate (3.73 g, 31.5 mmol) in benzene (100 ml) was added dropwise a solution of 4-(4-chlorobenzyl)cyclohexanone (EXAMPLE 69, step 2, 2.81 g, 12.6 mmol) in benzene (20 ml) at 80° C. The mixture was stirred at 80° C. for 3.5 h. After cooling to 0° C., saturated aqueous ammonium chloride (500 ml) was carefully added and the crude product was extracted with ethyl acetate (500 ml×3). The combined organic layer was dried over magnesium sulfate and concentrated in vacuo. The residue was chromatographed on a column of silica gel eluting with ethyl acetate/hexane (1:10) to give 1.43 g of the title compound as a colorless oil.
Rf value: 0.59 (ethyl acetate/hexane=1/5).
Step 4. 7-(4-Chlorobenzyl)-1-methyl-5,6,7,8-tetrahydro-1H-pyrazolo[4,3-b]quinolin-9-ol hydrochloride
A solution of 1-methyl-1H-pyrazol-4-amine ((J. Catalan et al., *J. Heterocycl. Chem.*, 1985, 22, 997), 200 mg, 2.06 mmol), ethyl 5-(4-chlorobenzyl)-2-oxocyclohexane-carboxylate (EXAMPLE 69, step 3, 1.43 g, 4.85 mmol), and p-toluenesulfonic acid monohydrate (10 mg, 0.05 mmol) in toluene (15 ml) was stirred at 120° C. for 2.5 h. After cooling to room temperature, the solvent was removed in vacuo. The residue (ca. 1.5 g) was dissolved in diphenyl ether (10 ml) and heated at 240° C. for 1 h. After cooling to room temperature, the formed solid was collected by filtration, and washed with diisopropyl ether to give 231 mg (34%) of 7-(4-chlorobenzyl)-1-methyl-5,6,7,8-tetrahydro-1H- pyrazolo[4,3-b]quinolin-9-ol. 105 mg of this compound was treated with methanolic hydrochloric acid (5 ml) and the mixture was evaporated. The obtained solid was recrystallized from methanol/diisopropyl ether to give 100 mg of the title compound as a gray crystal.

MS (EI) m/z: 327 (M+).

m.p.:279° C. (recrystallized from methanol/diisopropyl ether).

IR (KBr) ν: 3323, 2716, 1645, 1601, 1541, 1491, 1408, 1391, 1310, 1254, 1090, 999, 845 cm$^{-1}$.

$^1$H-NMR (DMSO-d$_6$) δ: 11.80 (1 H, br s), 7.65 (1 H, s), 7.36 (2 H, d, J=8.4 Hz), 7.26 (2 H, d, J=8.4 Hz), 4.18 (3 H, s), 2.76–2.60 (5 H, m), 2.00–1.80 (3 H, m), 1.48–1.30 (1 H, m).

Anal. Calcd. for $C_{18}H_{18}ClN_3O \cdot HCl \cdot H_2O$: C, 56.55; H, 5.54; N, 10.99. Found: C, 56.27; H, 5.57; N, 10.84.

Example 70–Example 84

The compounds disclosed hereinafter were prepared according to the following procedure:

General reaction Scheme:

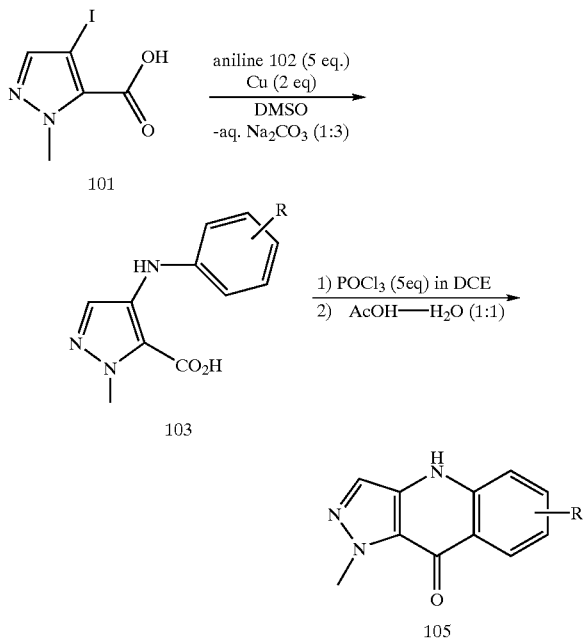

Protocols

1. Reaction Protocols

Materials:

1$^{st}$ step
 aniline 102 (993 μmol), halide 101 (397 μmol), Cu (60 mg), DMSO (1.1 ml), 5% aqueous Na$_2$CO$_3$ (3.3 ml), Kanto extreluteNE3

2$^{nd}$ step
 POCl$_3$ (20 μL), 1,2-dichloroethane (0.2 ml)

3$^{rd}$ step
 AcOH—H$_2$O (1:1, 0.3 ml)

Procedure:

Step 1.

A mixture of 4-iodo-1-methyl-1H-pyrazole-5-carboxylic acid ((Manaev, Yu. A. et al., *J. Gen. Chem. USSR* (*Engl. Transl.*), 1982, 52, 2291) 101 (397 μmol), aniline 102 (993 μmol), and copper powder (60 mg) in a mixture of dimethylsulfoxide and 5% aqueous sodium carbonate (4.4 ml) was shaken at 100° C. and after 12 h the reaction mixture was cooled to room temperature. Then to the mixture was added ethyl acetate (3 ml). This operation was done by L-COS. To the mixture was added 6N hydrochloric acid (460 μl) to adjust pH 3–4. The acidified solution was loaded onto Kanto extreluteNE3. The organic layer was eluted with 5 ml. The residue (about 90 mg) obtained after Nitrogen flow (70° C., Turbo Vap®LV Evaporator, Zymark) were purified with preparative LC/MS to give the desired product 103.

Step 2.

A mixture of the coupling product 3 (about 10 mg), phosphorous oxychloride (20 μl), and 1,2-dichloroethane (0.2 ml) was shaken at 100° C. After 80 min, the reaction mixture was concentrated in vacuo to provide the crude Chloride substituted product 104.

Step 3.

To 104 was added aqueous acetic acid at room temperature and the mixture was stirred at 100° C. for 18 h. After cooled, to the mixture was added 0.3 ml of methanol and the solution was purified by preparative LC/MS to give 105.

2. HPLC/LC-MS Method

MS Condition:
 ionization method: ESI positive
 equipment: micromass ZMD

Preparative Conditions:
 Crude products were purified using LC/MS system.
 column: C18
 column temp.: ambient temperature
 flow: 1.0 mL/min.
 solvent:
  A: 0.1% HCOOH aq.
  B: MeOH
 gradient:B20–90%

Example 70

1,6,7-TRIMETHYL-1,4-DIHYDRO-9H-PYRAZOLO[4,3-b]QUINOLIN-9-ONE and 1,7,8-TRIMETHYL-1,4-DIHYDRO-9H-PYRAZOLO[4,3-b]QUINOLIN-9-ONE.

MS (ESI) m/z 228.25 (M+H)$^+$.

Example 71

7-ISOPROPYL-1,6-DIMETHYL-1,4-DIHYDRO-9H-PYRAZOLO[4,3-b]QUINOLIN-9-ONE and 7-ISOPROPYL-1,8-DIMETHYL-1,4-DIHYDRO-9H-PYRAZOLO[4,3-b]QUINOLIN-9-ONE.

MS (ESI) m/z 256.27 (M+H)$^+$.

Example 72

5-CHLORO-1,8-DIMETHYL-1,4-DIHYDRO-9H-PYRAZOLO[4,3-b]QUINOLIN-9-ONE.

MS (ESI) m/z 248.22 (M+H)$^+$.

Example 73

6-FLUORO-1,5-DIMETHYL-1,4-DIHYDRO-9H-PYRAZOLO[4,3-b]QUINOLIN-9-ONE.

MS (ESI) m/z 232.25 (M+H)$^+$.

Example 74

8-CHLORO-5-METHOXY-1-METHYL-1,4-DIHYDRO-9H-PYRAZOLO[4,3-b]QUINOLIN-9-ONE.

MS (ESI) m/z 264.21 (M+H)$^+$.

Example 75

7-FLUORO-1,5-DIMETHYL-1,4-DIHYDRO-9H-PYRAZOLO[4,3-b]QUINOLIN-9-ONE.

MS (ESI) m/z 232.25 (M+H)$^+$.

Example 76

5-FLUORO-1,7-DIMETHYL-1,4-DIHYDRO-9H-PYRAZOLO[4,3-b]QUINOLIN-9-ONE.

MS (ESI) m/z 232.27 (M+H)$^+$.

Example 77
1,5,7-TRIMETHYL-1,4-DIHYDRO-9H-PYRAZOLO[4,3-b]QUINOLIN-9-ONE.
MS (ESI) m/z 228.29 (M+H)+.

Example 78
8-(OR 6-)METHOXY-1-METHYL-1,4-DIHYDRO-9H-PYRAZOLO[4,3-b]QUINOLIN-9-ONE.
MS (ESI) m/z 230.26 (M+H)+.

Example 79
6-(OR 8-)-METHOXY-1-METHYL-1,4-DIHYDRO-9H-PYRAZOLO[4,3-b]QUINOLIN-9-ONE.
MS (ESI) m/z 230.27 (M+H)+.

Example 80
7-FLUORO-1,6-DIMETHYL-1,4-DIHYDRO-9H-PYRAZOLO[4,3-b]QUINOLIN-9-ONE and 7-FLUORO-1,8-DIMETHYL-1,4-DIHYDRO-9H-PYRAZOLO[4,3-b]QUINOLIN-9-ONE.
MS (ESI) m/z 231.08 (M+H)+.

Example 81
6,7-DIFLUORO-1-METHYL-1,4-DIHYDRO-9H-PYRAZOLO[4,3-b]QUINOLIN-9-ONE and 7,8-DIFLUORO-1-METHYL-1,4-DIHYDRO-9H-PYRAZOLO[4,3-b]QUINOLIN-9-ONE.
MS (ESI) m/z 235.06 (M+H)+.

Example 82
6-FLUORO-1,7-DIMETHYL-1,4-DIHYDRO-9H-PYRAZOLO[4,3-b]QUINOLIN-9-ONE and 8-FLUORO-1,7-DIMETHYL-1,4-DIHYDRO-9H-PYRAZOLO[4,3-b]QUINOLIN-9-ONE.
MS (ESI) m/z 231.08 (M+H)+.

Example 83
5,8-DICHLORO-1-METHYL-1,4-DIHYDRO-9H-PYRAZOLO[4,3-b]QUINOLIN-9-ONE.
MS (ESI) m/z 267.00 (M+H)+.

Example 84
1-METHYL-7-(METHYLSULFANYL)-1,4-DIHYDRO-9H-PYRAZOLO[4,3-b]QUINOLIN-9-ONE.
MS (ESI) m/z 245.06 (M+H)+.

Example 85–Example 91

The compounds disclosed hereinafter were prepared according to the following procedure:

General Reaction Scheme:

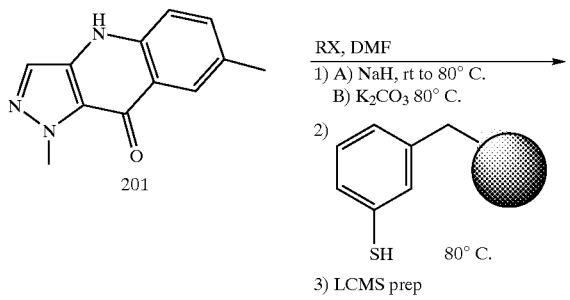

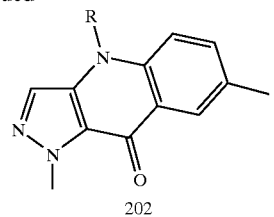

202

1. Reaction Protocols
Materials:
Halide 202 (150 μmol), pyrazoloquinoline 201 (75 μmol), NaH (60%, oil dispersion), K$_2$CO$_3$, PS-thiophenol (1.43 mmol/g, Argonaut)
Procedure:
A mixture of halide 202 (150 μmol), pyrazoloquinoline 201 (75 μmol), and sodium hydride in N,N-dimethylformamide (0.5 ml) was stirred at room temperature. After 30 min the mixture was heated to 80° C. for 12 h. Then the reaction mixture was cooled to room temperature. To the mixture was added N,N-dimethylformamide (1.5 ml) and PS-thiophenol (157 mg). The suspension was stirred slowly at 80° C. for 10 h. After cooled, the mixture was loaded onto Varian bond elute reservoir (8 ml) to remove the resin. The filtrate was concentrated with nitrogen gas flow (70° C., Turbo Vap®LV Evaporator, Zymark). The obtained residue (about 20–40 mg) was purified by preparative LC/MS to give the desired product 202.

2. HPLC/LC-MS Method
Analytical conditions:
MS Condition:
  ionization method: ESI positive
Preparative conditions:
  equipment: LC/MS system
  column: C18
  column temp.: ambient temperature
  flow: 1.0 mL/min.
  solvent:
  A: 0.1% HCOOH aq.
  B: MeOH
  gradient:B 10–90%

Example 85
4-[3-(DIMETHYLAMINO)-2-METHYLPROPYL]-1,7-DIMETHYL-1,4-DIHYDRO-9H-PYRAZOLO[4,3-b]QUINOLIN-9-ONE.
MS (ESI) m/z 313.36 (M+H)+.

Example 86
1,7-DIMETHYL-4-[2-(1-METHYL-2-PIPERIDINYL)ETHYL]-1,4-DIHYDRO-9H-PYRAZOLO[4,3-b]QUINOLIN-9-ONE.
MS (ESI) m/z 339.3 (M+H)+.

Example 87
1,7-DIMETHYL-4-(3-PYRIDINYLMETHYL)-1,4-DIHYDRO-9H-PYRAZOLO[4,3-b]QUINOLIN-9-ONE.
MS (ESI) m/z 305.23 (M+H)+.

Example 88
5-(1,7-DIMETHYL-9-OXO-1,9-DIHYDRO-4H-PYRAZOLO[4,3-b]QUINOLIN-4-YL)PENTANENITRILE.
MS (ESI) m/z 295.29 (M+H)+.

Example 89
4-(1H-BENZIMIDAZOL-2-YLMETHYL)-1,7-DIMETHYL-1,4-DIHYDRO-9H-PYRAZOLO[4,3-b]QUINOLIN-9-ONE.
MS (ESI) m/z 421.39 (M+H)+.

Example 90

1,7-DIMETHYL-4-[3-(METHYLAMINO)PROPYL]-1,4-DIHYDRO-9H-PYRAZOLO[4,3-b]QUINOLIN-9-ONE.

MS (ESI) m/z 321.46 (M+H)$^+$.

Example 91

1,7-DIMETHYL-4-[2-(1-METHYL-2-PYRROLIDINYL) ETHYL]-1,4-DIHYDRO-9H-PYRAZOLO[4,3-b] QUINOLIN-9-ONE.

MS (ESI) m/z 339.5 (M+H)$^+$.

Example 92–Example 107

The compounds disclosed hereinafter were prepared according to the following procedure:

Step 1. 4-[2-(1,3-Dioxolan-2-yl)ethyl]-1,7-dimethyl-1,4-dihydro-9H-pyrazolo[4,3-b]quinolin-9-one To a solution of 1,7-dimethyl-1,4-dihydro-9H-pyrazolo[4,3-b]quinolin-9-one (EXAMPLE 47, step 2, 6.39 g, 30.0 mmol) in N,N-dimethylformamide (100 ml) was added sodium hydride (60–72% in mineral oil, 1.56 g, 39.0 mmol) at 0° C. After stirring at 0° C. for 30 min, 2-(2-bromoethyl)-1,3-dioxolane (14.1 ml, 120 mmol) was added dropwise at 0° C. The resulting mixture was allowed to warm up to room temperature and stirred for 3 h. After cooling to 0° C., water (500 ml) was added to the mixture and extracted with ether (400 ml×8). The combined organic layer was washed with water (100 ml) and evaporated to give 8.71 g (93%) of the title compound as a yellow solid.

Rf value: 0.35 (ethyl acetate/hexane=2/1).

$^1$H-NMR (CDCl$_3$) δ: 8.35 (1 H, s), 7.75 (1 H, s), 7.54 (1 H, dd, J=2.2 and 11.6 Hz), 7.43 (1 H, d, J=11.3 Hz), 4.97 (1 H, t, J=3.9 Hz), 4.46 (3 H, s), 4.47–4.37 (2 H, m), 4.09–3.89 (4 H, m), 2.48 (3 H, s), 2.29–2.20 (2 H, m).

Step 2. 3-(1,7-Dimethyl-9-oxo-1,9-dihydro-4H-pyrazolo[4,3-b]quinolin-4-yl)propanal A solution of 4-[2-(1,3-dioxolan-2-yl)ethyl]-1,7-dimethyl-1,4-dihydro-9H-pyrazolo[4,3-b]quinolin-9-one (step 1, 8.18 g, 26.1 mmol) in 50% aqueous acetic acid (240 ml) was heated with stirring at 100° C. for 2 h. After cooling to room temperature, the mixture was basified with saturated sodium bicarbonate (500 ml) and extracted with dichloromethane (250 ml×7). The combined organic layer was washed with saturated sodium bicarbonate (500 ml), dried over magnesium sulfate, and concentrated in vacuo. The residue was chromatographed on a column of silica gel eluting with ethyl acetate/hexane (2:1 to 3:1) to give 3.72 g (53%) of the title compound (301) as a pale yellow solid.

MS (EI) m/z: 269 (M$^+$).
m.p.: 169° C.
IR (KBr) ν: 2833, 1713, 1638, 1601, 1531, 1475, 1437, 1375, 1321, 1312, 1205, 1182, 1151, 957, 808 cm$^{-1}$.
$^1$H-NMR (CDCl$_3$) δ: 9.90 (1 H, s), 8.37 (1 H, br s), 7.69 (1 H, s), 7.54 (1 H, d, J=8.9 Hz), 7.33 (1 H, d, J=8.9 Hz), 4.61 (2 H, t, J=7.1 Hz), 4.45 (3 H, s), 3.49 (3 H, s), 3.07 (3H, t, J=7.2 Hz), 2.49 (3 H, s).
Anal. Calcd. for C$_{15}$H$_{15}$N$_3$O$_2$.0.15H$_2$O: C, 66.24; H, 5.67; N, 15.45. Found: C, 66.27; H, 5.61; N, 15.22.

General Reaction Scheme:

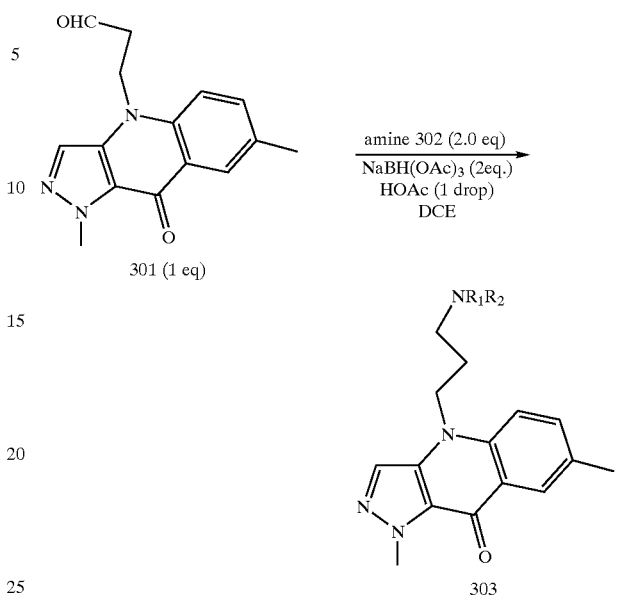

Protocols

1. Reaction Protocols

Materials:
amine 302 (111 μmol), aldehyde 301 (15 mg, 56 μmol), NaH(OAc)$_3$ (111 μmol), AcOH (1 drop), DCE (0.750 ml), PS—NCO (argonaut, 1.0–1.7 mmol/g)

Procedure:
To a mixture of the above obtained aldehyde (301, 15.0 mg, 56 μmol) and amine 302 (0.111 mmol) in 1,2-dichloroethane (0.25 ml) were added sodium triacetoxyborohydride (23.5 mg, 0.111 mmol) in 1,2-dichloroethane (0.5 ml) and acetic acid. The mixture was agitated at room temperature for 24 h and loaded onto a BondElute® SCX cartridge (500 mg/3 ml; purchased from Varian) preconditioned with 1 ml of methanol. The solid-phase matrix was washed with 5 ml of methanol and then eluted with 2M ammonia/methanol (3 ml). The product was dried in Savant for 4 h and then the mixture was treated with PS—NCO (111 mg) in tetrahydrofuran (1 ml) at 55° C. After 18 h, PS—NCO was filtrated and the eluent was concentrated to dryness by nitrogen gas blow and vacuum centrifuge to give the product 303 with excellent purity.

A product with low purity after SPE-SCX was further purified by semi prep.

2. HPLC/LC-MS Method

Analytical conditions:
MS condition:
  ionization method: ESI positive
Preparative conditions:
LC conditions:
  column: C18
  column temp.: ambient temperature
  detector: photodiodearray (210–400 nm)
  flow: 1.0 mL/min.
  solvent:
    A: 0.1% HCOOH aq.
    B: MeOH
    Condition a) gradient: B20–90%

Example 92
4-[3-(1-AZETIDINYL)PROPYL]-1,7-DIMETHYL1,4-DIHYDRO-9H-PYRAZOLO[4,3-b]QUINOLIN-9-ONE.
MS (ESI) m/z 311.28 (M+H)+.

Example 93
1,7-DIMETHYL-4-(3-{METHYL[2-(2-PYRIDINYL)ETHYL]AMINO}PROPYL)-1,4-DIHYDRO-9H-PYRAZOLO[4,3-b]QUINOLIN-9-ONE.
MS (ESI) m/z 390.41 (M+H)+.

Example 94
4-[3-(DIETHYLAMINO)PROPYL]-1,7-DIMETHYL-1,4-DIHYDRO-9H-PYRAZOLO[4,3-b]QUINOLIN-9-ONE.
MS (ESI) m/z 327.4 (M+H)+.

Example 95
4-{3-[ISOPROPYL(METHYL)AMINO]PROPYL}-1,7-DIMETHYL-1,4-DIHYDRO-9H-PYRAZOLO[4,3-b]QUINOLIN-9-ONE.
MS (ESI) m/z 398.47 (M+H)+.

Example 96
4-{3-[(2-HYDROXYETHYL)(ISOPROPYL)AMINO]PROPYL}-1,7-DIMETHYL-1,4-DIHYDRO-9H-PYRAZOLO[4,3-b]QUINOLIN-9-ONE.
MS (ESI) m/z 327.4 (M+H)+.

Example 97
4-{3-[BIS(2-HYDROXYETHYL)AMINO]PROPYL}-1,7-DIMETHYL-1,4-DIHYDRO-9H-PYRAZOLO[4,3-b]QUINOLIN-9-ONE.
MS (ESI) m/z 357.4 (M+H)+.

Example 98
4-{3-[(2-HYDROXYETHYL)(METHYL)AMINO]PROPYL}-1,7-DIMETHYL-1,4-DIHYDRO-9H-PYRAZOLO[4,3-b]QUINOLIN-9-ONE.
MS (ESI) m/z 359.39 (M+H)+.

Example 99
4-{3-[ETHYL(PROPYL)AMINO]PROPYL}-1,7-DIMETHYL-1,4-DIHYDRO-9H-PYRAZOLO[4,3-b]QUINOLIN-9-ONE.
MS (ESI) m/z 329.38 (M+H)+.

Example 100
1,7-DIMETHYL-4-[3-(4-METHYL-1,4-DIAZEPAN-1-YL)PROPYL]-1,4-DIHYDRO-9H-PYRAZOLO[4,3-b]QUINOLIN-9-ONE.
MS (ESI) m/z 341.42 (M+H)+.

Example 101
4-{3-[HEXYL(METHYL)AMINO]PROPYL}-1,7-DIMETHYL-1,4-DIHYDRO-9H-PYRAZOLO[4,3-b]QUINOLIN-9-ONE.
MS (ESI) m/z 368.44 (M+H)+.

Example 102
{BUTYL[3-(1,7-DIMETHYL-9-OXO-1,9-DIHYDRO-4H-PYRAZOLO[4,3-b]QUINOLIN-4-YL)PROPYL]AMINO}ACETONITRILE.
MS (ESI) m/z 369.45 (M+H)+.

Example 103
4-{3-[[2-(DIETHYLAMINO)ETHYL](METHYL)AMINO]PROPYL}-1,7-DIMETHYL-1,4-DIHYDRO-9H-PYRAZOLO[4,3-b]QUINOLIN-9-ONE.
MS (ESI) m/z 366.41 (M+H)+.

Example 104
3-[[3-(1,7-DIMETHYL-9-OXO-1,9-DIHYDRO-4H-PYRAZOLO[4,3-b]QUINOLIN-4-YL)PROPYL](METHYL)AMINO]PROPANENITRILE.
MS (ESI) m/z 384.47 (M+H)+.

Example 105
1,7-DIMETHYL-4-{3-[METHYL(2-PHENYLETHYL)AMINO]PROPYL}-1,4-DIHYDRO-9H-PYRAZOLO[4,3-b]QUINOLIN-9-ONE.
MS (ESI) m/z 389.42 (M+H)+.

Example 106
4-{3-[ETHYL(2-HYDROXYETHYL)AMINO]PROPYL}-1,7-DIMETHYL-1,4-DIHYDRO-9H-PYRAZOLO[4,3-b]QUINOLIN-9-ONE.
MS (ESI) m/z 343.40 (M+H)+.

Example 107
4-[3-(3,4-DIHYDRO-2(1H)-ISOQUINOLINYL)PROPYL]1-1,7-DIMETHYL-1,4-DIHYDRO-9H-PYRAZOLO[4,3-b]QUINOLIN-9-ONE
MS (ESI) m/z 387.39 (M+H)+.

The chemical structures of the compounds of Formula (I) prepared in the Examples 1 to 107 are summarized in the following table.

The compounds of this invention represented by Formula (I), wherein $R^1$ is $CH_3$, $Y^5$ to $Y^8$ are absent and the dashed lines represent double bond. (hereinafter represented by Formula ($It^1$)), prepared in the above working examples are summarized in the following table.

The following abbreviations have the indicated meanings:

Me=methyl

Et=ethyl i-Pr=isopropyl n-Bu=normal butyl

Bn=benzyl

Ph=phenyl

Ms=mesyl.

TABLE

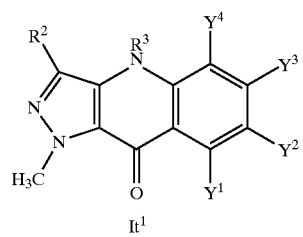

| Ex.# | R2 | R3 | Y1 | Y2 | Y3 | Y4 |
|---|---|---|---|---|---|---|
| 1 | H | H | H | F | H | H |
| 2 | H | H | H | H | H | F |
| 3 | H | H | H | H | F | H |
| 4 | H | H | F | H | H | H |
| 5 | H | H | H | H | H | Br |
| 6 | H | H | H | Et | H | H |
| 7 | H | H | H | H | H | Et |
| 8 | H | H | Et | H | H | H |
| 9 | H | H | H | H | Et | H |
| 10 | H | H | iPr | H | H | H |
| 11 | H | H | H | Bn | H | H |
| 12 | NH$_2$ | H | H | Me | H | H |
| 13 | H | H | H | 4-Cl-Bn | H | H |
| 14 | H | H | H | 3-Cl-Bn | H | H |
| 15 | H | H | H | 2-Cl-Bn | H | H |
| 16 | H | H | H | 4-MeO-Bn | H | H |
| 17 | H | H | H | 4-HO-Bn | H | H |
| 18 | H | H | H | 4-[2-(dimethylamino)ethoxy]benzyl | H | H |
| 19 | H | H | H | 3-MeO-Bn | H | H |
| 20 | H | H | H | 3-HO-Bn | H | H |
| 21 | H | H | H | 2-MeO-Bn | H | H |
| 22 | H | H | H | 2-HO-Bn | H | H |
| 23 | H | H | H | 3-nitrobenzyl | H | H |
| 24 | H | H | H | 3-H$_2$N-Bn | H | H |
| 25 | H | H | H | 2-H$_2$N-Bn | H | H |
| 26 | H | H | H | 4-NC-Bn | H | H |
| 27 | H | H | H | 4-H$_2$NH$_2$C-Bn | H | H |
| 28 | H | H | H | 3-NC-Bn | H | H |
| 29 | H | H | H | 3-H$_2$N(O=)C-Bn | H | H |
| 30 | H | H | H | 3-HO(O=)C-Bn | H | H |
| 31 | H | H | H | 3-H$_2$NH$_2$C-Bn | H | H |
| 32 | H | H | H | 2-H$_2$N(O=)C-Bn | H | H |
| 33 | H | H | Et | 2-H$_2$NH$_2$C-Bn | H | H |
| 34 | H | H | H | 2-H$_2$N(H$_2$C)$_2$-Bn | H | H |
| 35 | H | H | H | 3-pyridylmethyl | H | H |
| 36 | H | H | H | hydroxy(phenyl)methyl | H | H |
| 37 | H | H | H | H | H | Ph |
| 38 | H | H | 4-HO-Ph | H | H | H |
| 39 | H | H | 3-HO-Ph | H | H | H |
| 40 | H | H | H | 3-HO-Ph | H | H |
| 41 | H | H | 4-H$_2$N-Ph | H | H | H |
| 42 | H | H | H | ⟨CH=CH-CO$_3$Et⟩ | H | H |
| 43 | H | H | H | —(CH$_2$)$_2$CN | H | H |
| 44 | H | H | H | —(CH$_2$)$_3$NH$_2$ | H | H |
| 45 | H | H | H | —NHPh | H | H |
| 46 | H | H | H | —NHC(=O)Ph | H | H |
| 47 | H | ethyl | H | Me | H | H |
| 48 | H | n-butyl | H | Me | H | H |
| 49 | H | n-hexyl | H | Me | H | H |
| 50 | H | 5-iodohexyl | H | Me | H | H |
| 51 | H | —CH$_2$CN | H | Me | H | H |
| 52 | H | —CH$_2$C(=O)NH$_2$ | H | Me | H | H |
| 53 | H | —(CH$_2$)$_2$SMe | H | Me | H | H |
| 54 | H | 3-(dimethylamino)propyl | H | Me | H | H |
| 55 | H | 2-(dimethylamino)ethyl | H | Me | H | H |
| 56 | H | 2-(4-morpholinyl)ethyl | H | Me | H | H |
| 57 | H | 4-(dimethylamino)butyl | H | Me | H | H |
| 58 | H | 6-(dimethylamino)hexyl | H | Me | H | H |
| 59 | H | —(CH$_2$)$_3$NH$_2$ | Et | Me | H | H |
| 60 | H | —(CH$_2$)$_3$NHMs | H | Me | H | H |
| 61 | H | 3-[ethyl(methyl)amino]propyl | H | Me | H | H |

TABLE-continued

| | | | | | | | |
|---|---|---|---|---|---|---|---|
| 62 | H | —(CH$_2$)$_2$Cl | H | Me | | H | H |
| 63 | H | —(CH$_2$)$_2$NH$_2$ | H | Me | | H | H |
| 64 | H | 4-piperidinyl | H | Me | | H | H |
| 65 | H | 1-methyl-4-piperidinyl | H | Me | | H | H |
| 66 | H | 4-[(dimethylamino)methyl]phenyl | H | Me | | H | H |

| Ex.# | compounds |
|---|---|
| 67 | 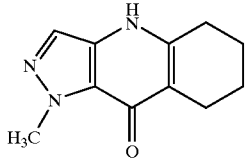 |
| 68 | 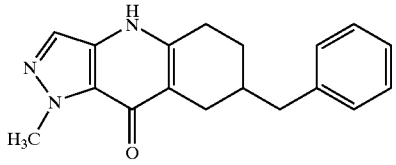 |
| 69 | 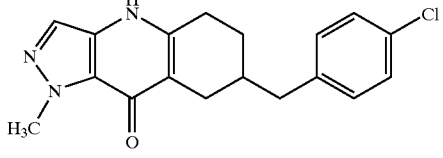 |

| Ex.# | R2 | R3 | Y1 | Y2 | Y3 | Y4 |
|---|---|---|---|---|---|---|
| 70 | H | H | H | Me | Me | H |
| 70 | H | H | Me | Me | H | H |
| 71 | H | H | H | iPr | Me | H |
| 71 | H | H | Me | iPr | H | H |
| 72 | H | H | Me | H | H | Cl |
| 73 | H | H | H | H | F | Me |
| 74 | H | H | Cl | H | H | OMe |
| 75 | H | H | H | F | H | Me |
| 76 | H | H | H | Me | H | F |
| 77 | H | H | H | Me | H | Me |
| 78, 79 | H | H | H | H | OMe | H |
| 78, 79 | H | H | OMe | H | H | H |
| 80 | H | H | H | F | Me | H |
| 80 | H | H | Me | F | H | H |
| 81 | H | H | H | F | F | H |
| 81 | H | H | F | F | H | H |
| 82 | H | H | H | Me | F | H |
| 82 | H | H | F | Me | H | H |
| 83 | H | H | Cl | H | H | Cl |
| 84 | H | H | H | SMe | H | H |
| 85 | H | 3-(dimethylamino)-2-methylpropyl | H | Me | H | H |
| 86 | H | 2-(1-methyl-2-piperidinyl)ethyl | H | Me | H | H |
| 87 | H | 3-pyridinylmethyl | H | Me | H | H |
| 88 | H | —(CH$_2$)$_4$CN | H | Me | H | H |
| 89 | H | 1H-benzimidazol-2-ylmethyl | H | Me | H | H |
| 90 | H | —(CH$_2$)$_3$NHMe | H | Me | H | H |
| 91 | H | (1-methyl-2-pyrrolidinyl)ethyl | H | Me | H | H |
| 92 | H | (1-azetidinyl)propyl | H | Me | H | H |
| 93 | H | 3-{methyl[2-(2-pyridinyl)ethyl]amino}propyl | H | Me | H | H |
| 94 | H | 3-(diethylamino)propyl | H | Me | H | H |
| 95 | H | 3-[isopropyl(methyl)amino]propyl | H | Me | H | H |
| 96 | H | 3-[2-hydroxyethyl(isopropyl)amino]propyl | H | Me | H | H |
| 97 | H | 3-[bis(2-hydroxyethyl)amino]propyl | H | Me | H | H |
| 98 | H | 3-[(2-hydroxyethyl)(methyl)amino]propyl | H | Me | H | H |
| 99 | H | 3-[ethyl(propyl)amino]propyl | H | Me | H | H |
| 100 | H | 3-(4-methyl-1,4-diazepan-1-yl)propyl | H | Me | H | H |

| | | | | | | |
|---|---|---|---|---|---|---|
| 101 | H | 3-[hexyl(methyl)amino]propyl | H | Me | H | H |
| 102 | H | 3-[butyl(cyanomethyl)amino]propyl | H | Me | H | H |
| 103 | H | 3-[[2-(diethylamino)ethyl](methyl)amino]propyl | H | Me | H | H |
| 104 | H | 3-[2-cyanoethyl(methyl)amino]propyl | H | Me | H | H |
| 105 | H | 3-[methyl(2-phenylethyl)amino]propyl | H | Me | H | H |
| 106 | H | 3-[ethyl(2-hydroxyethyl)amino]propyl | H | Me | H | H |
| 107 | H | 3-(3,4-dihydro-2-(1H)-isoquinolinyl)propyl | H | Me | H | H |

That which is claimed is:

1. A compound of the formula (I):

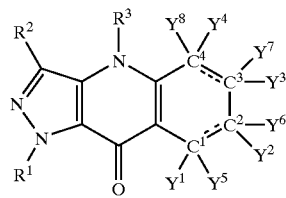

or the pharmaceutically acceptable salts thereof wherein the dashed lines represent optional double bonds;

$R^1$ is $C_{1-4}$ alkyl;

$R^2$ is H, amino, mono- or di-($C_{1-4}$alkyl)amino or $C_{1-3}$ alkyl-(O=)CNH—;

$R^3$ is H, halo-$CH_2$—, $R^4(R^5)NCH_2$—, $R^6(R^7)NC(=O)CH_2$—, cyano-$CH_2$—, $Q^1CH_2$—, $Q^1$-(O=)CCH_2$—, $C_{2-8}$ alkyl or $Q^1$-, wherein said $C_{2-8}$ alkyl is optionally substituted with up to 3 substituents selected from halo, $C_{1-3}$ alkyl, $R^4(R^5)N$, $C_{1-4}$ alkylsulfonylamino, $C_{1-4}$ alkylthio, $R^6(R^7)NC(=O)$—, cyano, $Q^1$-, $Q^1$-(O=)C— and $Q^1$-$C_{1-4}$ alkyl-O—;

$Y^1$, $Y^2$, $Y^3$ and $Y^4$ are independently selected from hydrogen, halo, $C_{1-4}$ alkyl, $C_{1-4}$ alkyl-O—, $C_{1-4}$ alkylthio, $Q^1$-, $R^6(R^8)N$—, $R^6N(R^7)C(=O)$—, $C_{1-4}$alkyl-O(O=)CCH=CH—, $Q^1$-(O=)CNH— and $R^6OC(=O)$—, wherein said $C_{1-4}$alkyl is optionally substituted with up to 2 substituents selected from $Q^1$, $Q^2$-, $R^6(R^7)N$—, cyano, hydroxy and $R^6(R^7)NC(=O)$—;

$Y^5$, $Y^6$, $Y^7$ and $Y^8$ are hydrogen or are absent;

$C^1$, $C^2$, $C^3$ and $C^4$ are carbon atom;

$R^4$ is H, $C_{1-7}$ alkyl, HO—$C_{1-4}$ alkyl, $Q^1$-, $Q^1$-$C_{1-4}$alkyl-, cyano- $C_{1-4}$ alkyl- or $R^6(R^7)N$ $C_{1-4}$ alkyl-;

$R^5$ is H, $C_{1-7}$alkyl, HO—$C_{1-4}$ alkyl or $Q^1$-;

$R^6$ and $R^7$ are independently selected from H and $C_{1-4}$ alkyl $R^8$ is aryl or heteroaryl;

$Q^1$ is a 4–12 membered monocyclic or bicyclic aromatic, partially saturated or fully saturated ring optionally containing up to 4 heteroatoms selected from O, N and S, and is optionally substituted with halo, $C_{1-4}$ alkyl, amino, hydroxy, $R^6(R^7)NC_{1-4}$alkyl- or $R^6(R^7)NC_{1-4}$alkyl-O—; and $Q^2$ is a 5–12 membered monocyclic or bicyclic aromatic, partially saturated or fully saturated ring optionally containing up to 3 heteroatoms selected from O, N and S, and is optionally substituted with halo, $C_{1-4}$alkyl-, hydroxy, $C_{1-4}$ alkoxy, nitro, amino, cyano, $R^6(R^7)N$—$C_{1-4}$alkyl-, $R^6(R^7)N$—$C_{1-4}$alkyl-O—, $R^6(R^7)N(O=)C$— or $R^6O(O=)C$—;

with the proviso that when $R^1$ is methyl and $R^2$ and $R^3$ are H, $Y^1$, $Y^2$, $Y^3$ and $Y^4$ are not H simultaneously; and when $R^1$ is methyl and $R^2$ and $R^3$ are H, $Y^2$ is not chloro.

2. A compound according to claim 1, wherein $R^1$ is $C_{1-2}$ alkyl.

3. A compound according to claim 1, wherein $R^1$ is methyl.

4. A compound according to claim 1, wherein $R^2$ is H or amino.

5. A compound according to claim 1, wherein $R^2$ is H.

6. A compound according to claim 1, wherein $R^3$ is H, halo-$CH_2$—, $R^4(R^5)NCH_2$—, $R^6(R^7)NC(=O)CH_2$—, cyano-$CH_2$—, $Q^1CH_2$—, $Q^1$-(O=)CCH_2$—, $C_{2-6}$ alkyl or $Q^1$-, wherein said $C_{2-6}$ alkyl is optionally substituted with up to 3 substituents selected from halo, methyl, $R^4(R^5)N$, $C_{1-2}$ alkylsulfonylamino, $C_{1-2}$ alkylthio, $R^6(R^7)NC(=O)$—, cyano, $Q^1$- and $Q^1$-(O=)C—, wherein $R^4$ is H, $C_{1-6}$ alkyl, HO—$C_{1-2}$ alkyl, $Q^1$-, $Q^1$-$C_{1-3}$alkyl-, cyano- $C_{1-2}$alkyl- or $R^6(R^7)N$ $C_{1-2}$alkyl-; $R^5$ is H, $C_{1-2}$alkyl, HO—$C_{1-2}$ alkyl or $Q^1$-; $R^6$ and $R^7$ are independently selected from H and $C_{1-2}$ alkyl; and $Q^1$ is a 4–10 membered monocyclic or bicyclic aromatic, partially saturated or frilly saturated ring optionally containing up to 2 heteroatoms selected from O and N, and is optionally substituted with halo, $C_{1-2}$ alkyl, hydroxy, amino, $R^6(R^7)N$ $C_{1-2}$alkyl- or $R^6(R^7)NC_{1-2}$alkyl-O—.

7. A compound according to claim 1, wherein $R^3$ is hydrogen, ethyl, butyl, hexyl, iodopentyl, carbamoylmethyl, methylthioethyl, (N,N-dimethylamino)ethyl, morpholino ethyl, (N,N-dimethylamino)butyl, (N,N-dimethylamino)hexyl, methansulfonylaminopropyl, (N-ethyl-N-methylamino)propyl, chloroethyl, aminoethyl, [(N,N-dimethylamino)methyl]phenyl, (N,N-dimethylamino)(methyl)propyl, (1-methyl-2-piperidinyl)ethyl, pyridylmethyl, cyanobutyl, 2-benzimidazolylmethyl, (N-methylamino)propyl, (1-methyl-2-pyrrolidinyl)ethyl, (1-azetidinyl)propyl, {N-methyl-N-[(pyridinyl)ethyl]amino}propyl, (N,N-diethylamino)propyl, [N-isopropyl-N-(methyl)amino]propyl, [N-(2-hydroxyethyl)-N-(isopropyl)amino]propyl, [N,N-bis(2-hydroxyethyl)amino]propyl, [N-(hydroxyethyl)-N-(methyl)amino]propyl, [N-ethyl-N-(propyl)amino]

propyl, (4-methyl-1,4-diazepan-1-yl)propyl, [N-hexyl-N-(methyl)amino]propyl, [N-(cyanomethyl)-N-(propyl)amino]propyl, [N-[(diethylamino)ethyl]-N-(methyl)amino]propyl, [N-(cyanomethyl)-N-(methyl)amino]propyl, [N-methyl-N-(phenylethyl)amino]propyl, [N-ethyl-N-(hydroxyethyl)amino]propyl, (3,4-dihydro-2(1H)-isoquinolinyl)propyl, N-methyl-piperidyl, (N,N-dimethylamino)propyl, piperidyl, aminopropyl or cyanomethyl.

8. A compound according to claim 1, wherein
$R^3$ is H, ethyl, n-butyl, n-hexyl, 5-iodopentyl, carbamoylmethyl, 2-methylthioethyl, 2-(N,N-dimethylamino)ethyl, 2-morpholinoethyl, 4-(N,N-dimethylamino)butyl, 6-(N,N-dimethylamino)hexyl, 3-methansulfonylaminopropyl, 3-(N-ethyl-N-methylamino)propyl, 2-chloroethyl, 2-aminoethyl, 4-[(N,N-dimethylamino)methyl]phenyl, 3-(N,N-dimethylamino)-2-methylpropyl, 2-(1-methyl-2-piperidinyl)ethyl, 3-pyridylmethyl, 4-cyanobutyl, 4-(1H-benzimidazol-2-ylmethyl), 3-(N-methylamino)propyl, 2-(1-methyl-2-pyrrolidinyl)ethyl, 3-(1-azetidinyl)propyl, 3-{N-methyl-N-[2-(2-pyridinyl)ethyl]amino}propyl, 3-(N,N-diethylamino)propyl, 3-[N-isopropyl-N-(methyl)amino]propyl, 3-[N-(2-hydroxyethyl)-N-(isopropyl)amino]propyl, 3-[N,N-bis(2-hydroxyethyl)amino]propyl, 3-[N-(2-hydroxyethyl)-N-(methyl)amino]propyl, 3-[N-ethyl-N-(propyl)amino]propyl, 3-(4-methyl-1,4-diazepan-1-yl)propyl, 3-[N-hexyl-N-(methyl)amino]propyl, 3-(N-cyanomethyl-N-propyl)aminopropyl, 3-[N-[2-(N',N'-diethylamino)ethyl]-N-(methyl)amino]propyl, 3-[(N-cyanomethyl-N-methyl)amino]propyl, 3-[N-methyl-N-(2-phenylethyl)amino]propyl, 3-[N-ethyl-N-(2-hydroxyethyl)amino]propyl, 3-(3,4-dihydro-2(1H)-isoquinolinyl)propyl, N-methyl-4-piperidyl, 3-(N,N-dimethylamino)propyl, 4-piperidyl, 3-aminopropyl, cyanomethyl or 2-benzimidazolylmethyl.

9. A compound according to claim 1, wherein
$R^3$ is H, N-methyl-4-piperidyl, 3-N,N-dimethylpropyl, 4-piperidyl, 3-aminopropyl, cyanomethyl or 2-benzimidazolylmethyl.

10. A compound according to claim 1, wherein $R^3$ is H.

11. A compound according to claim 1, wherein
$Y^1$, $Y^2$, $Y^3$ and $Y^4$ are independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$-, $Q^2$-, $R^6(R^7)N$—, cyano, hydroxy and $R^6(R^7)NC(=O)$—, wherein $R^6$ and $R^7$ are independently selected from H and $C_{1-3}$alkyl; $R^8$ is aryl; $Q^1$ is a 4–10 membered monocyclic or bicyclic aromatic, partially saturated or fully saturated ring optionally containing up to 2 heteroatoms selected from O and N, and is optionally substituted with halo, $C_{1-2}$ alkyl, hydroxy, amino, $R^6(R^7)N$ $C_{1-2}$alkyl- or $R^6(R^7)NC_{1-2}$alkyl-O—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$—$C_{1-2}$alkyl- or $R^6(R^7)N$—$C_{1-2}$alkyl-O—, $R^6(R^7)N(O=)C$— or $R^6O(O=)C$—.

12. A compound according to claim 1, wherein
$Y^1$, $Y^2$, $Y^3$ and $Y^4$ are independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$-, $Q^2$-, $R^6(R^7)N$—, cyano, hydroxy and $R^6(R^7)NC(=O)$—, wherein $R^6$ and $R^7$ are independently selected from H, methyl and ethyl; $R^8$ is phenyl; $Q^1$ is phenyl, piperidyl, morpholino, pyridyl, benzimidazolyl, pyrrolidinyl, azetidinyl, diazepanyl or tetrahydroisoquinolyl being optionally substituted with halo, $C_{1-2}$ alkyl, hydroxy, amino, $R^6(R^7)N$ $C_{1-2}$alkyl- or $R^6(R^7)N$ $C_{1-2}$alkyl-O—; and $Q^2$ is phenyl or pyridyl being optionally substituted with halo, $C_{1-2}$ alkyl-, hydroxy, $C_{1-2}$ alkyl-O-, nitro, amino, cyano, $R^6(R^7)N$—$C_{1-2}$alkyl-, $R^6(R^7)N$—$C_{1-2}$ alkyl-O—, $R^6(R^7)N(O=)C$— or $R^6O(O=)C$—.

13. A compound according to claim 1, wherein
$Y^1$, $Y^2$, $Y^3$ and $Y^4$ are independently selected from H, fluoro, chloro, bromo, methyl, ethyl, iso-propyl, aminopropyl, methoxy, benzyl, aminobenzyl, hydroxybenzyl, chlorobenzyl, cyanobenzyl, methoxybenzyl, (N,N-dimethylaminoethoxy)benzyl, nitrobenzyl, aminomethylbenzyl, aminoethylbenzyl, carbamoylbenzyl, carboxybenzyl, anilino, benzoylamino, hydroxy(phenyl)methyl, phenyl, aminophenyl, hydroxyphenyl, cyanoethyl, pyridylmethyl and ethoxycarbonylethenyl.

14. A compound according to claim 1, wherein $Y^1$ is H, methyl, ethyl, propyl, aminophenyl, hydroxyphenyl, methoxy, fluoro or chloro;

$Y^2$ is hydrogen, methyl, ethyl, propyl, benzyl, chlorobenzyl, benzoylamino, hydroxybenzyl, methoxybenzyl, (N,N-dimethylaminoethoxy)benzyl, aminopropyl, anilino, nitrobenzyl, aminomethylbenzyl, (aminoethyl)benzyl, aminobenzyl, cyanobenzyl, hydroxy(phenyl)methyl, hydroxyphenyl, cyanoethyl, pyridylmethyl, carbamoylbenzyl, carboxybenzyl, ethoxycarbonylethenyl or fluoro;

$Y^3$ is hydrogen, ethyl, methyl, methoxy or fluoro; and $Y^4$ is hydrogen, chloro, fluoro, bromo, methyl, ethyl, methoxy or phenyl.

15. A compound according to claim 1, wherein
$Y^1$ is H, ethyl, 4-aminophenyl, iso-propyl, 4-hydroxyphenyl, methoxy or fluoro;

$Y^2$ is hydrogen, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl, 2-chlorobenzyl, methyl, 2-aminomethylbenzyl, 2-(2-aminoethyl)benzyl, 2-aminobenzyl, 2-methoxybenzyl, 3-aminobenzyl, 3-aminomethylbenzyl, 4-cyanobenzyl, hydroxy(phenyl)methyl, 2-hydroxyphenyl (3-hydroxyphenyl, 2-cyanoethyl, ethyl, 3-pyridylmethyl, 3-carbamoylbenzyl, 3-carboxybenzyl, ethoxycarbonylethenyl, 2-carbamoylbenzyl or fluoro;

$Y^3$ is hydrogen, methoxy or fluoro; and $Y^4$ is hydrogen, chloro, fluoro, bromo or ethyl.

16. A compound according to claim 1, wherein
$Y^1$ is H, ethyl or 4-aminophenyl;

$Y^2$ is H, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl or 2-chlorobenzyl;

$Y^3$ is H; and $Y^4$ is H.

17. A compound according to claim 1, wherein $R^1$ is $C_{1-2}$ alkyl;

$R^2$ is H or amino;

$R^3$ is H, halo-$CH_2$—, $R^4(R^5)NCH_2$—, $R^6(R^7)NC(=O)CH_2$—, cyano-$CH_2$—, $Q^1CH_2$—, $Q^1$-(O=)$CCH_2$—, $C_{2-6}$ alkyl or $Q^1$-, wherein said $C_{2-6}$ alkyl is optionally substituted with up to 3 substituents selected from halo, methyl, $R^4(R^5)N$, $C_{1-2}$ alkylsulfonylamino, $C_{1-2}$ alkylthio, $R^6(R^7)NC(=O)$—, cyano and $Q^1$- or $Q^1$-(O=)C—;

$R^4$ is H, $C_{1-6}$ alkyl, HO—$C_{1-2}$ alkyl, $Q^1$-, $Q^1$-$C_{1-3}$alkyl-, cyano- $C_{1-2}$alkyl- or $R^6(R^7)N$ $C_{1-2}$alkyl-;

$R^5$ is H, $C_{1-2}$alkyl, HO—$C_{1-2}$ alkyl or $Q^1$-;

$R^6$ and $R^7$ are independently selected from H and $C_{1-3}$ alkyl;

$R^8$ is aryl;

$Q^1$ is a 4–10 membered monocyclic or bicyclic aromatic, partially saturated or fully saturated ring optionally containing up to 2 heteroatoms selected from O and N, and is optionally substituted with halo, $C_{1-2}$ alkyl, hydroxy, amino, $R^6(R^7)N$ $C_{1-2}$alkyl- or $R^6(R^7)NC_{1-2}$alkyl-O—;

$Y^5$, $Y^6$, $Y^7$ and $Y^8$ are hydrogen;

$Y^1$, $Y^2$, $Y^3$ and $Y^4$ are independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$-, $Q^2$-, $R^6(R^7)N$—, cyano, hydroxy and $R^6(R^7)NC(=O)$—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$—$C_{1-2}$alkyl- or $R^6(R^7)N$—$C_{1-2}$alkyl-O—, $R^6(R^7)N(O=)C$— or $R^6O(O=)C$—.

18. A compound according to claim 1, wherein $R^1$ is $C_{1-2}$ alkyl;

$R^2$ is H or amino;

$R^3$ is H, halo-$CH_2$—, $R^4(R^5)NCH_2$—, $R^6(R^7)NC(=O)CH_2$—, cyano-$CH_2$—, $Q^1CH_2$—, $Q^1$-(O=)$CCH_2$—, $C_{2-6}$ alkyl or $Q^1$-, wherein said $C_{2-6}$ alkyl is optionally substituted with up to 3 substituents selected from halo, methyl, $R^4(R^5)N$, $C_{1-2}$ alkylsulfonylamino, $C_{1-2}$ alkylthio, $R^6(R^7)NC(=O)$—, cyano, $Q^1$- and $Q^1$-(O=)C—;

$R^4$ is H, $C_{1-6}$ alkyl, HO—$C_{1-2}$ alkyl, phenyl-$C_{1-3}$alkyl-, pyridyl-$C_{1-3}$alkyl-, cyano- $C_{1-2}$alkyl- or $R^6(R^7)N$ $C_{1-2}$alkyl-;

$R^5$ is H, $C_{1-2}$alkyl, HO—$C_{1-2}$ alkyl or $Q^1$-;

$R^6$ and $R^7$ are independently selected from H, methyl or ethyl;

$R^8$ is phenyl;

$Q^1$ is phenyl, piperidyl, morpholino, pyridyl, benzimidazolyl, pyrrolidinyl, azetidinyl, diazepanyl or tetrahydroisoquinolyl being optionally substituted with halo, $C_{1-2}$ alkyl, hydroxy, amino, $R^6(R^7)N$ $C_{1-2}$alkyl- or $R^6(R^7)N$ $C_{1-2}$alkyl-O—;

$Y^5$, $Y^6$, $Y^7$ and $Y^8$ are hydrogen;

$Y^1$, $Y^2$, $Y^3$ and $Y^4$ are independently selected from hydrogen, halo, $C_{1-3}$ alkyl, $C_{1-3}$ alkyl-O—, $C_{1-2}$ alkylthio, $Q^1$-, $R^6(R^8)N$—, $R^6N(R^7)C(=O)$—, $C_{1-2}$ alkyl-O(O=)CCH=CH—, $Q^1$-(O=)CNH— and $R^6OC(=O)$—, wherein said $C_{1-3}$alkyl is optionally substituted with up to 2 substituents selected from $Q^1$-, $Q^2$-, $R^6(R^7)N$—, cyano, hydroxy and $R^6(R^7)NC(=O)$—; and $Q^2$ is phenyl or pyridyl being optionally substituted with halo, $C_{1-2}$ alkyl-, hydroxy, $C_{1-2}$ alkyl-O—, nitro, amino, cyano, $R^6(R^7)N$—$C_{1-2}$alkyl-, $R^6(R^7)N$—$C_{1-2}$alkyl-O—, $R^6(R^7)N(O=)C$— or $R^6O(O=)C$—.

19. A compound according to claim 1, wherein $R^1$ is methyl;

$R^2$ is H or amino;

$R^3$ is hydrogen, ethyl, butyl, hexyl, iodopentyl, carbamoylmethyl, methylthioethyl, (N,N-dimethylamino)ethyl, morpholinoethyl, (N,N-dimethylamino)butyl, (N,N-dimethylamino)hexyl, methansulfonylaminopropyl, (N-ethyl-N-methylamino)propyl, chloroethyl, aminoethyl, [(N,N-dimethylamino)methyl]phenyl, (N,N-dimethylamino)(methyl)propyl, (1-methyl-2-piperidinyl) ethyl, pyridylmethyl, cyanobutyl, 2-benzimidazolylmethyl, (N-methylamino)propyl, (1-methyl-2-pyrrolidinyl) ethyl, (1-azetidinyl)propyl, {N-methyl-N-[(pyridinyl)ethyl]amino}propyl, (N,N-diethylamino)propyl, [N-isopropyl-N-(methyl)amino]propyl, [N-(2-hydroxyethyl)-N-(isopropyl)amino]propyl, [N,N-bis(2-hydroxyethyl)amino]propyl, [N-(hydroxyethyl)-N-(methyl)amino]propyl, [N-ethyl-N-(propyl)amino]propyl, (4-methyl-1,4-diazepan-1-yl)propyl, [N-hexyl-N-(methyl)amino]propyl, [N-(cyanomethyl)-N-(propyl)amino]propyl, [N-[(diethylamino)ethyl]-N-(methyl)amino]propyl, [N-(cyanomethyl)-N-(methyl)amino]propyl, [N-methyl-N-(phenylethyl)amino]propyl, [N-ethyl-N-(hydroxyethyl)amino]propyl, (3,4-dihydro-2(1H)-isoquinolinyl)propyl, N-methyl-piperidyl, (N,N-dimethylamino)propyl, piperidyl, aminopropyl or cyanomethyl; and $Y^1$, $Y^2$, $Y^3$ and $Y^4$ are independently selected from H, fluoro, chloro, bromo, methyl, ethyl, iso-propyl, aminopropyl, methoxy, benzyl, aminobenzyl, hydroxybenzyl, chlorobenzyl, cyanobenzyl, methoxybenzyl, (N,N-dimethylaminoethoxy)benzyl, nitrobenzyl, aminomethylbenzyl, aminoethylbenzyl, carbamoylbenzyl, carboxybenzyl, anilino, benzoylamino, hydroxy(phenyl)methyl, phenyl, aminophenyl, hydroxyphenyl, cyanoethyl, pyridylmethyl and ethoxycarbonylethenyl.

20. A compound according to claim 1, wherein $R^1$ is methyl;

$R^2$ is H or amino;

$R^3$ is H, ethyl, n-butyl, n-hexyl, 5-iodopentyl, carbamoylmethyl, 2-methylthioethyl, 2-(N,N-dimethylamino)ethyl, 2-morpholinoethyl, 4-(N,N-dimethylamino)butyl, 6-(N,N-dimethylamino)hexyl, 3-methansulfonylaminopropyl, 3-(N-ethyl-N-methylamino)propyl, 2-chloroethyl, 2-aminoethyl, 4-[(N,N-dimethylamino)methyl]phenyl, 3-(N,N-dimethylamino)-2-methylpropyl, 2-(1-methyl-2-piperidinyl)ethyl, 3-pyridylmethyl, 4-cyanobutyl, 4-(1H-benzimidazol-2-ylmethyl), 3-(N-methylamino)propyl, 2-(1-methyl-2-pyrrolidinyl)ethyl, 3-(1-azetidinyl)propyl, 3-{N-methyl-N-[2-(2-pyridinyl)ethyl]amino}propyl, 3-(N,N-diethylamino)propyl, 3-[N-isopropyl-N-(methyl)amino]propyl, 3-[N-(2-hydroxyethyl)-N-(isopropyl)amino]propyl, 3-[N,N-bis(2-hydroxyethyl)amino]propyl, 3-[N-(2-hydroxyethyl)-N-(methyl)amino]propyl, 3-[N-ethyl-N-(propyl)amino]propyl, 3-(4-methyl-1,4-diazepan-1-yl)

propyl, 3-[N-hexyl-N-(methyl)amino]propyl, 3-(N-cyanomethyl-N-propyl)aminopropyl, 3-[N-[2-(N',N'-diethylamino)ethyl]-N-(methyl)amino]propyl, 3-[(N-cyanomethyl-N-methyl)amino]propyl, 3-[N-methyl-N-(2-phenylethyl)amino]propyl, 3-[N-ethyl-N-(2-hydroxyethyl)amino]propyl, 3-(3,4-dihydro-2(1H)-isoquinolinyl)propyl, N-methyl-4-piperidyl, 3-(N,N-dimethylamino)propyl, 4-piperidyl, 3-aminopropyl, cyanomethyl or 2-benzimidazolylmethyl;

$Y^1$ is H, methyl, ethyl, propyl, aminophenyl, hydroxyphenyl, methoxy, fluoro or chloro;

$Y^2$ is hydrogen, methyl, ethyl, propyl, benzyl, chlorobenzyl, benzoylamino, hydroxybenzyl, methoxybenzyl, (N,N-dimethylaminoethoxy)benzyl, aminopropyl, anilino, nitrobenzyl, aminomethylbenzyl, (aminoethyl)benzyl, aminobenzyl, cyanobenzyl, hydroxy(phenyl)methyl, hydroxyphenyl, cyanoethyl, pyridylmethyl, carbamoylbenzyl, carboxybenzyl, ethoxycarbonylethenyl or fluoro;

$Y^3$ is hydrogen, ethyl, methyl, methoxy or fluoro; and $Y^4$ is hydrogen, chloro, fluoro, bromo, methyl, ethyl, methoxy or phenyl.

21. A compound according to claim 1, $R^1$ is methyl;

$R^2$ is H;

$R^3$ is H, N-methyl-4-piperidyl, 3-N,N-dimethylpropyl, 4-piperidyl, 3-aminopropyl, cyanomethyl or 2-benzimidazolylmethyl;

$Y^1$ is H, ethyl, 4-aminophenyl, iso-propyl, 4-hydroxyphenyl, methoxy or fluoro;

$Y^2$ is hydrogen, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl, 2-chlorobenzyl, methyl, 2-aminomethylbenzyl, 2-(2-aminoethyl)benzyl, 2-aminobenzyl, 2-methoxybenzyl, 3-aminobenzyl, 3-aminomethylbenzyl, 4-cyanobenzyl, hydroxy(phenyl)methyl, 2-hydroxyphenyl (3-hydroxyphenyl, 2-cyanoethyl, ethyl, 3-pyridylmethyl, 3-carbamoylbenzyl, 3-carboxybenzyl, ethoxycarbonylethenyl, 2-carbamoylbenzyl or fluoro;

$Y^3$ is hydrogen, methoxy or fluoro; and $Y^4$ is hydrogen, chloro, fluoro, bromo or ethyl.

22. A compound according to claim 1, the dashed lines represent double bonds $R^1$ is methyl;

$R^2$ is H;

$R^3$ is H;

$Y^1$ is H, ethyl or 4-aminophenyl;

$Y^2$ is H, 4-chlorobenzyl, benzoylamino, 3-chlorobenzyl, 2-hydroxybenzyl, 3-hydroxybenzyl, 4-methoxybenzyl, benzyl, 3-aminopropyl, anilino, 4-hydroxybenzyl, 3-nitrobenzyl, 3-methoxybenzyl or 2-chlorobenzyl;

$Y^3$ is H;

$Y^4$ is H; and $Y^5$, $Y^6$, $Y^7$ and $Y^8$ are absence.

23. A compound according to claim 1 selected from 7-(4-chlolobenzyl)-1-methyl-1,4-dihydro-9H-pyrazolo[4,3-b]quinolin-9-one;

N-(1-methyl-9-oxo-4,9-dihydro-1H-pyrazolo[4,3-b]quinolin-7-yl)benzamide;

7-(3-chlolobenzyl)-1-methyl-1,4-dihydro-9H-pyrazolo[4,3-b]quinolin-9-one;

sodium 2-[[1-methyl-1,4-dihydro-9H-pyrazolo[4,3-b]quinolin-9-one]-7-yl-methyl]phenoxide;

7-(3-hydroxybenzyl)-1-methyl-1,4-dihydro-9H-pyrazolo[4,3-b]quinolin-9-one;

7-(4-methoxybenzyl)-1-methyl-1,4-dihydro-9H-pyrazolo[4,3-b]quinolin-9-one;

8-ethyl-1-methyl-1,4-dihydro-9H-pyrazolo[4,3-b]quinolin-9-one;

7-benzyl-1-methyl-1,4-dihydro-9H-pyrazolo[4,3-b]quinolin-9-one;

8-(4-aminophenyl)-1-methyl-1,4-dihydro-9H-pyrazolo[4,3-b]quinolin-9-one hydrochloride;

7-(3-aminopropyl)-1-methyl-1,4-dihydro-9H-pyrazolo[4,3-b]-quinolin-9-one hydrochloride;

7-anilino-1-methyl-1,4-dihydro-9H-pyrazolo[4,3-b]-quinolin-9-one;

1-methyl-7-(3-nitrobenzyl)-1,4-dihydro-9H-pyrazolo[4,3-b]quinolin-9-one;

7-(3-methoxybenzyl)-1-methyl-1,4-dihydro-9H-pyrazolo[4,3-b]quinolin-9-one;

7-(2-chlorobenzyl)-1-methyl-1,4-dihydro-9H-pyrazolo[4,3-b]quinolin-9-one;

7-[2-(aminomethyl)benzyl]-1-methyl-1,4-dihydro-9H-pyrazolo[4,3-b]quinolin-9-one hydrochloride; and 7-[2-(2-aminoethyl)benzyl]-1-methyl-1,4-dihydro-9H-pyrazolo[4,3-b]quinolin-9-one hydrochloride;

and salts thereof.

24. A compound according to claim 23 selected from 7-(4-chlolobenzyl)-1-methyl-1,4-dihydro-9H-pyrazolo[4,3-b]quinolin-9-one;

N-(1-methyl-9-oxo-4,9-dihydro-1H-pyrazolo[4,3-b]quinolin-7-yl)benzamide;

7-(3-chlolobenzyl)-1-methyl-1,4-dihydro-9H-pyrazolo[4,3-b]quinolin-9-one;

sodium 2-[[1-methyl-1,4-dihydro-9H-pyrazolo[4,3-b]quinolin-9-one]-7-yl-methyl]phenoxide;

7-(3-hydroxybenzyl)-1-methyl-1,4-dihydro-9H-pyrazolo[4,3-b]quinolin-9-one;

7-(4-methoxybenzyl)-1-methyl-1,4-dihydro-9H-pyrazolo[4,3-b]quinolin-9-one;

8-ethyl-1-methyl-1,4-dihydro-9H-pyrazolo[4,3-b]quinolin-9-one; and 7-benzyl-1-methyl-1,4-dihydro-9H-pyrazolo[4,3-b]quinolin-9-one;

and salts thereof.

25. A pharmaceutical composition for the treatment of disease conditions mediated by protein kinase C, in a mammalian subject, which comprises a therapeutically effective amount of a compound of claim 1 or its pharmaceutically acceptable carrier.

26. A pharmaceutical composition for the treatment of neuropathic pain, acute or chronic inflammatory pain, auditory deficiency (synaptic repair), hypertension, focal cerebral ischemia, pulmonary fibrosis, diabetes, immune disease, colonic repair, drug resistance (MDR regulation), Alzheimer, sepsis, shock, ARDS, inflammation, ischemia, gastric acid regulation, diabetic neuropathy, asthma, HIV infection, gastric ulcer or cerebral ischemia, which comprises a therapeutically effective amount of a compound of claim 1 or its pharmaceutically acceptable carrier.

27. A method for the treatment of disease conditions mediated by protein kinase C, in a mammalian subject, which comprises administering to said subject a therapeutically effective amount of a compound according to claim 1.

28. A method for the treatment of neuropathic pain, acute or chronic inflammatory pain, auditory deficiency (synaptic repair), hypertension, focal cerebral ischemia, pulmonary fibrosis, diabetes, immune disease, colonic repair, drug resistance (MDR regulation), Alzheimer, sepsis, shock, ARDS, inflammation, ischemia, gastric acid regulation, diabetic neuropathy, asthma, HIV infection, gastric ulcer or cerebral ischemia, in a mammalian subject, which comprises administering to said subject a therapeutically effective amount of a compound according to claim 1.

29. A pharmaceutical formulation comprising a compound of claim 1, a pharmaceutically acceptable carrier and, optionally, one or more other pharmacologically active ingredients.

* * * * *

UNITED STATES PATENT AND TRADEMARK OFFICE
CERTIFICATE OF CORRECTION

PATENT NO.    : 6,686,373 B2
DATED         : February 3, 2004
INVENTOR(S)   : Kiyoshi Kawamura et al.

It is certified that error appears in the above-identified patent and that said Letters Patent is hereby corrected as shown below:

Title page,
Item [74], *Attorney, Agent, or Firm*, "David R. Kurlandsky; Charles W. Asshbrook" should read -- David R. Kurlandsky; Charles W. Ashbrook --

Column 98,
Line 46, "bicyclic aromatic, partially saturated or frilly saturated" should read -- bicyclic aromatic, partially saturated or fully saturated --
Line 54, "dimethylamino)ethyl, morpholion ethyl, (N,N-" should read -- dimethylamino)ethyl, morpholinoethyl (N,N- --

Signed and Sealed this

Twenty-eighth Day of June, 2005

JON W. DUDAS
*Director of the United States Patent and Trademark Office*